(12) United States Patent
Friedman et al.

(10) Patent No.: US 8,504,132 B2
(45) Date of Patent: Aug. 6, 2013

(54) METHODS AND APPARATUS FOR ASSESSING AND IMPROVING ELECTRODE CONTACT WITH CARDIAC TISSUE

(76) Inventors: Paul Friedman, Rochester, MN (US);
Charles J. Bruce, Rochester, MN (US);
Ryan Amara, Tewksbury, MA (US);
Jeremiah Johnson, Candia, NH (US);
Peter D. Kozel, Acton, MA (US)

( * ) Notice: Subject to any disclaimer, the term of this patent is extended or adjusted under 35 U.S.C. 154(b) by 736 days.

(21) Appl. No.: 12/308,862

(22) PCT Filed: Jun. 28, 2007

(86) PCT No.: PCT/US2007/015066
§ 371 (c)(1),
(2), (4) Date: Mar. 4, 2010

(87) PCT Pub. No.: WO2008/002654
PCT Pub. Date: Jan. 3, 2008

(65) Prior Publication Data
US 2010/0198040 A1    Aug. 5, 2010

Related U.S. Application Data

(60) Provisional application No. 60/817,119, filed on Jun. 28, 2006.

(51) Int. Cl.
*A61B 5/042* (2006.01)
*A61B 18/14* (2006.01)

(52) U.S. Cl.
USPC ............. 600/374; 600/393; 600/509; 606/41

(58) Field of Classification Search
USPC .............................. 600/374, 393, 509; 606/41
See application file for complete search history.

(56) References Cited

U.S. PATENT DOCUMENTS

| | | | |
|---|---|---|---|
| 5,311,866 A | 5/1994 | Kagan et al. | |
| 5,397,341 A | 3/1995 | Hirschberg et al. | |
| 5,795,325 A * | 8/1998 | Valley et al. | 604/509 |
| 5,799,533 A * | 9/1998 | Seki et al. | 73/172 |
| 5,836,990 A | 11/1998 | Li | |
| 5,891,136 A * | 4/1999 | McGee et al. | 606/41 |
| 5,893,848 A * | 4/1999 | Negus et al. | 606/41 |
| 5,899,927 A | 5/1999 | Ecker | |

(Continued)

FOREIGN PATENT DOCUMENTS

WO    WO 2005/115231 A1    12/2005

OTHER PUBLICATIONS

Supplementary European Search Report from EP Application No. 07796563.

*Primary Examiner* — Lee S Cohen
*Assistant Examiner* — Erin M Cardinal
(74) *Attorney, Agent, or Firm* — Wolf, Greenfield & Sacks, P.C.

(57) ABSTRACT

Embodiments of the invention relate to methods for assessing and/or improving contact between an electrophysiology catheter and tissue, and catheters for performing the methods. One embodiment relates to a catheter comprising a braided conductive member coupled to the distal end of a shaft, wherein the braided conductive member comprises a plurality of pressure sensitive wires. Another embodiment relates to a catheter comprising a braided conductive member having a plurality of sectors and coupled to the distal end of a shaft, and a balloon assembly constructed and arranged to selectively apply distal pressure to one or more sectors of the braided conductive member.

36 Claims, 51 Drawing Sheets

U.S. PATENT DOCUMENTS

| | | |
|---|---|---|
| 5,908,446 A | 6/1999 | Imran |
| 6,002,956 A | 12/1999 | Schaer |
| 6,047,218 A | 4/2000 | Whayne et al. |
| 6,210,406 B1 | 4/2001 | Webster |
| 6,240,307 B1 | 5/2001 | Beatty |
| 6,436,059 B1 * | 8/2002 | Zanelli .................... 600/587 |
| 6,543,299 B2 * | 4/2003 | Taylor .................. 73/862.046 |
| 6,656,174 B1 | 12/2003 | Hegde |
| 6,826,421 B1 | 11/2004 | Beatty et al. |
| 6,837,886 B2 | 1/2005 | Collins et al. |
| 6,955,675 B2 | 10/2005 | Jain |
| 7,255,695 B2 | 8/2007 | Falwell et al. |
| 7,306,594 B2 | 12/2007 | Collins et al. |
| 8,048,063 B2 * | 11/2011 | Aeby et al. .................. 606/1 |
| 2004/0060362 A1 | 4/2004 | Kjellmann |
| 2004/0243124 A1 | 12/2004 | Im et al. |
| 2005/0159741 A1 * | 7/2005 | Paul et al. .................. 606/41 |
| 2005/0267467 A1 | 12/2005 | Paul et al. |
| 2007/0129717 A1 * | 6/2007 | Brown et al. ............... 606/41 |
| 2007/0191830 A1 * | 8/2007 | Crompton et al. .......... 606/41 |
| 2008/0058800 A1 | 3/2008 | Collins et al. |

* cited by examiner

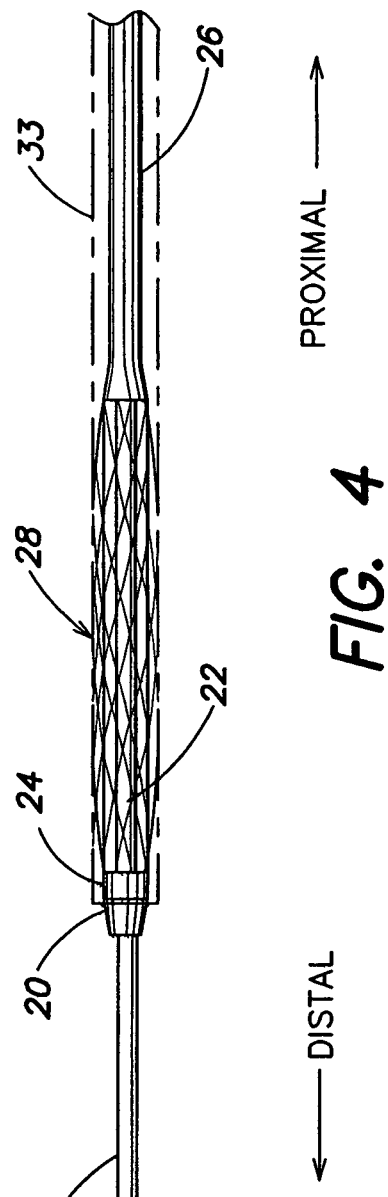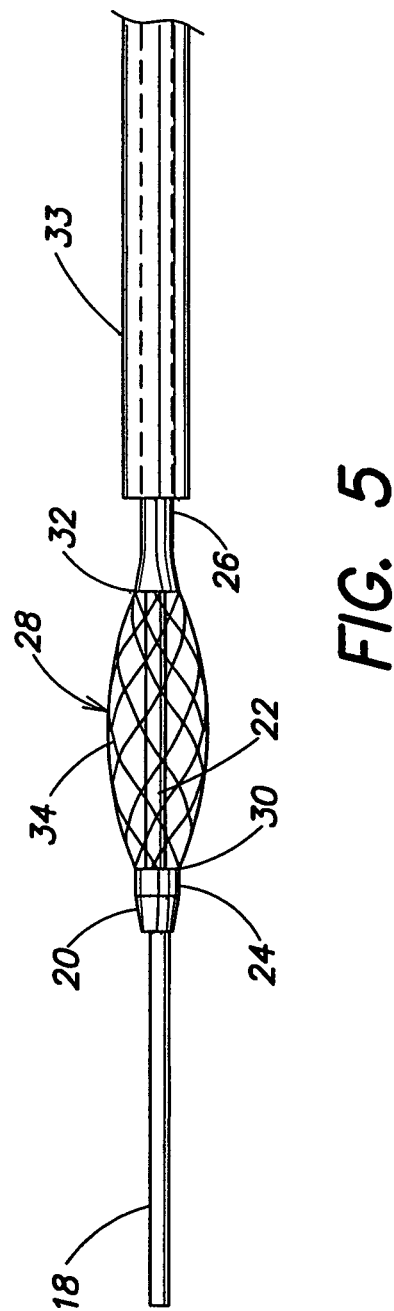

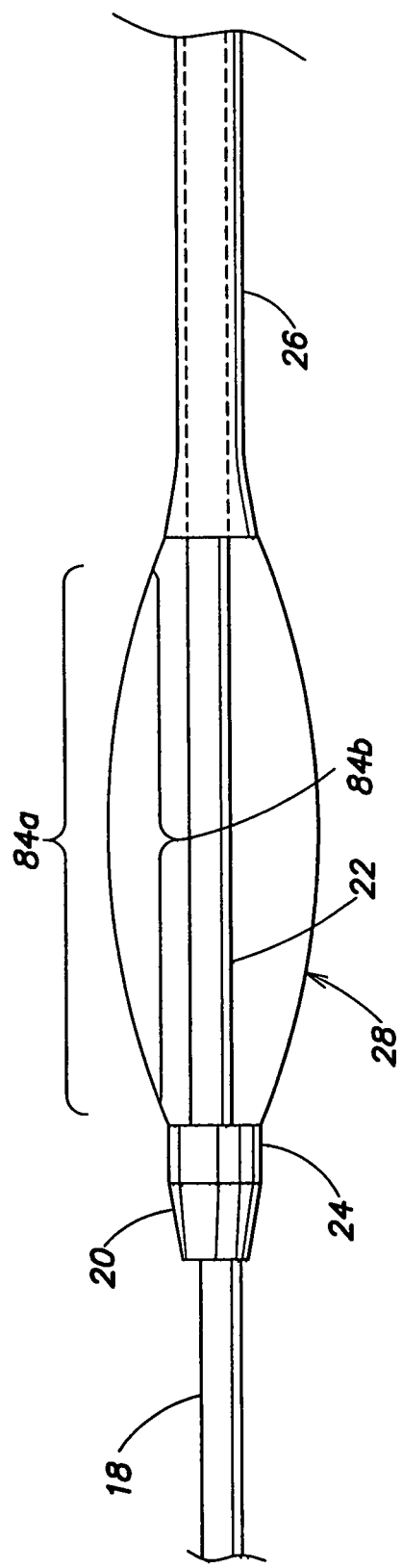

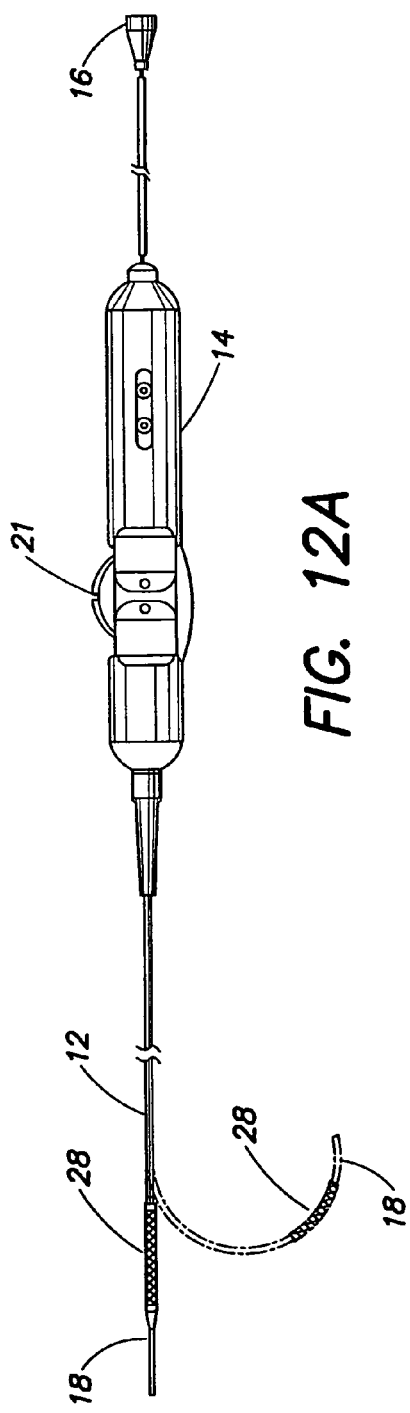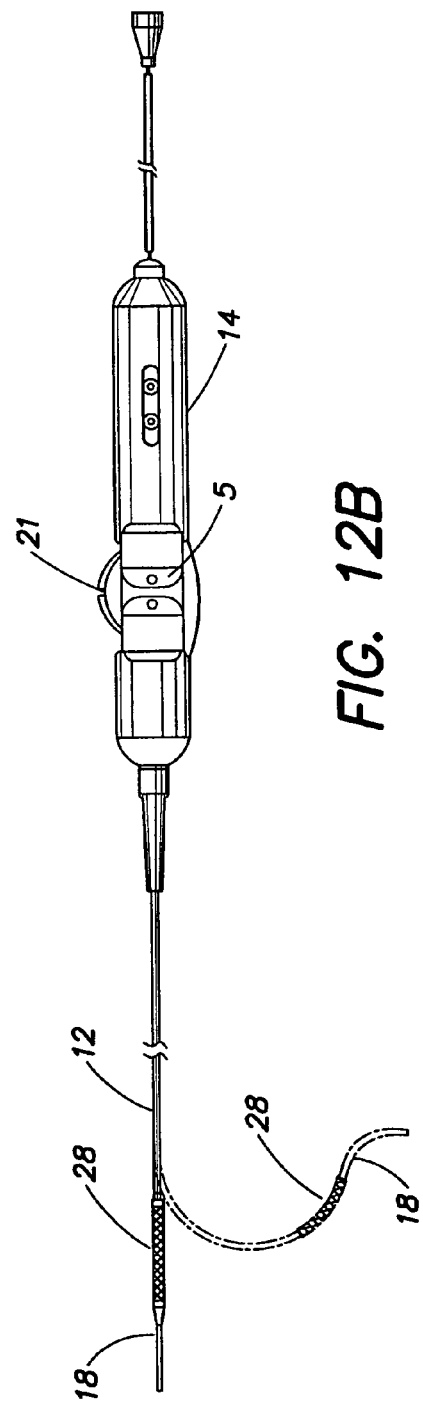

METHODS AND APPARATUS FOR ASSESSING AND IMPROVING ELECTRODE CONTACT WITH CARDIAC TISSUE

CROSS-REFERENCE TO RELATED APPLICATIONS

This application claims the benefit, under 35 U.S.C. §119 (e), of the filing date of U.S. provisional application Ser. No. 60/817,119 entitled "Methods of Assessing and Improving Electrode Contact with Cardiac Tissue," filed Jun. 28, 2006, which is hereby incorporated herein by reference in its entirety.

FIELD OF INVENTION

The invention relates generally to methods and apparatus for assessing and improving contact between an electrophysiology catheter and cardiac tissue.

BACKGROUND OF THE INVENTION

The human heart is a very complex organ, which relies on both muscle contraction and electrical impulses to function properly. The electrical impulses travel through the heart walls, first through the atria and then the ventricles, causing the corresponding muscle tissue in the atria and ventricles to contract. Thus, the atria contract first, followed by the ventricles. This order is essential for proper functioning of the heart.

Over time, the electrical impulses traveling through the heart can begin to travel in improper directions, thereby causing the heart chambers to contract at improper times. Such a condition is generally termed a cardiac arrhythmia, and can take many different forms. When the chambers contract at improper times, the amount of blood pumped by the heart decreases, which can result in premature death of the person.

Techniques have been developed which are used to locate cardiac regions responsible for the cardiac arrhythmia, and also to disable the short-circuit function of these areas. According to these techniques, electrical energy is applied to a portion of the heart tissue to ablate that tissue and produce scars which interrupt the reentrant conduction pathways or terminate the focal initiation. The regions to be ablated are usually first determined by endocardial mapping techniques. Mapping typically involves percutaneously introducing a catheter having one or more electrodes into the patient, passing the catheter through a blood vessel (e.g. the femoral vein or artery) and into an endocardial site (e.g., the atrium or ventricle of the heart), and deliberately inducing an arrhythmia so that a continuous, simultaneous recording can be made with a multichannel recorder at each of several different endocardial positions. When an arrhythmogenic focus or inappropriate circuit is located, as indicated in the electrocardiogram recording, it is marked by various imaging or localization means so that cardiac arrhythmias emanating from that region can be blocked by ablating tissue. An ablation catheter with one or more electrodes can then transmit electrical energy to the tissue adjacent the electrode to create a lesion in the tissue. One or more suitably positioned lesions will typically create a region of necrotic tissue which serves to disable the propagation of the errant impulse caused by the arrhythmogenic focus. Ablation is carried out by applying energy to the catheter electrodes. The ablation energy can be, for example, RF, DC, ultrasound, microwave, or laser radiation.

Atrial fibrillation together with atrial flutter are the most common sustained arrhythmias found in clinical practice.

Current understanding is that atrial fibrillation is frequently initiated by a focal trigger from the orifice of or within one of the pulmonary veins. Though mapping and ablation of these triggers appears to be curative in patients with paroxysmal atrial fibrillation, there are a number of limitations to ablating focal triggers via mapping and ablating the earliest site of activation with a "point" radiofrequency lesion. One way to circumvent these limitations is to determine precisely the point of earliest activation. Once the point of earliest activation is identified, a lesion can be generated to electrically isolate the trigger with a lesion; firing from within those veins would then be eliminated or unable to reach the body of the atrium, and thus could not trigger atrial fibrillation.

Another method to treat focal arrhythmias is to create a continuous, annular lesion around the ostia (i.e., the openings) of either the veins or the arteries leading to or from the atria thus "corralling" the signals emanating from any points distal to the annular lesion. Conventional techniques include applying multiple point sources around the ostia in an effort to create such a continuous lesion. Such a technique is relatively involved, and requires significant skill and attention from the clinician performing the procedures.

Another source of arrhythmias may be from reentrant circuits in the myocardium itself. Such circuits may not necessarily be associated with vessel ostia, but may be interrupted by means of ablating tissue either within the circuit or circumscribing the region of the circuit. It should be noted that a complete 'fence' around a circuit or tissue region is not always required in order to block the propagation of the arrhythmia; in many cases simply increasing the propagation path length for a signal may be sufficient. Conventional means for establishing such lesion 'fences' include a multiplicity of point-by-point lesions, dragging a single electrode across tissue while delivering energy, or creating an enormous lesion intended to inactivate a substantive volume of myocardial tissue.

SUMMARY OF INVENTION

One embodiment of the invention is directed to a method, comprising introducing a catheter having a braided conductive member into a heart; positioning the braided conductive member at a desired location for performing ablation or mapping; sensing a first degree of pressure between a first sector of the braided conductive member and first adjacent tissue; sensing a second degree of pressure between a second sector of the braided conductive member and second adjacent tissue; and providing an indication of contact between at least a portion of the braided conductive member and adjacent tissue based on at least one of the first degree of pressure and the second degree of pressure.

Another embodiment of the invention is directed to an electrophysiology catheter comprising a handle; a shaft coupled to a distal end of the handle; and a braided conductive member coupled to a distal end of the shaft. The braided conductive member comprises a plurality of pressure sensitive wires.

A further embodiment of the invention is directed to an electrophysiology catheter comprising: a handle; a shaft coupled to a distal end of the handle; a braided conductive member coupled to a distal end of the shaft, the braided conductive member comprising a plurality of sectors; and a balloon assembly constructed and arranged to selectively apply distal pressure to one or more sectors of the braided conductive member.

Another embodiment of the invention is directed to an electrophysiology catheter comprising: a handle; a shaft coupled to a distal end of the handle; a braided conductive member coupled to a distal end of the shaft, the braided conductive member comprising a plurality of sectors; and means, coupled to the shaft, for selectively applying distal pressure to one or more sectors of the braided conductive member.

BRIEF DESCRIPTION OF THE DRAWINGS

In the drawings, which are incorporated herein by reference and in which like elements have been given like references characters.

FIGS. 4-7 illustrate further details of the braided conductive member illustrated in FIGS. 2 and 3;

FIGS. 12-13 illustrate further details of the steering capabilities of the present invention;

DETAILED DESCRIPTION

System Overview

Figure 1:
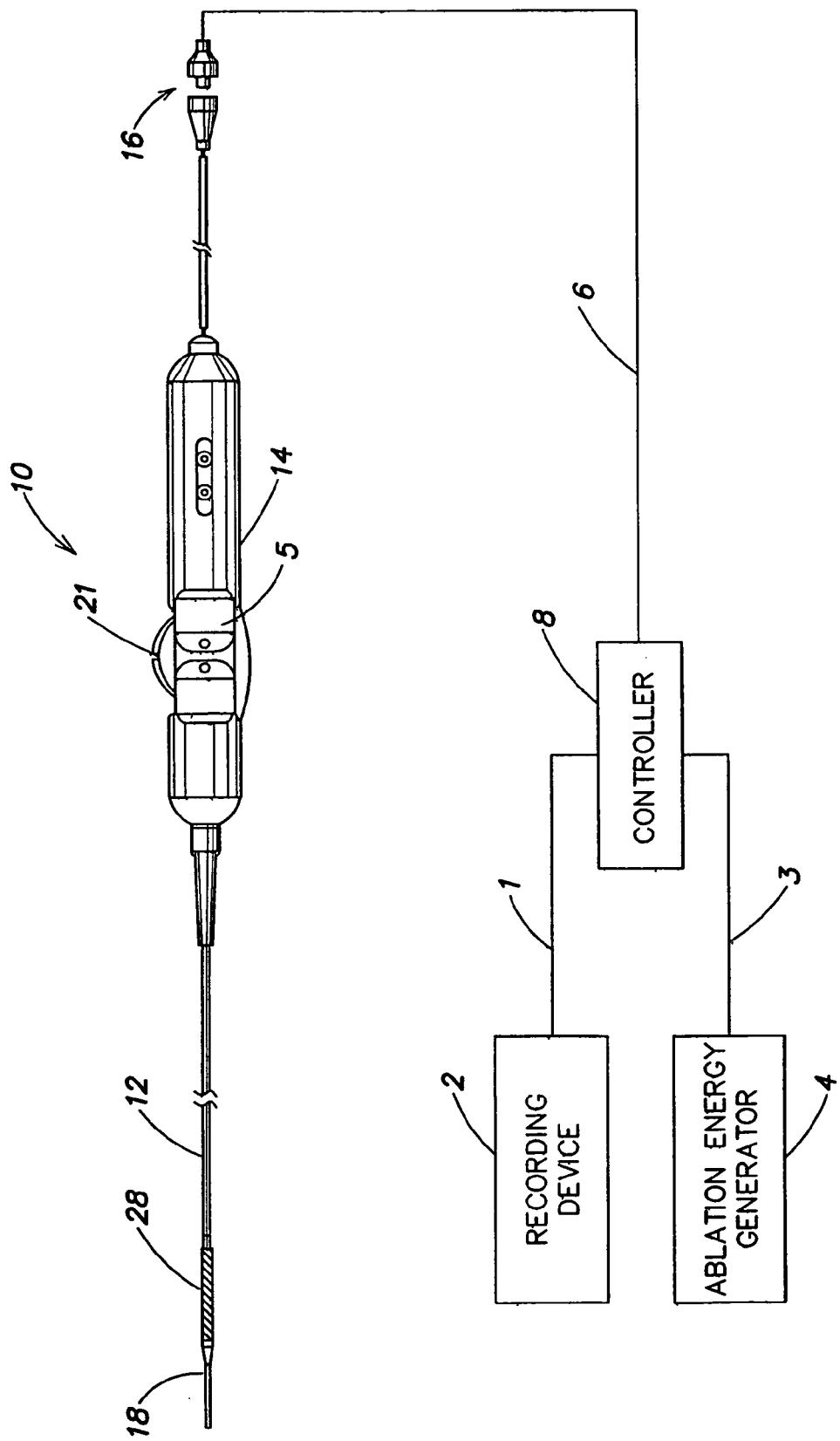
FIG. 1 illustrates an overview of a mapping and ablation catheter system in accordance with the present invention.

Reference is now made to FIG. 1, which figure illustrates an overview of a mapping and ablation catheter system in accordance with the present invention. The system includes a catheter 10 having a shaft portion 12, a control handle 14, and a connector portion 16. A controller 8 is connected to connector portion 16 via cable 6. Ablation energy generator 4 may be connected to controller 8 via cable 3. A recording device 2 may be connected to controller 8 via cable 1. When used in an ablation application, controller 8 is used to control ablation energy provided by ablation energy generator 4 to catheter 10. When used in a mapping application, controller 8 is used to process signals coming from catheter 10 and to provide these signals to recording device 2. Although illustrated as separate devices, recording device 2, ablation energy generator 4, and controller 8 could be incorporated into a single device. In one embodiment, controller 8 may be a QUADRAPULSE RF CONTROLLER™ device available from CR Bard, Inc., Murray Hill, N.J.

In this description, various aspects and features of the present invention will be described. The various features of the invention are discussed separately for clarity. One skilled in the art will appreciate that the features may be selectively combined in a device depending upon the particular application. Furthermore, any of the various features may be incorporated in a catheter and associated method of use for either mapping or ablation procedures.

Catheter Overview

Reference is now made to FIGS. 2-7, which figures illustrate one embodiment of the present invention. The present invention generally includes a catheter and method of its use for mapping and ablation in electrophysiology procedures. Catheter 10 includes a shaft portion 12, a control handle 14, and a connector portion 16. When used in mapping applications, connector portion 16 is used to allow signal wires running from the electrodes at the distal portion of the catheter to be connected to a device for processing the electrical signals, such as a recording device.

Figure 2:
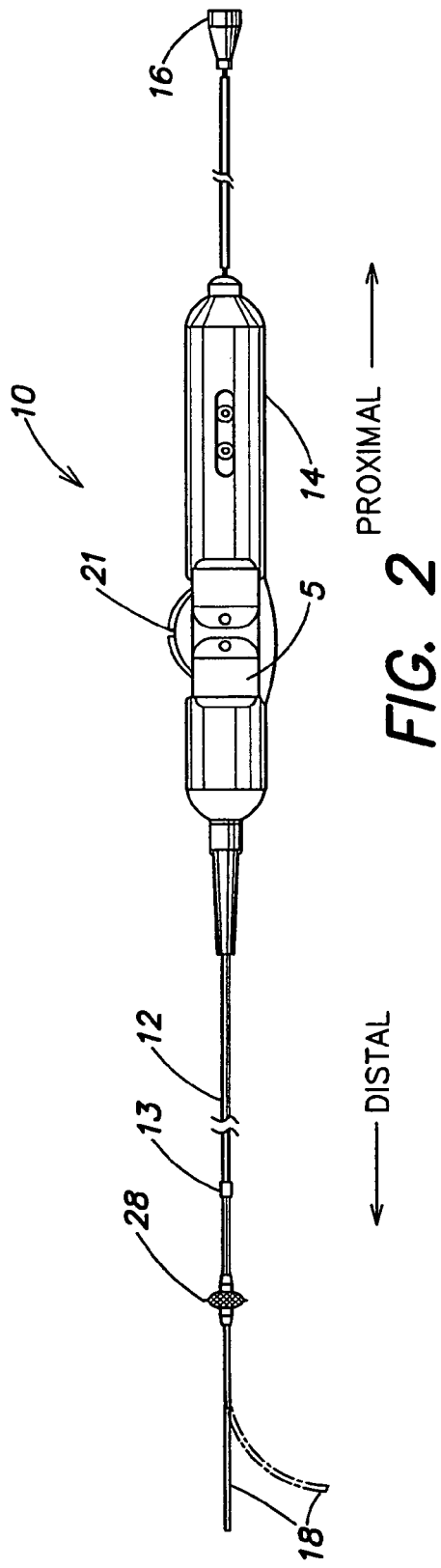
FIGS. 2 and 3 illustrate further details of the catheter illustrated in FIG. 1.

Catheter 10 may be a steerable device. FIG. 2 illustrates the distal tip portion 18 being deflected by the mechanism contained within control handle 14. Control handle 14 may include a rotatable thumbwheel 21 and/or a slide actuator 5 which can be used by a user to deflect the distal end of the catheter. The thumbwheel (or any other suitable actuating device) is connected to one or more pull wires which extend through shaft portion 12 and are connected to the distal end 18 of the catheter at an off-axis location, whereby tension applied to one or more of the pull wires causes the distal portion of the catheter to curve in a predetermined direction or directions. U.S. Pat. Nos. 5,383,852, 5,462,527, and 5,611,777, which are hereby incorporated by reference, illustrate various embodiments of control handle 14 that may be used for steering catheter 10.

Shaft portion 12 includes a distal tip portion 18, a first stop 20 and an inner member 22 connected to the first stop portion 20. Inner member 22 may be a tubular member. Concentrically disposed about inner member 22 is a first sheath 24 and a second sheath 26. Also concentrically disposed about inner member 22 is a braided conductive member 28 anchored at respective ends 30 and 32 to the first sheath 24 and the second sheath 26, respectively.

Figure 3:
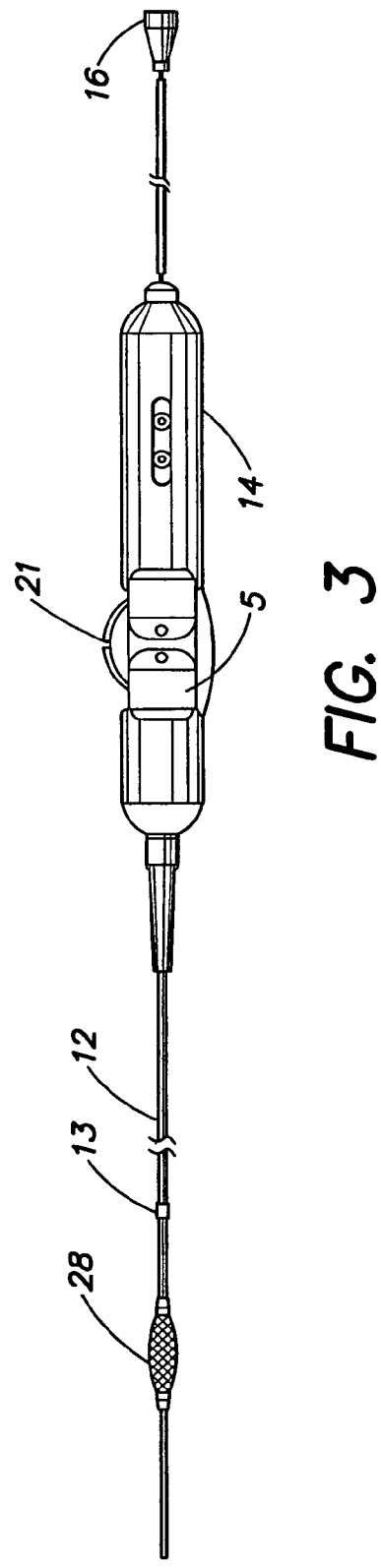

In operation, advancing the second sheath 26 distally over inner member 22 causes the first sheath 24 to contact stop 20. Further distal advancement of the second sheath 26 over inner member 22 causes the braided conductive member 28 to expand radially to assume various diameters and/or a conical shape. FIG. 3 illustrates braided conductive member 28 in an unexpanded (collapsed or "undeployed") configuration. FIGS. 2 and 5 illustrate braided conductive member 28 in a partially expanded condition. Braided conductive member 28 may be radially expanded ("deployed") to form a disk.

Alternatively, braided conductive member 28 can be radially expanded by moving inner member 22 proximally with respect to the second sheath 26.

As another alternative, inner member 22 and distal tip portion 18 may be the same shaft and stop 20 may be removed. In this configuration, sheath 24 moves over the shaft in response to, for example, a mandrel inside shaft 22 and attached to sheath 24 in the manner described, for example, in U.S. Pat. No. 6,178,354, which is incorporated herein by reference.

As illustrated particularly in FIGS. 4 and 5 a third sheath 33 may be provided. The third sheath serves to protect shaft portion 12 and in particular braided conductive member 28 during manipulation through the patient's vasculature. In addition, the third sheath 33 shields braided conductive member 28 from the patient's tissue in the event ablation energy is prematurely delivered to the braided conductive member 28.

The respective sheaths 24, 26, and 33 can be advanced and retracted over the inner member 22, which may be a tubular member, in many different manners. Control handle 14 may be used. U.S. Pat. Nos. 5,383,852, 5,462,527, and 5,611,777 illustrate examples of control handles that can control sheaths 24, 26, and 33. As described in these incorporated by reference patents, control handle 14 may include a slide actuator which is axially displaceable relative to the handle. The slide actuator may be connected to one of the sheaths, for example, the second sheath 26 to control the movement of the sheath 26 relative to inner member 22, to drive braided conductive member 28 between respective collapsed and deployed positions, as previously described. Control handle 14 may also include a second slide actuator or other mechanism coupled to the retractable outer sheath 33 to selectively retract the sheath in a proximal direction with respect to the inner member 22.

Braided conductive member 28 is, in one embodiment of the invention, a plurality of interlaced, electrically conductive filaments 34. Braided conductive member 28 may be a wire mesh. The filaments are flexible and capable of being expanded radially outwardly from inner member 22. The filaments 34 are preferably formed of metallic elements having relatively small cross sectional diameters, such that the filaments can be expanded radially outwardly. The filaments may be round, having a dimension on the order of about 0.001-0.030 inches in diameter. Alternatively, the filaments may be flat, having a thickness on the order of about 0.001-0.030 inches, and a width on the order of about 0.001-0.030 inches. The filaments may be formed of Nitinol type wire. Alternatively, the filaments may include non metallic elements woven with metallic elements, with the non metallic elements providing support to or separation of the metallic elements. A multiplicity of individual filaments 34 may be provided in braided conductive member 28, for example up to 300 or more filaments.

Each of the filaments 34 can be electrically isolated from each other by an insulation coating. This insulation coating may be, for example, a polyimide type material. A portion of the insulation on the outer circumferential surface 60 of braided conductive member 28 is removed. This allows each of the filaments 34 to form an isolated electrode, not an electrical contact with any other filament, that may be used for mapping and ablation. Alternatively, specific filaments may be permitted to contact each other to form a preselected grouping.

Figure 6:
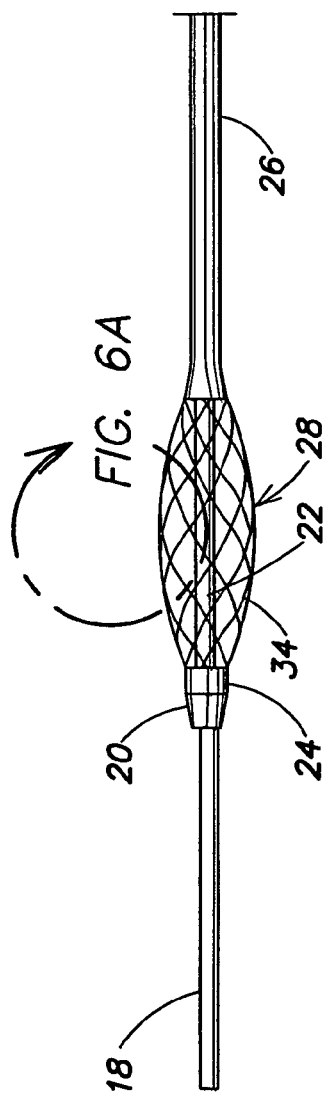
Figure 6A:
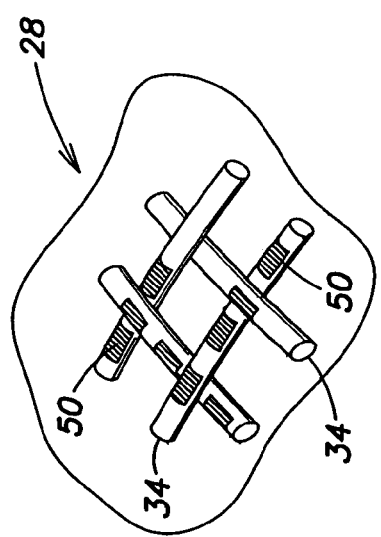
Figure 7:
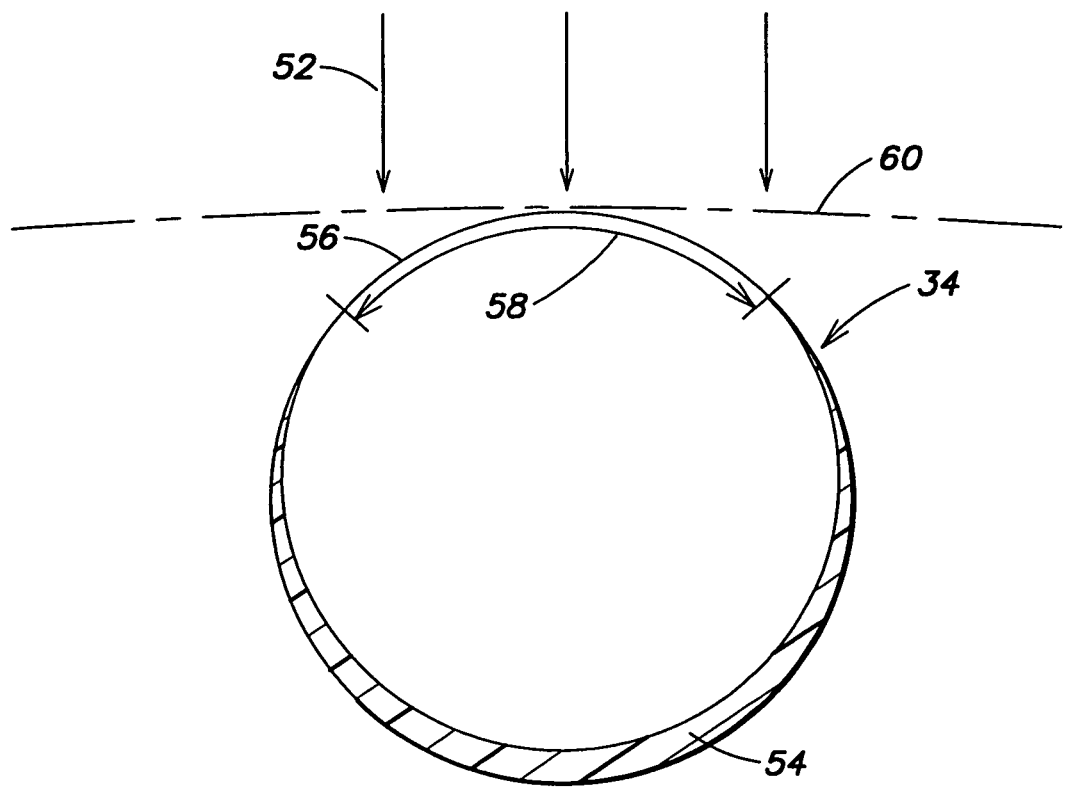

Each of the filaments 34 is helically wound under compression about inner member 22. As a result of this helical construction, upon radial expansion of braided conductive member 28, the portions of filaments 34 that have had the insulation stripped away do not contact adjacent filaments and thus, each filament 34 remains electrically isolated from every other filament. FIG. 6, in particular, illustrates how the insulation may be removed from individual filaments 34 while still providing isolation between and among the filaments. As illustrated in FIG. 6, regions 50 illustrate regions, on the outer circumferential surface 60 of braided conductive member 28, where the insulation has been removed from individual filaments 34. In one embodiment of the invention, the insulation may be removed from up to one half of the outer facing circumference of each of the individual filaments 34 while still retaining electrical isolation between each of the filaments 34.

The insulation on each of the filaments 34 that comprise braided conductive member 28 may be removed about the outer circumferential surface 60 of braided conductive member 28 in various ways. For example, one or more circumferential bands may be created along the length of braided conductive member 28. Alternatively, individual sectors or quadrants only may have their insulation removed about the circumference of braided conductive member 28. Alternatively, only selected filaments 34 within braided conductive member 28 may have their circumferentially facing insulation removed. Thus, an almost limitless number of configurations of insulation removal about the outer circumferential surface 60 of braided conductive member 28 can be provided depending upon the mapping and ablation characteristics and techniques that a clinician desires.

The insulation on each of the filaments 34 may be removed at the outer circumferential surface 60 of braided conductive member 28 in a variety of ways as long as the insulation is maintained between filaments 34 so that filaments 34 remain electrically isolated from each other.

The insulation can be removed from the filaments 34 in a variety of ways to create the stripped portions 50 on braided conductive member 28. For example, mechanical means such as abrasion or scraping may be used. In addition, a water jet, chemical means, or thermal radiation means may be used to remove the insulation.

In one example of insulation removal, braided conductive member 28 may be rotated about inner member 22, and a thermal radiation source such as a laser may be used to direct radiation at a particular point along the length of braided conductive member 28. As the braided conductive member 28 is rotated and the thermal radiation source generates heat, the insulation is burned off the particular region.

Insulation removal may also be accomplished by masking selected portions of braided conductive member 28. A mask, such as a metal tube may be placed over braided conducive member 28. Alternatively, braided conductive member 28 may be wrapped in foil or covered with some type of photoresist. The mask is then removed in the areas in which insulation removal is desired by, for example, cutting away the mask, slicing the foil, or removing the photoresist. Alternatively, a mask can be provided that has a predetermined insulation removal pattern. For example, a metal tube having cutouts that, when the metal tube is placed over braided conductive member 28, exposes areas where insulation is to be removed.

FIG. 6 illustrates how thermal radiation 52 may be applied to the outer circumferential surface 56 of a respective filament 34 that defines the outer circumferential surface 60 of braided conductive member 28. As thermal radiation 52 is applied, the insulation 54 is burned off or removed from the outer circumference 56 of wire 34 to create a region 58 about the circumference 56 of filament 34 that has no insulation.

The insulation 54 can also be removed in a preferential manner so that a particular portion of the circumferential surface 56 of a filament 34 is exposed. Thus, when braided conductive member 28 is radially expanded, the stripped portions of filaments may preferentially face the intended direction of mapping or ablation.

With the insulation removed from the portions of filaments 34 on the outer circumferential surface 60 of braided conductive member 28, a plurality of individual mapping and ablation channels can be created. A wire runs from each of the filaments 34 within catheter shaft 12 and control handle 14 to connector portion 16. A multiplexer or switch box may be connected to the conductors so that each filament 34 may be controlled individually. This function may be incorporated into controller 8. A number of filaments 34 may be grouped together for mapping and ablation. Alternatively, each individual filament 34 can be used as a separate mapping channel for mapping individual electrical activity within a blood vessel at a single point. Using a switch box or multiplexer to configure the signals being received by filaments 34 or ablation energy sent to filaments 34 results in an infinite number of possible combinations of filaments for detecting electrical activity during mapping procedures and for applying energy during an ablation procedure.

By controlling the amount of insulation that is removed from the filaments 34 that comprise braided conductive member 28, the surface area of the braid that is in contact with a blood vessel wall can also be controlled. This in turn will allow control of the impedance presented to an ablation energy generator, for example, generator 4. In addition, selectively removing the insulation can provide a predetermined or controllable profile of the ablation energy delivered to the tissue.

The above description illustrates how insulation may be removed from a filaments 34. Alternatively, the same features and advantages can be achieved by adding insulation to filaments 34. For example, filaments 34 may be bare wire and insulation can be added to them.

Individual control of the electrical signals received from filaments 34 allows catheter 10 to be used for bipolar (differential or between filament) type mapping as well as unipolar (one filament with respect to a reference) type mapping.

Catheter 10 may also have, as illustrated in FIGS. 2 and 3, a reference electrode 13 mounted on shaft 12 so that reference electrode 13 is located outside the heart during unipolar mapping operations.

Radiopaque markers can also be provided for use in electrode orientation and identification.

One skilled in the art will appreciate all of the insulation can be removed from filaments 34 to create a large ablation electrode.

Although a complete catheter steerable structure has been illustrated, the invention can also be adapted so that inner tubular member 22 is a catheter shaft, guide wire, or a hollow tubular structure for introduction of saline, contrast media, heparin or other medicines, or introduction of guidewires, or the like.

Temperature Sensing

A temperature sensor or sensors, such as, but not limited to, one or more thermocouples may be attached to braided conductive member 28 for temperature sensing during ablation procedures. A plurality of thermocouples may also be woven into the braided conductive member 28. An individual temperature sensor could be provided for each of the filaments 34 that comprise braided conductive member 28. Alternatively, braided conductive member 28 can be constructed of one or more temperature sensors themselves.

Figure 8:
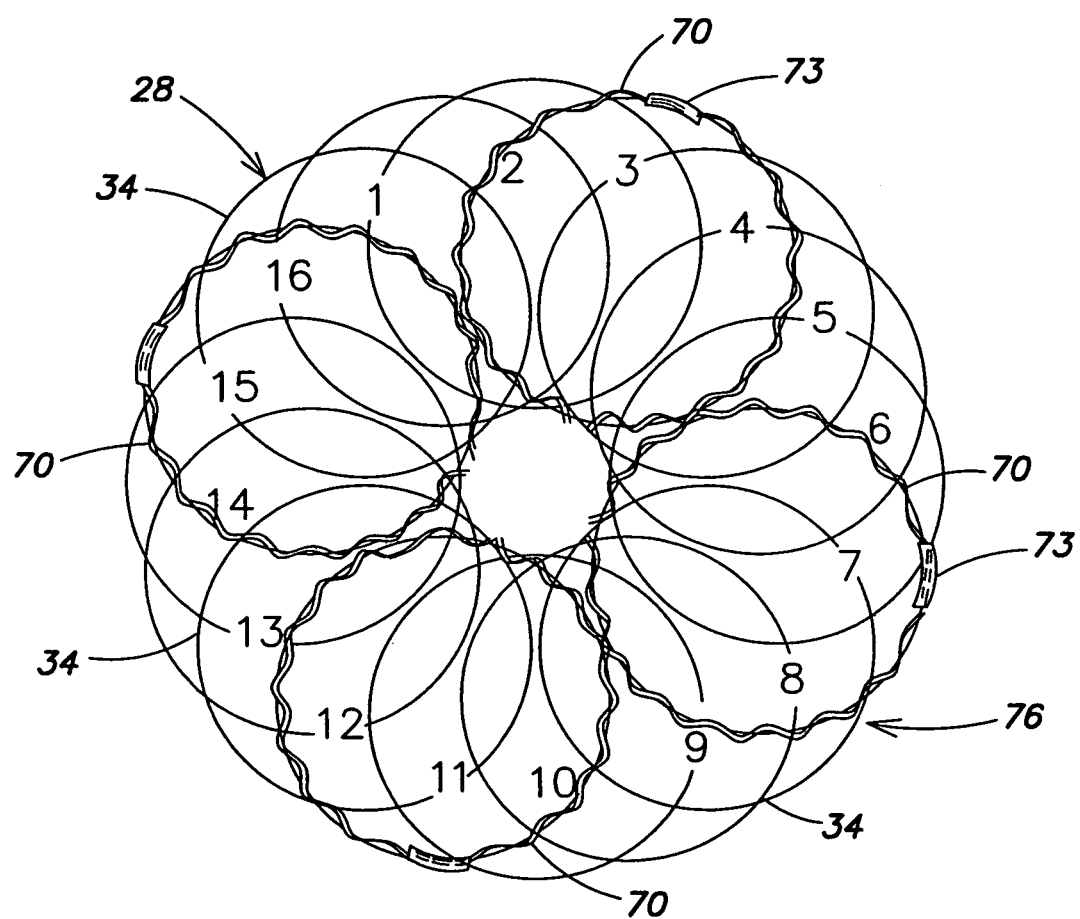
FIGS. 8-11 illustrate, among other things, temperature sensing in the present invention.
Figure 9:
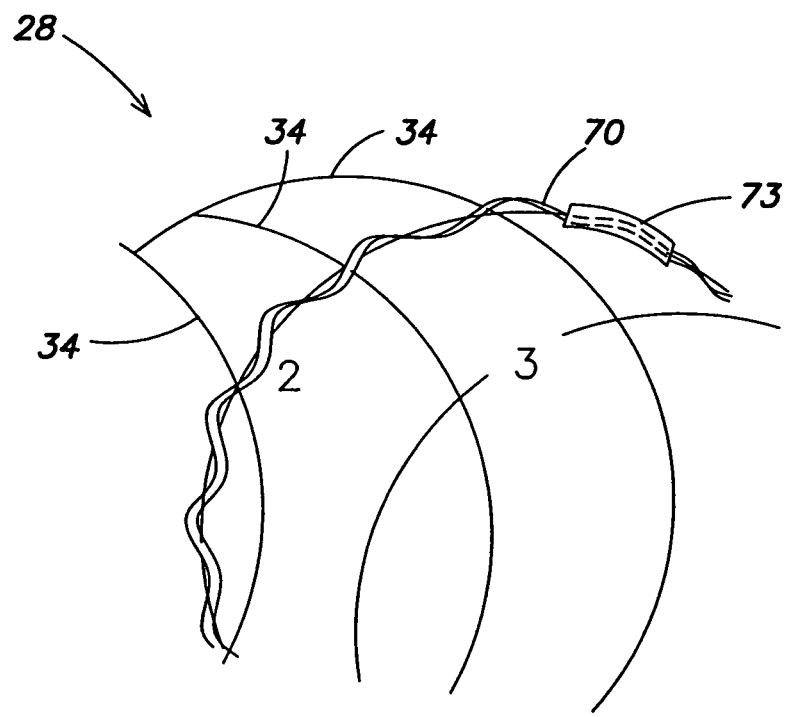

FIG. 8 illustrates braided conductive member 28 in its fully expanded or deployed configuration. Braided conductive member 28 forms a disk when fully expanded. In the embodiment illustrated in FIG. 8, there are sixteen filaments 34 that make up braided conductive member 28.

Temperature monitoring or control can be incorporated into braided conductive member 28, for example, by placing temperature sensors (such as thermocouples, thermistors, etc.) on the expanded braided conductive member 28 such that they are located on the distally facing ablative ring formed when braided conductive member 28 is in its fully expanded configuration. "Temperature monitoring" refers to temperature reporting and display for physician interaction. "Temperature control" refers to the capability of adding an algorithm in a feedback loop to titrate power based on temperature readings from the temperature sensors disposed on braided conductive member 28. Temperature sensors can provide a means of temperature control provided the segment of the ablative ring associated with each sensor is independently controllable (e.g., electrically isolated from other regions of the mesh). For example, control can be achieved by dividing the ablative structure into electrically independent sectors, each with a temperature sensor, or alternatively, each with a mechanism to measure impedance in order to facilitate power titration. The ablative structure may be divided into electrically independent sectors so as to provide zone control. The provision of such sectors can be used to provide power control to various sections of braided conductive member 28.

As illustrated in FIG. 8, four temperature sensors 70 are provided on braided conductive member 28. As noted previously, since the individual filaments 34 in braided conductive member 28 are insulated from each other, a number of independent sectors may be provided. A sector may include one or more filaments 34. During ablation procedures, energy can be applied to one or more of the filaments 34 in any combination desired depending upon the goals of the ablation procedure. A temperature sensor could be provided on each filament 34 of braided conductive member 28 or shared among one or more filaments. In mapping applications, one or more of the filaments 34 can be grouped together for purposes of measuring electrical activity. These sectoring functions can be provided in controller 8.

Figure 10:
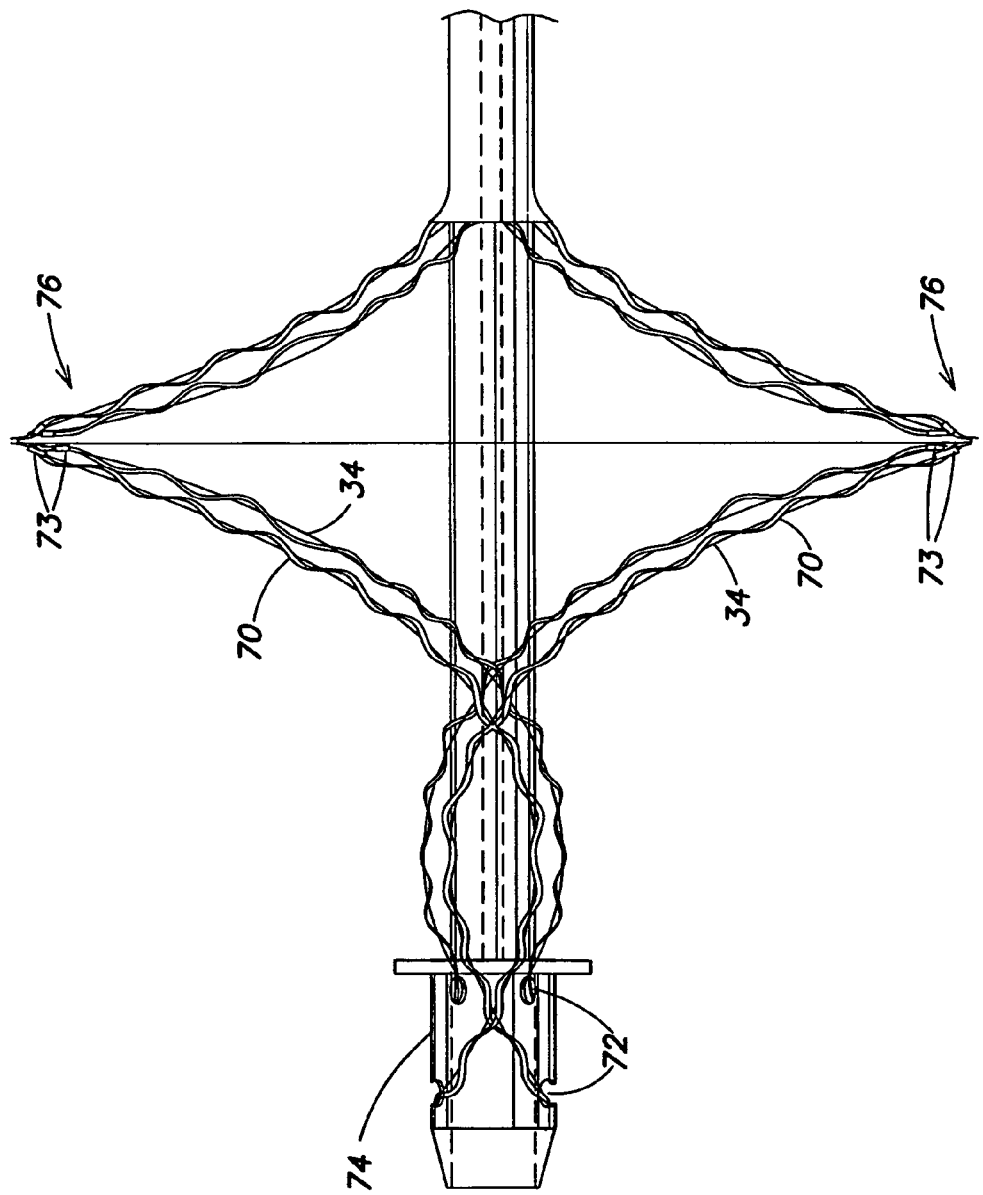

FIG. 10 illustrates a side view of braided conductive member 28 including temperature sensors 70. As shown in FIG. 10, temperature sensors 70 emerge from four holes 72. Each hole 72 is disposed in one quadrant of anchor 74. The temperature sensors 70 are bonded to the outside edge 76 of braided conductive member 28. Temperature sensors 70 may be isolated by a small piece of polyimide tubing 73 around them and then bonded in place to the filaments. The temperature sensors 70 may be woven and twisted into braided conductive member 28 or they can be bonded on a side-by-side or parallel manner with the filaments 34.

There are several methods of implementing electrically independent sectors. In one embodiment, the wires are preferably stripped of their insulative coating in the region forming the ablative ring (when expanded). However, sufficient insulation may be left on the wires in order to prevent interconnection when in the expanded state. Alternatively, adjacent mesh wires can be permitted to touch in their stripped region, but can be separated into groups by fully insulated (unshipped) wires imposed, for example, every 3 or 5 wires apart (the number of wires does not limit this invention), thus forming sectors of independently controllable zones. Each zone can have its own temperature sensor. The wires can be "bundled" (or independently attached) to independent outputs of an ablation energy generator. RF energy can then be titrated in its application to each zone by switching power on and off (and applying power to other zones during the 'off period') or by modulating voltage or current to the zone (in the case of independent controllers). In either case, the temperature inputs from the temperature sensors can be used in a standard feedback algorithm to control the power delivery.

Figure 10A:
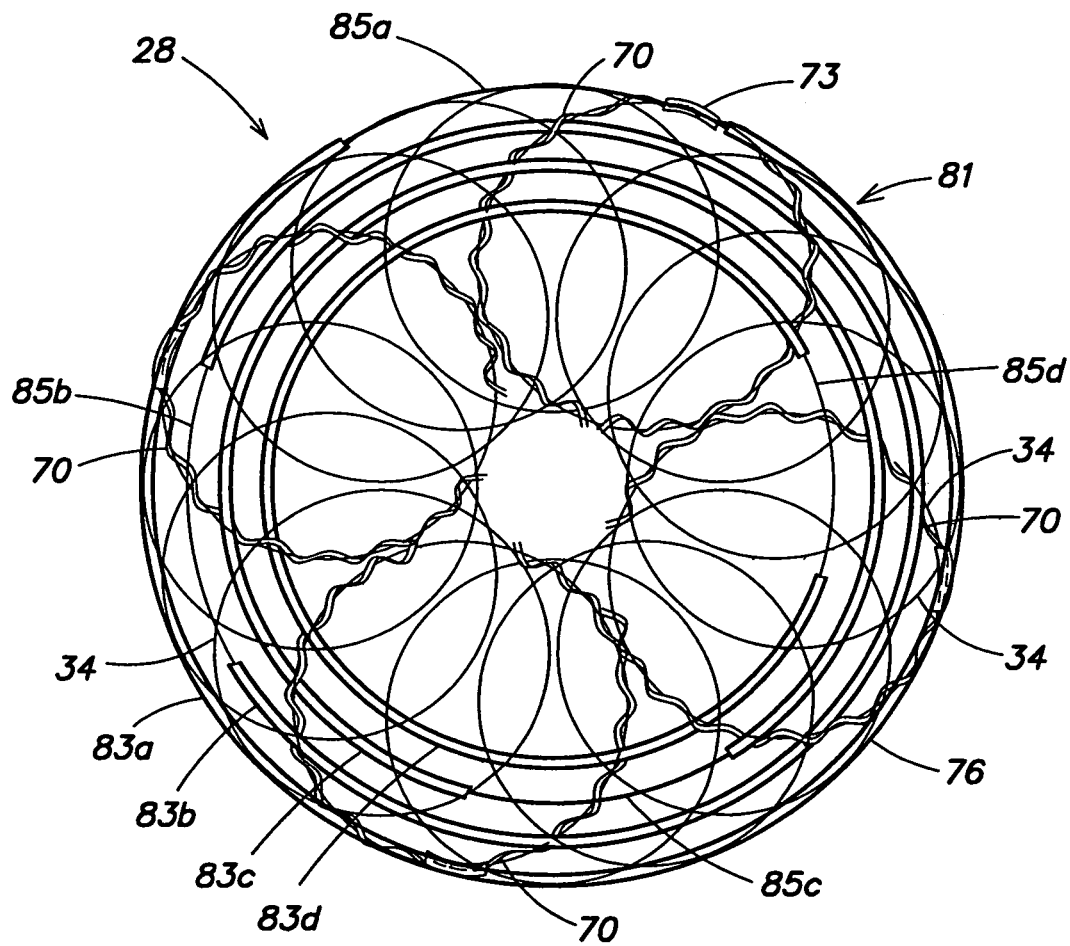

Alternatively, as illustrated in FIG. 10A, braided conductive member 28 may be used to support a ribbon-like structure which is separated into discrete sectors. As shown in FIG. 10A, the ribbon-like structure 81 may be, for example, a pleated copper flat wire that, as braided conductive member 28 expands, unfolds into an annular ring. Each of the wires 83a-83d lie in the same plane. Although four wires are illustrated in FIG. 10A, structure 81 may include any number of wires depending upon the application and desired performance. Each of wires 83a-83d is insulated. Insulation may then be removed from each wire to create different sectors 85a-85d. Alternatively, each of wires 83a-83d may be uninsulated and insulation may be added to create different sectors. The different sectors provide an ablative zone comprised of independently controllable wires 83a-83d. Temperature sensors 70 may be mounted on the individual wires, and filaments 34 may be connected to respective wires 83a-83d to provide independent control of energy to each individual sector. One skilled in the art will appreciate that each of wires 83a-83d can have multiple sectors formed by removing insulation in various locations and that numerous combinations of sectors 85a-85d and wires 83a-83d forming ribbon-like structure 81 can be obtained.

FIGS. 11A-D illustrate further exemplary configurations that include a temperature sensor within braided conductive member 28. In each configuration, the temperature sensor is formed using one thermocouple wire 75 and one filament 34 of braided conductive member 28, which are coupled via a junction 77 to form a thermocouple 71. Advantageously, since only one dedicated thermocouple wire is required to form the thermocouple 71, the size of a braided conductive member 28 in FIGS. 11A-C may be smaller than it would be if a pair of dedicated thermocouple wires were required to form each thermocouple 71. In addition, the filament 34 that is used to form a portion of the thermocouple 71 may be used for ablation and/or mapping purposes while signals indicative of temperature are supplied by the thermocbuple 71.

Figure 11B:
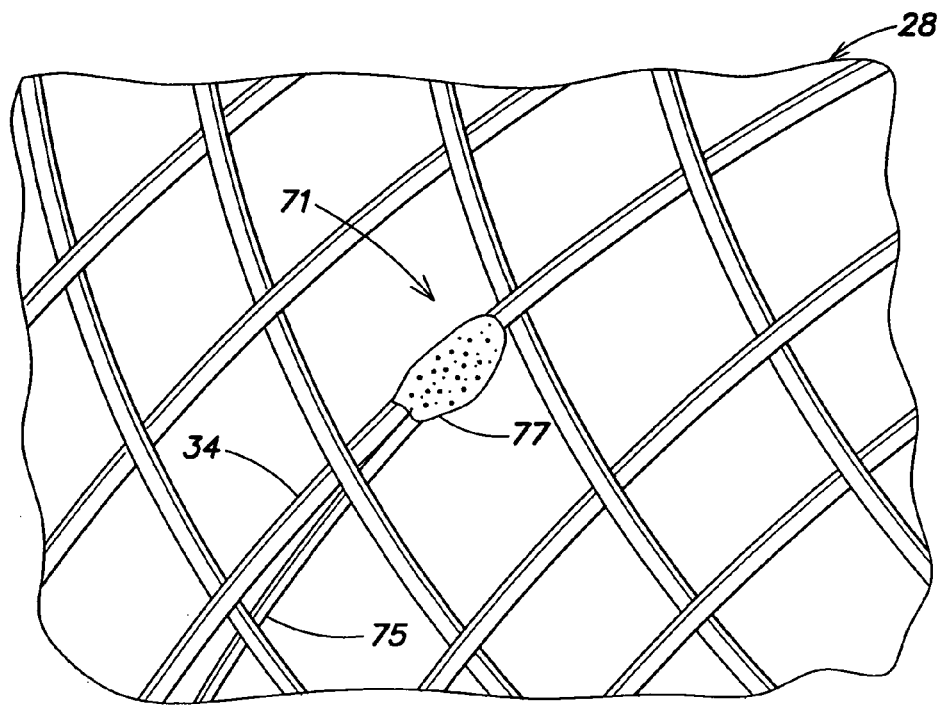

In the configurations described in connection with FIGS. 11B-D, the temperature sensors may be formed on an outward-facing or exterior portion of the braided conductive member 28, or an inward-facing or interior portion of the braided conductive member 28. FIG. 11A illustrates an exterior portion 84a and an interior portion 84b of a braided conductive member 28, which is concentrically disposed about inner member 22 and anchored to the first sheath 24 and second sheath 26, respectively. It should be appreciated that temperature sensors disposed on an exterior portion 84a of the braided conductive member 28 may be formed anywhere along the length or circumference of the braided conductive member 28 on an exterior portion thereof. Similarly, temperature sensors disposed on an interior portion 84b of the braided conductive member 28 may be formed anywhere along the length or circumference of the braided conductive member 28 on an interior portion thereof.

Figure 11C:
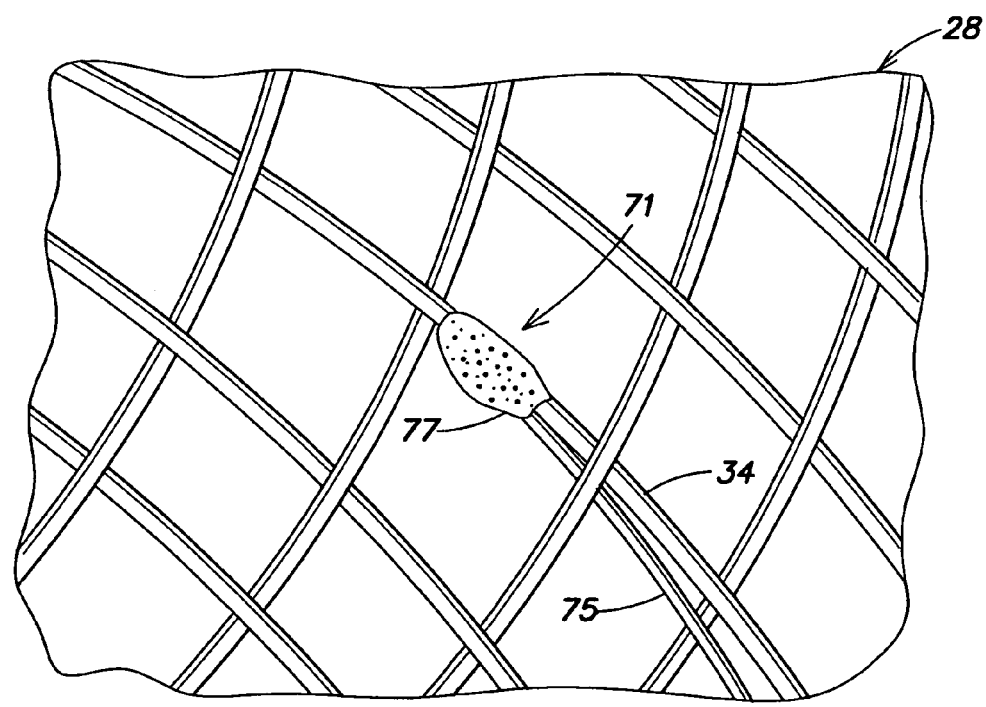

FIG. 11B illustrates an exterior portion of the braided conductive member 28, while FIG. 11C illustrates a interior portion of the braided conductive member 28. According to one implementation of the thermocouple 71, the junction 77 may be formed on an exterior portion of the braided conductive member 28, as shown in FIG. 11B. Thus, the junction 77 may be formed on a portion of the braided conductive member 28 that may come into contact with tissue during an electrophysiology procedure. According to another implementation of the thermocouple 71, the junction 77 may be formed on an interior portion of the braided conductive member 28, as shown in FIG. 11C. Thus, the junction 77 may be formed on a surface of the braided conductive member 28 that does not come into contact with tissue during an electrophysiology procedure. In each case, the junction 77 may be formed so as to avoid interference with filaments of the braided conductive member 28 during deployment of the braided conductive member 28.

Figure 11D:
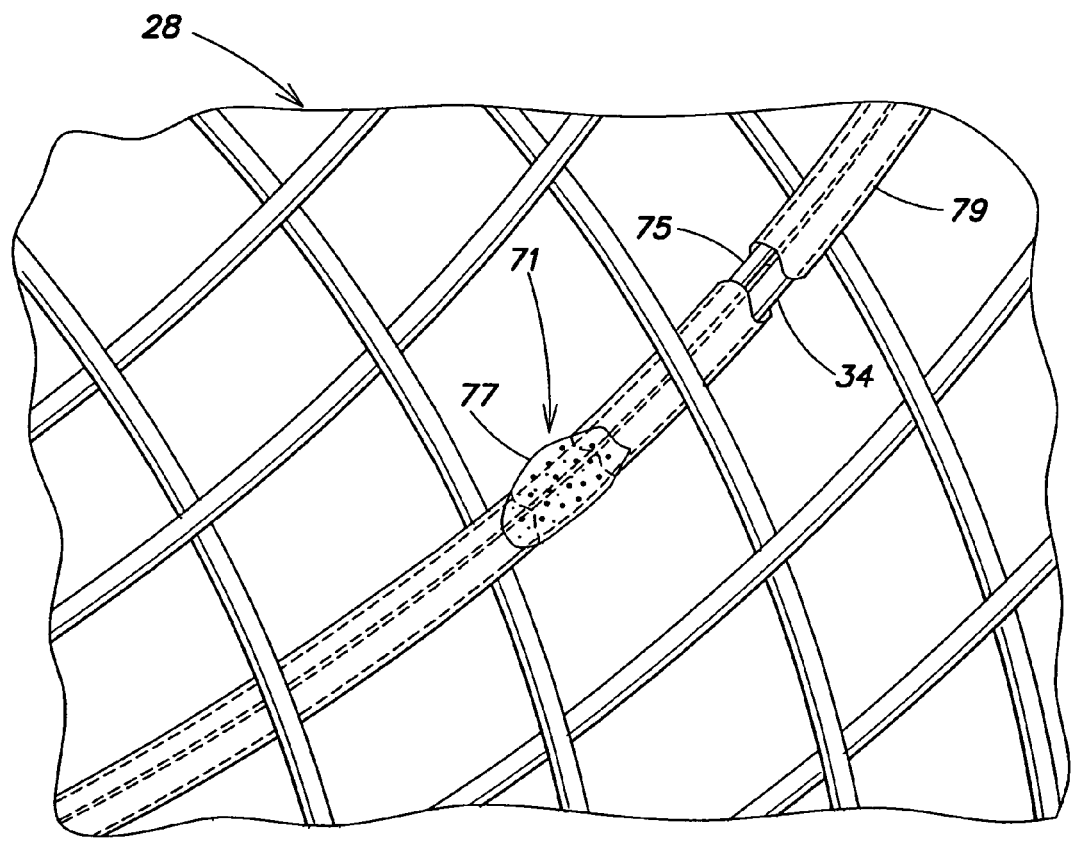

FIG. 11D illustrates an configuration in which the filament 34 and the thermocouple wire 75 that form thermocouple 71 are coupled together via a sheath 79 to form a unitary strand that may be woven into braided conductive member 28. Junction 77 is formed on a portion of the filament 34 and the thermocouple wire 75 that is not covered by sheath 79, and where insulation of the filament 34 and the thermocouple wire 75 has been removed. Thus, the filament 34 and the thermocouple wire 75 are in electrical contact at the location of junction 77. It should be appreciated that while the sheath 79 is shown as removed around an entire circumference thereof at the location of junction 77, alternatively, only a portion of the circumference of the sheath 79 may be removed. Thus, the junction 77 may be formed on an exterior-facing portion of the braided conductive member 28, an interior-facing portion of the braided conductive member 28, or both. The configuration of FIG. 11D secures the thermocouple wire 75 from movement during deployment of the braided conductive member. In addition, by coupling the filament 34 and the thermocouple wire 75 along their length, the size of the thermocouple 71 may be minimized.

It should be appreciated that while sheath 79 that couples filament 34 and thermocouple wire 75 is shown as having a generally tubular shape, many other implementations are possible. For example, the sheath may be constructed as tubes that are connected along adjacent surfaces thereof such that a cross-section of the tube would have a figure-eight configuration. Other exemplary alternative configurations are a spiral configuration and an oval tubular configuration. It should be appreciated that the sheath need not be continuous and may be perforated or cover only portions of the filament 34 and the thermocouple wire 75. It should further be appreciated that the sheath 79 may have a solid core with the filament 34 and thermocouple wire 75 molded within the sheath 79.

Thermocouple wire 75 and filament 34 may be formed of different electrically conductive materials such that an electric current will flow between the wires when the thermocouple wire 75 and filament 34 are at different temperatures. In one example, thermocouple wire 75 may be formed of constantan and filament 34 may be formed of copper-beryllium, with the beryllium comprising approximately 2% of the filament composition. However, it should be appreciated that a number of alternative materials may be used for thermocouple wire 75 and filament 34.

Junction 77 may be formed on an uninsulated portion of filament 34 and thermocouple wire 75. In one example, filament 34 and thermocouple wire 77 are at least partially insulated, but are uninsulated where the filament 34 and thermocouple wire 75 contact junction 77. Thus, if junction 77 is formed on an exterior portion of the braided conductive member 28, the portions of filament 34 and thermocouple wire 75 that face the interior of braided conductive member 28 and are opposite junction 77 may be insulated. Correspondingly, if junction 77 is formed on an interior portion of the braided conductive member 28, the portions of filament 34 and thermocouple wire 75 that face the exterior of braided conductive member 28 and are opposite junction 77 may be insulated.

Junction 77 may be formed of a material that is electrically conductive and capable of forming a mechanical bond between the thermocouple wire 75 and filament 34. According to one example, the junction 77 is formed of a metal such as silver solder. According to another example, the junction 77 is formed of a material resistant to corrosion. If it is not resistant to corrosion, a junction may corrode when it is exposed to blood or another electrolyte. This corrosion could weaken the mechanical strength of the bond and serve as a source of electrical noise that can interfere with electrogram signal quality. According to one example, an electrically conductive epoxy such as silver epoxy, which is resistant to corrosion, may be used to form a junction 77.

It should be appreciated that although the above features of an epoxy junction and a single dedicated thermocouple wire may be advantageously employed together, these features may also be employed separately. It should further be appreciated that although only a single temperature sensor is shown on braided conductive member 28 in FIGS. 11B-D, a plurality of temperature sensors may be included on the braided conductive member 28 as described in the foregoing discussion of temperature sensing. The features described in connection with FIGS. 11B-D may be combined with other catheter features described herein to provide temperature sensing capabilities to a catheter.

Steering

Figure 13:
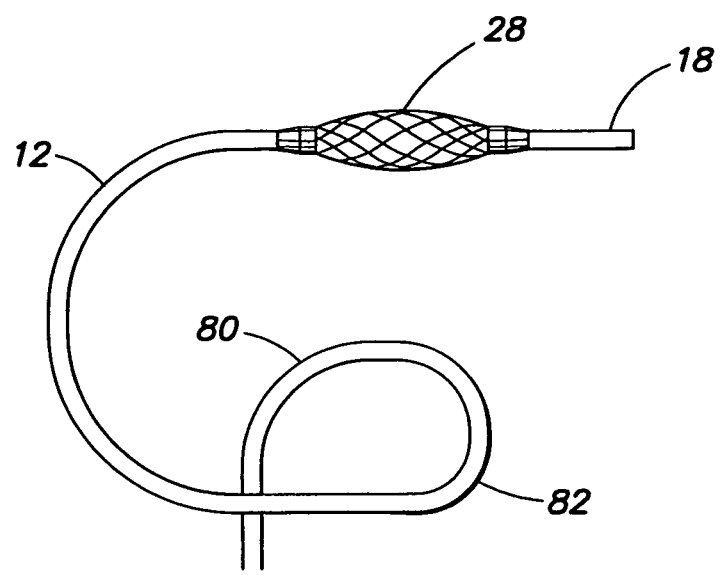

Reference is now made to FIGS. 12-13 which illustrate aspects of the steering capabilities of the present invention. As illustrated in FIGS. 1-2, catheter 10 is capable of being steered using control handle 14. In particular, FIG. 1 illustrates steering where the steering pivot or knuckle is disposed on catheter shaft 12 in a region that is distal to the braided conductive member 28.

FIG. 12A illustrates catheter 10 wherein the pivot point or steering knuckle is disposed proximal to braided conductive member 28.

FIG. 12B illustrates catheter 10 having the capability of providing steering knuckles both proximal and distal to braided conductive member 28.

FIGS. 1-2, and 12A-12B illustrate two dimensional or single plane type steering. The catheter of the present invention can also be used in connection with a three dimensional steering mechanism. For example, using the control handle in the incorporated by reference '852 patent, the catheter can be manipulated into a three-dimensional "lasso-like" shape, particularly at the distal end of the catheter. As shown in FIG. 13, the catheter can have a primary curve 80 in one plane and then a second curve 82 in another plane at an angle to the first plane. With this configuration, the catheter can provide increased access to difficult to reach anatomical structures. For example, a target site for a mapping or ablation operation may be internal to a blood vessel. Thus, the increased steering capability can allow easier access into the target blood vessel. In addition, the additional dimension of steering can allow for better placement of braided conductive member 28 during an ablation or mapping procedure. Catheter 10 can be inserted into a site using the steering capabilities provided by primary curve 80. Thereafter, using the secondary curve 82, braided conductive member 28 can be tilted into another plane for better orientation or contact with the target site.

Conductive Member Configurations And Materials

Reference is now made to FIGS. 14-17 which figures illustrate other configurations of braided conductive member 28. As has been described above and will be described in more detail, braided conductive member 28 can include from one to 300 or more filaments. The filaments may vary from very fine wires having small diameters or cross-sectional areas to large wires having relatively large diameters or cross-sectional areas.

Figure 14:
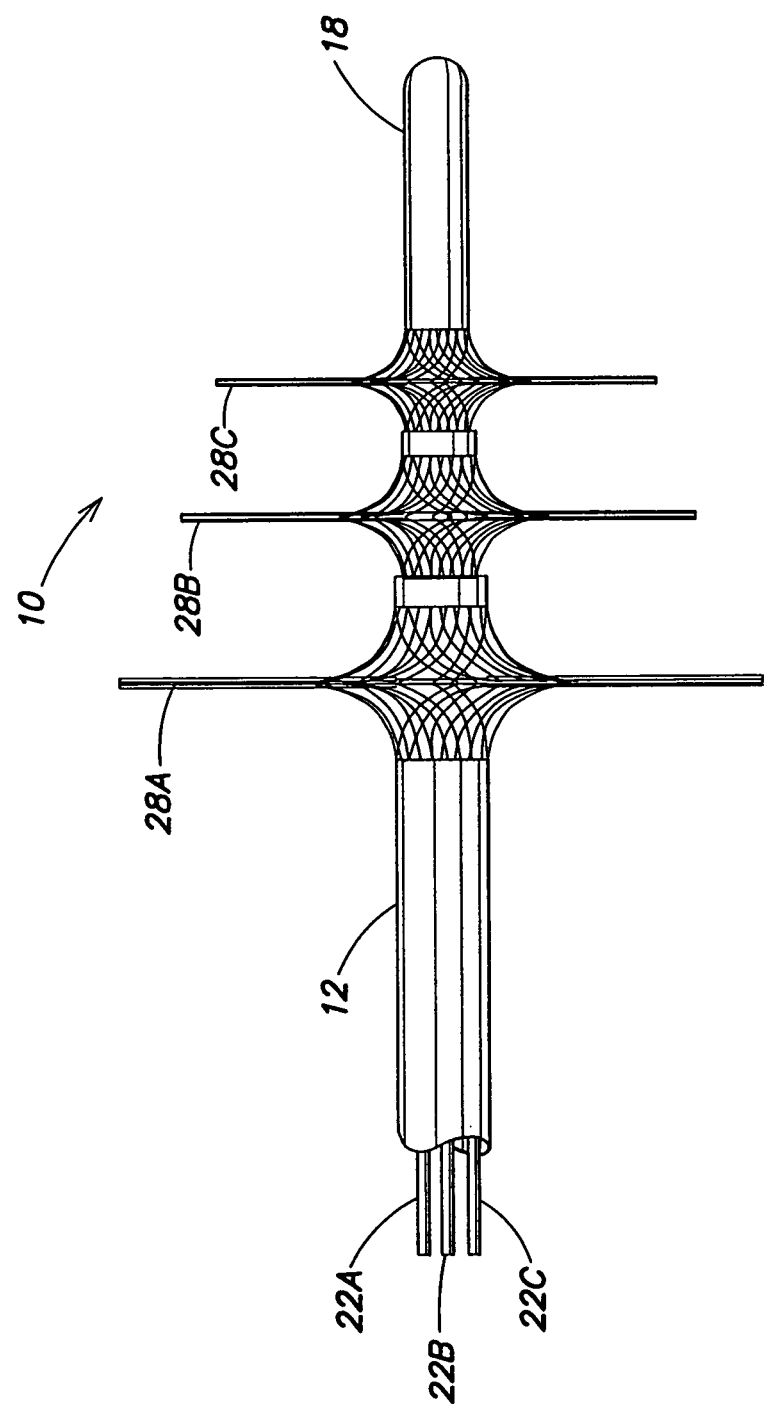
FIGS. 14-17 illustrate further embodiments of the braided conductive member.

FIG. 14 illustrates the use of more than one braided conductive member 28 as the distal end of catheter 10. As shown in FIG. 14, three braided conductive members 28A, 28B, and 28C are provided at the distal end of catheter 10. Braided conductive members 28A, 28B, and 29C may be, in their expanded conditions, the same size or different sizes. Each of the braided conductive members 28A, 28B, and 28C can be expanded or contracted independently in the manner illustrated in FIGS. 1-4 via independent control shafts 22A, 22B, and 22C. The use of multiple braided conductive members provides several advantages. Rather than having to estimate or guess as to the size of the blood vessel prior to starting a mapping or ablation procedure, if braided conductive members 28A, 28B, and 28C are of different expanded diameters, than sizing can be done in vivo during a procedure. In addition, one of the braided conductive members can be used for ablation and another of the braided conductive members can be used for mapping. This allows for quickly checking the effectiveness of an ablation procedure.

Figure 15A:
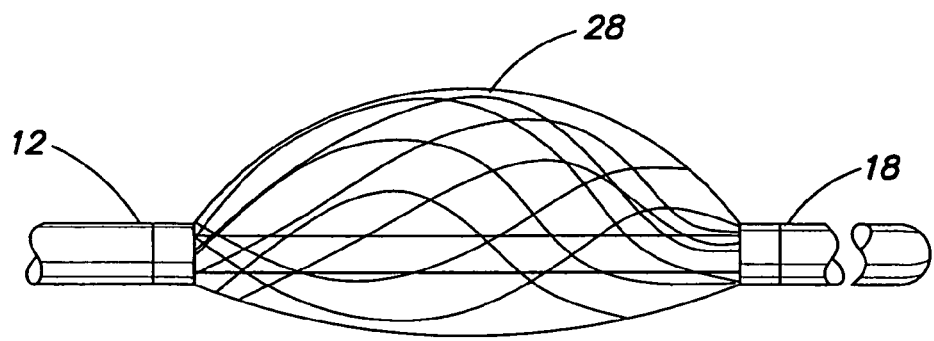
Figure 15B:
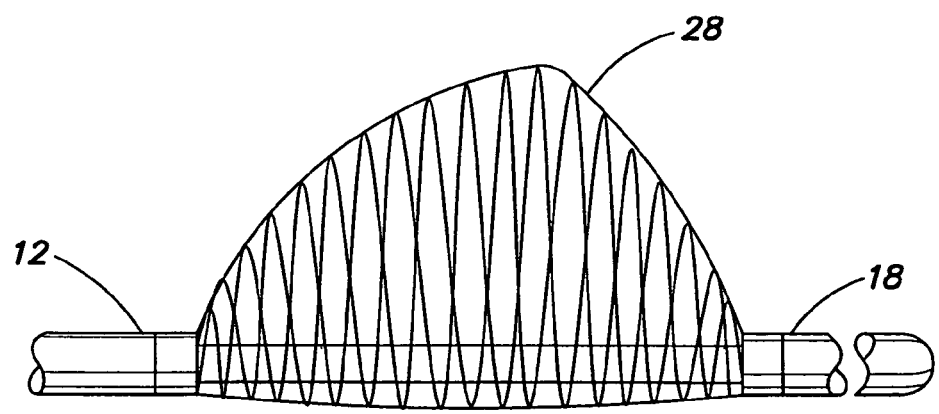

Reference is now made to FIGS. 15A and 15B, which figures illustrate other shapes of braided conductive member 28. As described up to this point, braided conductive member 28 is generally symmetrical and coaxial with respect to catheter shaft 12. However, certain anatomical structures may have complex three-dimensional shapes that are not easily approximated by a geometrically symmetrical mapping or ablation structure. One example of this type of structure occurs at the CS ostium. To successfully contact these types of anatomical structures, braided conductive member 28 can be "preformed" to a close approximation of that anatomy, and yet still be flexible enough to adapt to variations found in specific patients. Alternatively, braided conductive member 28 can be "preformed" to a close approximation of that anatomy, and be of sufficient strength (as by choice of materials, configuration, etc.) to force the tissue to conform to variations found in specific patients. For example FIG. 15A illustrates braided conductive member 28 disposed about shaft 12 in an off-center or non concentric manner. In addition, braided conductive member 28 may also be constructed so that the parameter of the braided conductive member in its expanded configuration has a non-circular edge so as to improve tissue contact around the parameter of the braided conductive member. FIG. 15B illustrates an example of this type of configuration where the braided conductive member 28 is both off center or non concentric with respect to catheter shaft 12 and also, in its deployed or expanded configuration, has an asymmetric shape. The eccentricity of braided conductive member 28 with respect to the shaft and the asymmetric deployed configurations can be produced by providing additional structural supports in braided conductive member 28, for example, such as by adding nitinol, ribbon wire, and so on. In addition, varying the winding pitch or individual filament size or placement or deforming selective filaments in braided conductive member 28 or any other means known to those skilled in the art may be used.

Figure 16A:
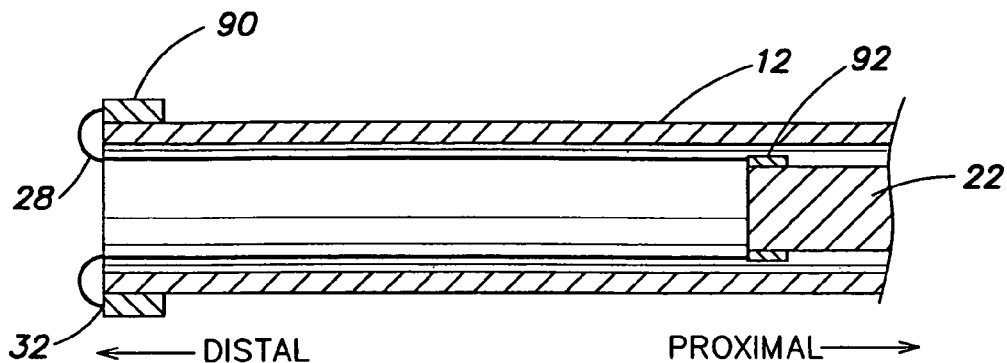
Figure 16B:
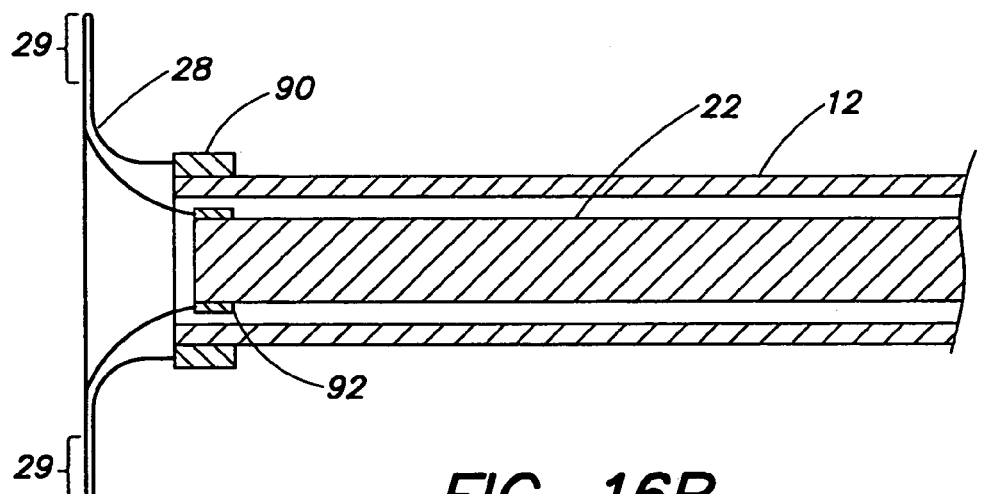
Figure 16C:
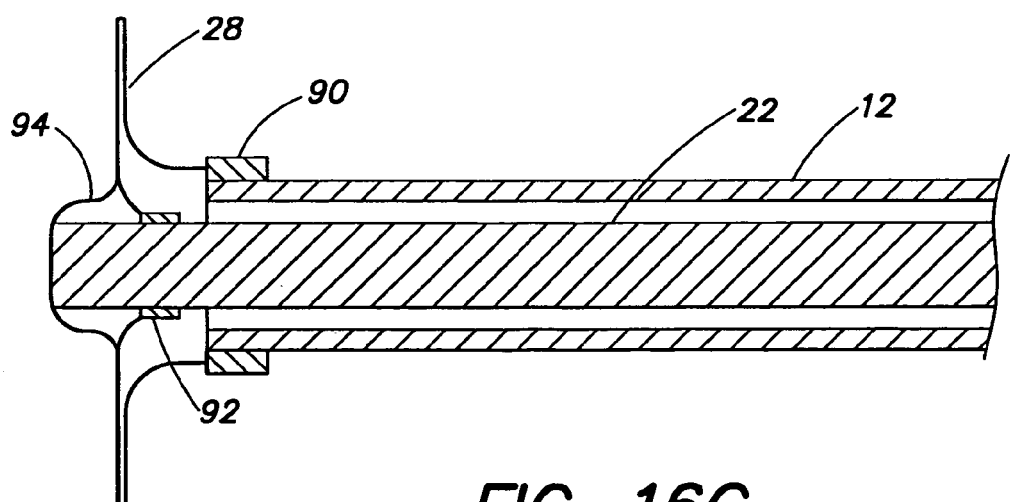

FIGS. 16A-16C illustrate another configuration of braided conductive member 28 and catheter 10. As illustrated in FIGS. 16A-16C, the distal tip section of catheter 10 has been removed and braided conductive member 28 is disposed at the distal end of catheter 10. One end of braided conductive member 28 is anchored to catheter shaft 12 using an anchor band 90 that clamps the end 32 of braided conductive member 28 to catheter shaft 12. The other end of braided conductive member 28 is clamped to an activating shaft such as shaft 22 using another anchor band 92. FIG. 16A illustrates braided conductive member 28 in its undeployed configuration. As shaft 22 is moved distally, braided conductive member 28 emerges or everts from shaft 12. As shown in FIG. 16B, braided conductive member 28 has reached its fully deployed diameter and an annular tissue contact zone 29 can be placed against an ostium or other anatomical structure. As illustrated in FIG. 16C, further distal movement of shaft 22 can be used to create a concentric locating region 94 that can help to provide for concentric placement within an ostium of a pulmonary vein, for example. Concentric locating region 94 may be formed by selective variations in the winding density of filaments 34 in braided conductive member 28, preferential predeformation of the filaments, additional eversion of braided conductive member 28 from shaft 12, or by other means known to those skilled in the art.

Figure 17:
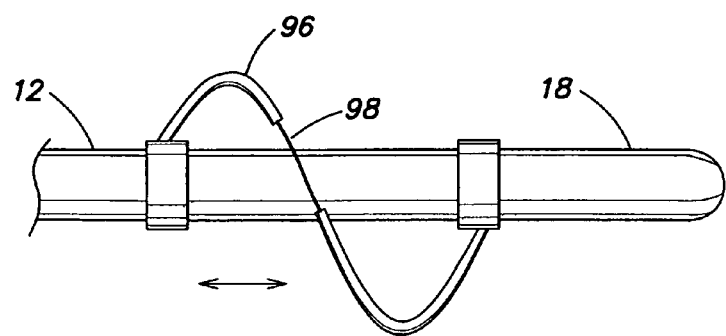

Reference is now made to FIG. 17, which figure illustrates a further embodiment of braided conductive member 28. As illustrated in FIG. 17, braided conductive member 28 is composed of one or several large wires 96 rather than a multiplicity of smaller diameter wires. The wire or wires can be moved between the expanded and unexpanded positions in the same manner as illustrated in FIG. 1. In addition, a region 98 may be provided in which the insulation has been removed for mapping or ablation procedures. The single wire or "corkscrew" configuration provides several advantages. First, the wire or wires do not cross each other and therefore there is only a single winding direction required for manufacture. In addition, the risk of thrombogenicity may be reduced because there is a smaller area of the blood vessel being blocked. In addition, the connections between the ends of the large wire and the control shafts may be simplified.

The catheter 10 of the present invention can be coated with a number of coatings that can enhance the operating properties of braided conductive member 28. The coatings can be applied by any of a number of techniques and the coatings may include a wide range of polymers and other materials.

Braided conductive member 28 can be coated to reduce its coefficient of friction, thus reducing the possibility of thrombi adhesion to the braided conductive member as well as the possibility of vascular or atrial damage. These coatings can be combined with the insulation on the filaments that make up braided conductive member 28, these coatings can be included in the insulation itself, or the coatings can be applied on top of the insulation. Examples of coating materials that can be used to improve the lubricity of the catheter include PD slick available from Phelps Dodge Corporation, Ag, Tin, BN. These materials can be applied by an ion beam assisted deposition ("IBAD") technique developed by, for example, Amp Corporation.

Braided conductive member 28 can also be coated to increase or decrease its thermal conduction which can improve the safety or efficacy of the braided conductive member 28. This may be achieved by incorporating thermally conductive elements into the electrical insulation of the filaments that make up braided conductive member 28 or as an added coating to the assembly. Alternatively, thermally insulating elements may be incorporated into the electrical insulation of the filaments that make up braided conductive member 28 or added as a coating to the assembly. Polymer mixing, IBAD, or similar technology could be used to add Ag, Pt, Pd, Au, Ir, Cobalt, and others into the insulation or to coat braided conductive member 28.

Radioopaque coatings or markers can also be used to provide a reference point for orientation of braided conductive member 28 when viewed during fluoroscopic imaging. The materials that provide radiopacity including, for example, Au, Pt, Ir, and other known to those skilled in the art. These materials may be incorporated and used as coatings as described above.

Antithrombogenic coatings, such as heparin and BH, can also be applied to braided conductive member 28 to reduce thrombogenicity to prevent blood aggregation on braided conductive member 28. These coatings can be applied by dipping or spraying, for example.

As noted above, the filament 34 of braided conductive member 28 may be constructed of metal wire materials. These materials may be, for example, MP35N, nitinol, or stainless steel. Filaments 34 may also be composites of these materials in combination with a core of another material such as silver or platinum. The combination of a highly conductive electrical core material with another material forming the shell of the wire allows the mechanical properties of the shell material to be combined with the electrical conductivity of the core material to achieve better and/or selectable performance. The choice and percentage of core material used in combination with the choice and percentage of shell material used can be selected based on the desired performance characteristics and mechanical/electrical properties desired for a particular application. According to one implementation, the core material and shell material may be covalently bonded together.

Irrigation

Figure 18:
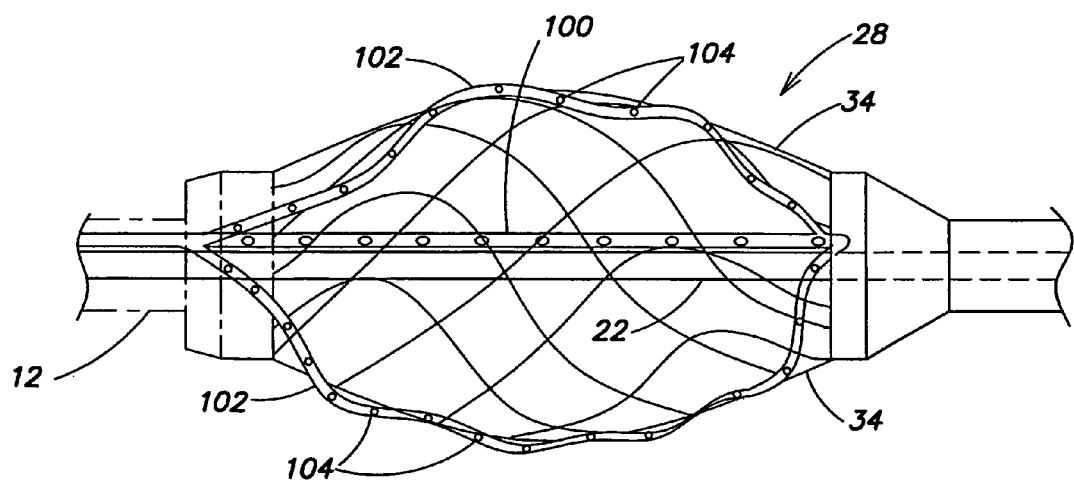
FIGS. 18-19 illustrate the use of irrigation in connection with the present invention.

It is known that for a given electrode side and tissue contact area, the size of a lesion created by radiofrequency (RF) energy is a function of the RF power level and the exposure time. At higher powers, however, the exposure time can be limited by an increase in impedance that occurs when the temperature at the electrode-tissue interface approaches a 100° C. One way of maintaining the temperature less than or equal to this limit is to irrigate the ablation electrode with saline to provide convective cooling so as to control the electrode-tissue interface temperature and thereby prevent an increase in impedance. Accordingly, irrigation of braided conductive member 28 and the tissue site at which a lesion is to be created can be provided in the present invention. FIG. 18 illustrates the use of an irrigation manifold within braided conductive member 28. An irrigation manifold 100 is disposed along shaft 22 inside braided conductive member 28. Irrigation manifold 100 may be one or more polyimide tubes. Within braided conductive member 28, the irrigation manifold splits into a number of smaller tubes 102 that are woven into braided conductive member 28 along a respective filament 34. A series of holes 104 may be provided in each of the tubes 102. These holes can be oriented in any number of ways to target a specific site or portion of braided conductive member 28 for irrigation. Irrigation manifold 100 runs through catheter shaft 12 and may be connected to an irrigation delivery device outside the patient used to inject an irrigation fluid, such as saline, for example, such as during an ablation procedure.

The irrigation system can also be used to deliver a contrast fluid for verifying location or changes in vessel diameter. For example, a contrast medium may be perfused prior to ablation and then after an ablation procedure to verify that there have been no changes in the blood vessel diameter. The contrast medium can also be used during mapping procedures to verify placement of braided conductive member 28. In either ablation or mapping procedures, antithrombogenic fluids, such as heparin can also be perfused to reduce thrombogenicity.

Figure 19:
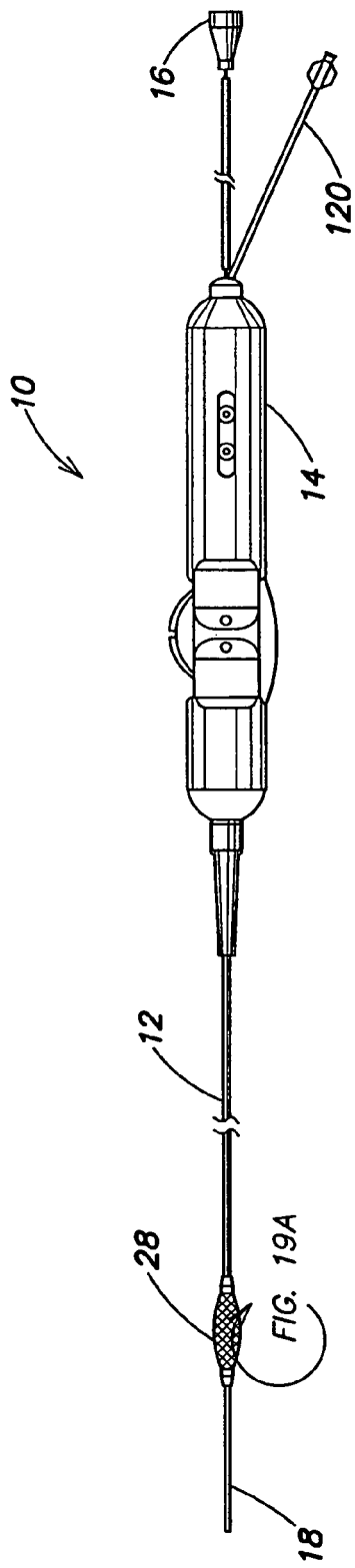
Figure 19A:
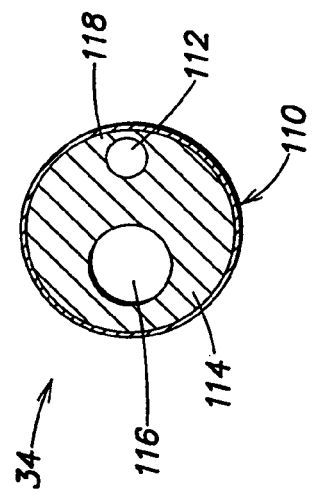

FIG. 19 illustrates another way of providing perfusion/irrigation in catheter 10. As illustrated in FIG. 19, the filaments 34 that comprise braided conductive member 28 are composed of a composite wire 110. The composite wire 110 includes an electrically conductive wire 112 that is used for delivering ablation energy in an ablation procedure or for detecting electrical activity during a mapping procedure. Electrical wire 112 is contained within a lumen 114 that also contains a perfusion lumen 116. Perfusion lumen 116 is used to deliver irrigation fluid or a contrast fluid as described in connection with FIG. 18. Once braided conductive member 28 has been constructed with composite wire 110, the insulation 118 surrounding wire filament 112 can be stripped away to form an electrode surface. Holes can then be provided into perfusion lumen 116 to then allow perfusion at targeted sites along the electrode surface. As with the embodiment illustrated in FIG. 18, the perfusion lumens can be connected together to form a manifold which manifold can then be connected to, for example, perfusion tube 120 and connected to a fluid delivery device.

Shrouds

The use of a shroud or shrouds to cover at least a portion of braided conductive member 28 can be beneficial in several ways. The shroud can add protection to braided conductive member 28 during insertion and removal of catheter 10. A shroud can also be used to form or shape braided conductive member 28 when in its deployed state. Shrouds may also reduce the risk of thrombi formation on braided conductive member 28 by reducing the area of filament and the number of filament crossings exposed to blood contact. This can be particularly beneficial at the ends 30 and 32 of braided conductive member 28. The density of filaments at ends 30 and 32 is greatest and the ends can therefore be prone to blood aggregation. The shrouds can be composed of latex balloon material or any material that would be resistant to thrombi formation durable enough to survive insertion through an introducer system, and would not reduce the mobility of braided conductive member 28. The shrouds can also be composed of an RF transparent material that would allow RF energy to pass through the shroud. If an RF transparent material is used, complete encapsulation of braided conductive member 28 is possible.

A shroud or shrouds may also be useful when irrigation or perfusion is used, since the shrouds can act to direct irrigation or contrast fluid to a target region.

Figure 20A:
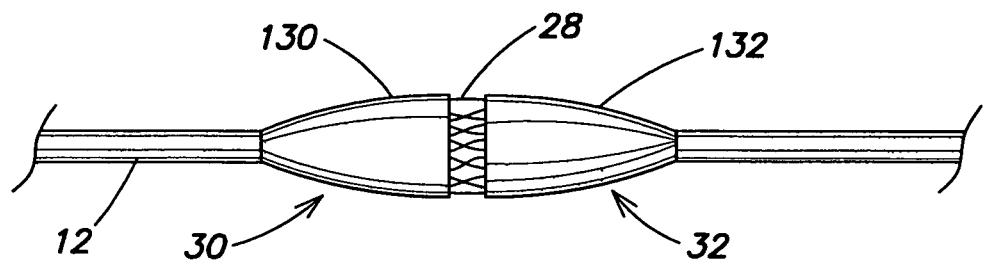
FIGS. 20A-20E illustrate the use of shrouds in the present invention.
Figure 20B:
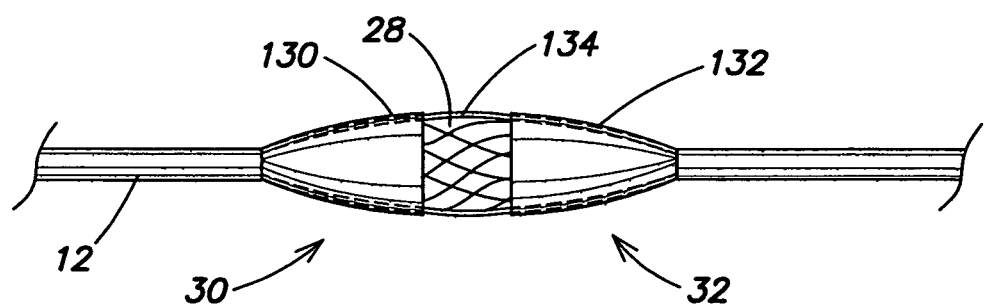

FIGS. 20A-20E illustrate various examples of shrouds that may be used in the present invention. FIG. 20A illustrates shrouds 130 and 132 disposed over end regions 30 and 32, respectively, of braided conductive member 28. This configuration can be useful in preventing coagulation of blood at the ends of braided conductive member 28. FIG. 20B illustrates shrouds 130 and 132 used in conjunction with an internal shroud 134 contained inside braided conductive member 28. In addition to preventing blood coagulation in regions 30 and 32, the embodiment illustrated in FIG. 20B also prevents blood from entering braided conductive member 28.

Figure 20C:
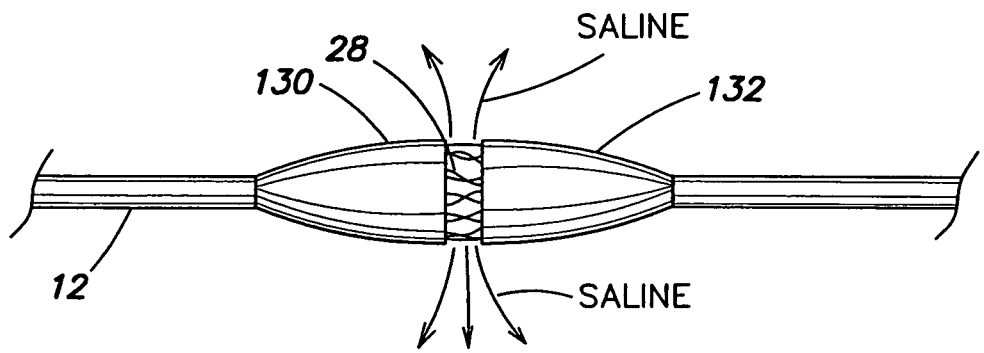

FIG. 20C illustrates shrouds 130 and 132 being used to direct and irrigation fluid or contrast medium along the circumferential edge of braided conductive member 28. In the embodiment illustrated in FIG. 20C, perfusion can be provided as illustrated in FIGS. 18 and 19.

Figure 20D:
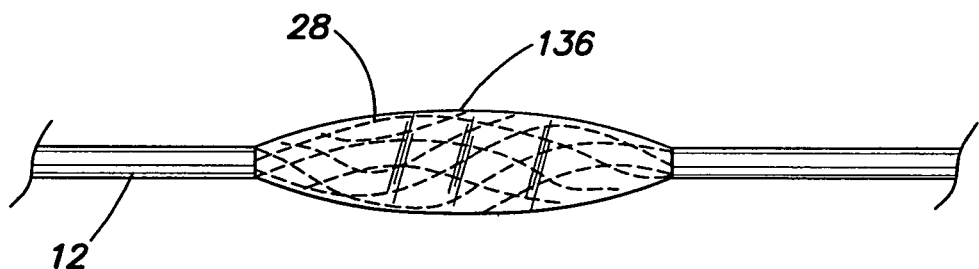

FIG. 20D illustrates the use of an external shroud that covers braided conductive member 28. Shroud 136 completely encases braided conductive member 28 and thereby eliminates blood contact with braided conductive member 28. Shroud 136 may be constructed of a flexible yet ablation-energy transparent material so that, when used in an ablation procedure, braided conductive member 28 can still deliver energy to a targeted ablation site.

Figure 20E:
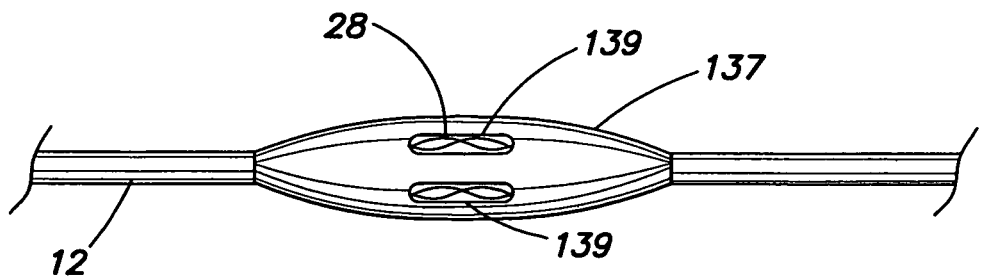

FIG. 20E also illustrates an external shroud 137 encasing braided conductive member 28. Shroud 137 may also be constructed of a flexible yet ablation-energy transparent material. Openings 139 may be provided in shroud 137 to allow the portions of braided conductive member 28 that are exposed by the opening to come into contact with tissue. Openings 139 may be elliptical, circular, circumferential, etc.

Guiding Sheaths

There may be times during ablation or mapping procedures when catheter 10 is passing through difficult or tortuous vasculature. During these times, it may be helpful to have a guiding sheath through which to pass catheter 10 so as to allow easier passage through the patient's vasculature.

Figure 21:
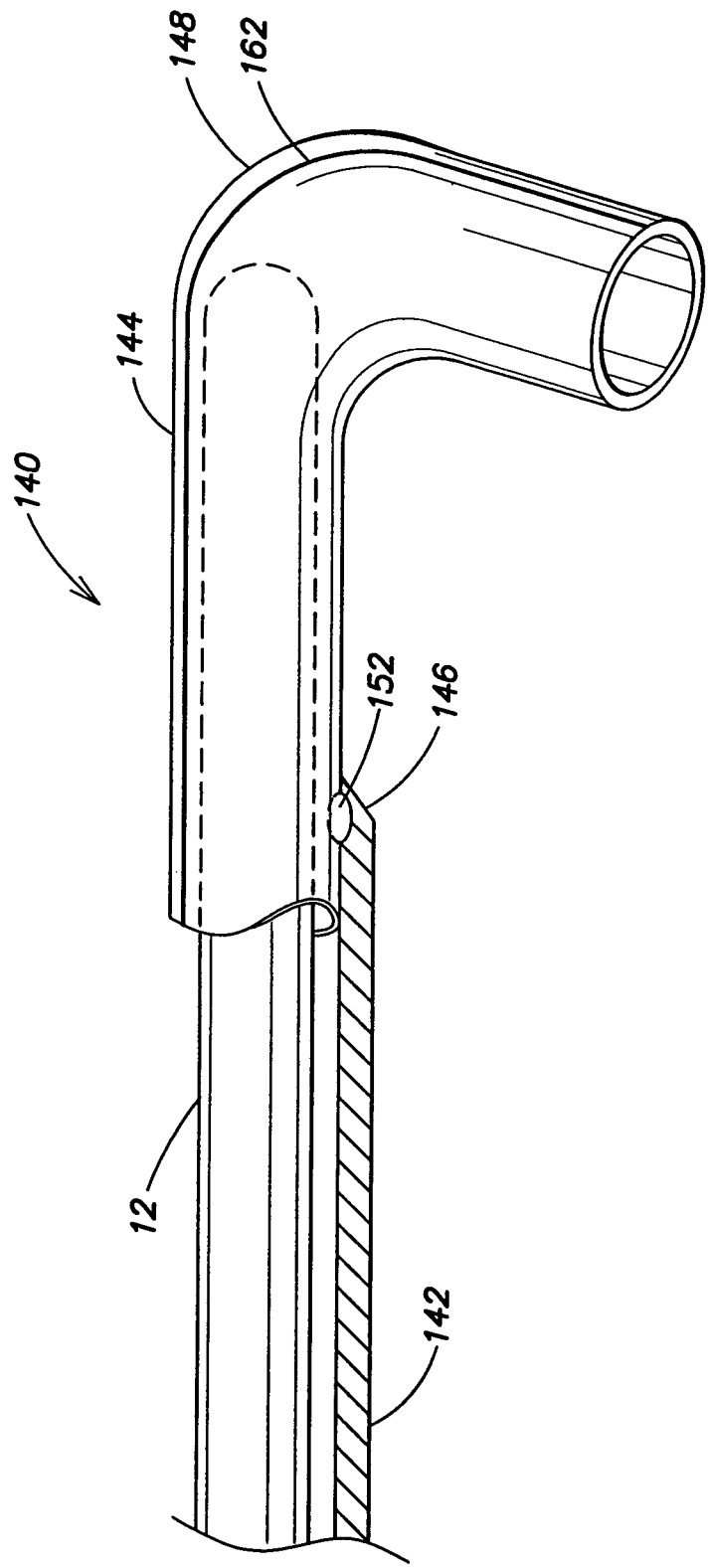
FIG. 21 illustrates a guiding sheath that may be used in connection with the present invention.

FIG. 21 illustrates one example of a guiding sheath that may be used in connection with catheter 10. As illustrated in FIG. 21, the guiding sheath 140 includes a longitudinal member 142. Longitudinal member 142 may be constructed of a material rigid enough to be pushed next to catheter shaft 12 as the catheter is threaded through the vasculature. In one example, longitudinal member 142 may be stainless steel. Longitudinal member 142 is attached to a sheath 144 disposed at the distal end 146 of longitudinal member 142. The split sheath 144 may have one or more predetermined curves 148 that are compatible with the shapes of particular blood vessels (arteries or veins) that catheter 10 needs to pass through. Split sheath 144 may extend proximally along longitude at member 142. For example, sheath 144 and longitudinal member 142 may be bonded together for a length of up to 20 or 30 centimeters to allow easier passage through the patient's blood vessels. Sheath 144 includes a predetermined region 162 that extends longitudinally along sheath 144. Region 162 may be, for example, a seam, that allows sheath 144 to be split open so that the guiding sheath 140 can be pulled back and peeled off catheter shaft 12 in order to remove the sheath.

In another embodiment, longitudinal member 142 may be a hypotube or the like having an opening 152 at distal end 146 that communicates with the interior of sheath 144. In this embodiment, longitudinal member 142 can be used to inject irrigation fluid such as saline or a contrast medium for purposes of cooling, flushing, or visualization.

Methods of Use

Figure 22:
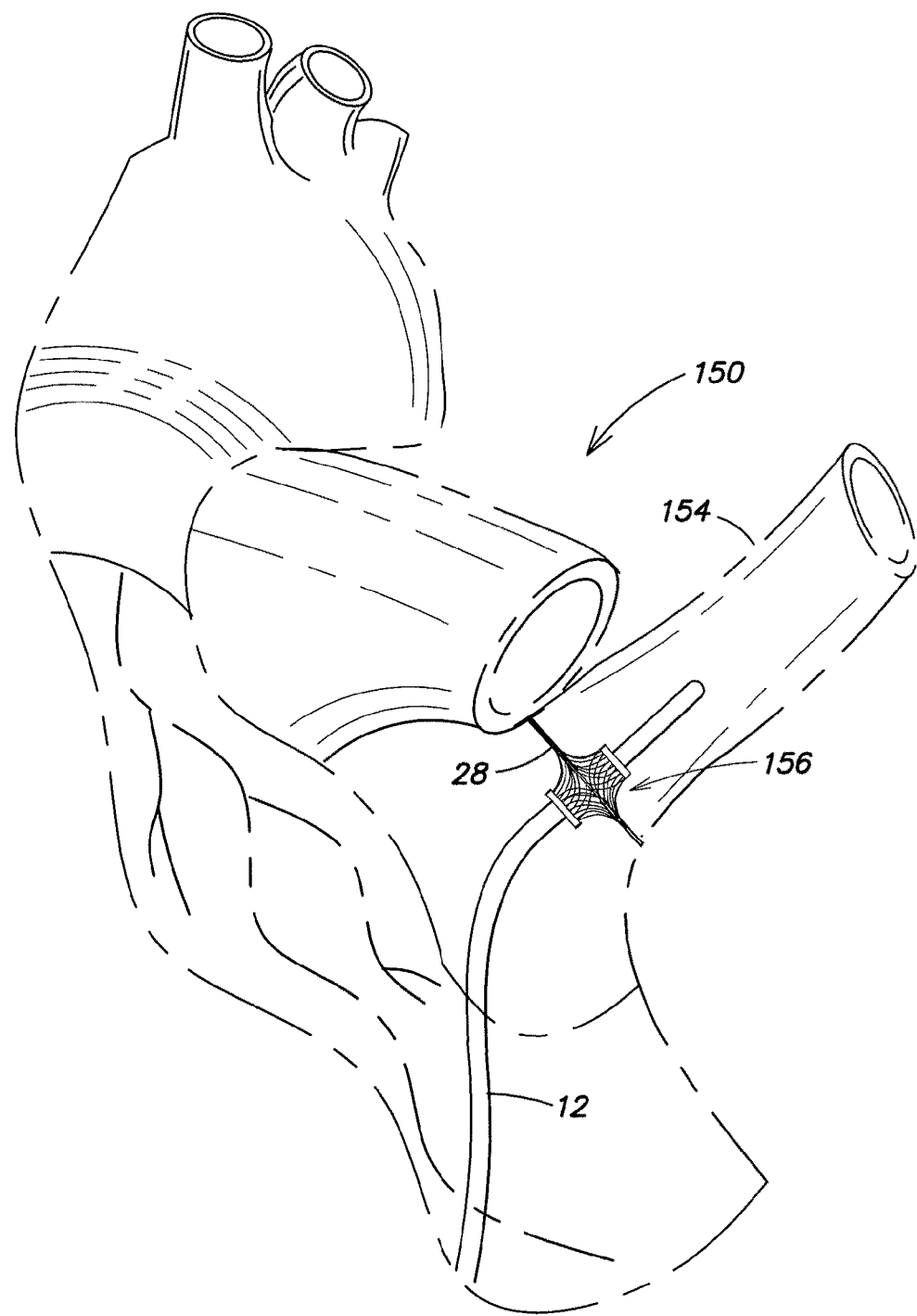
FIGS. 22-24 illustrate methods of using the present invention.
Figure 23:
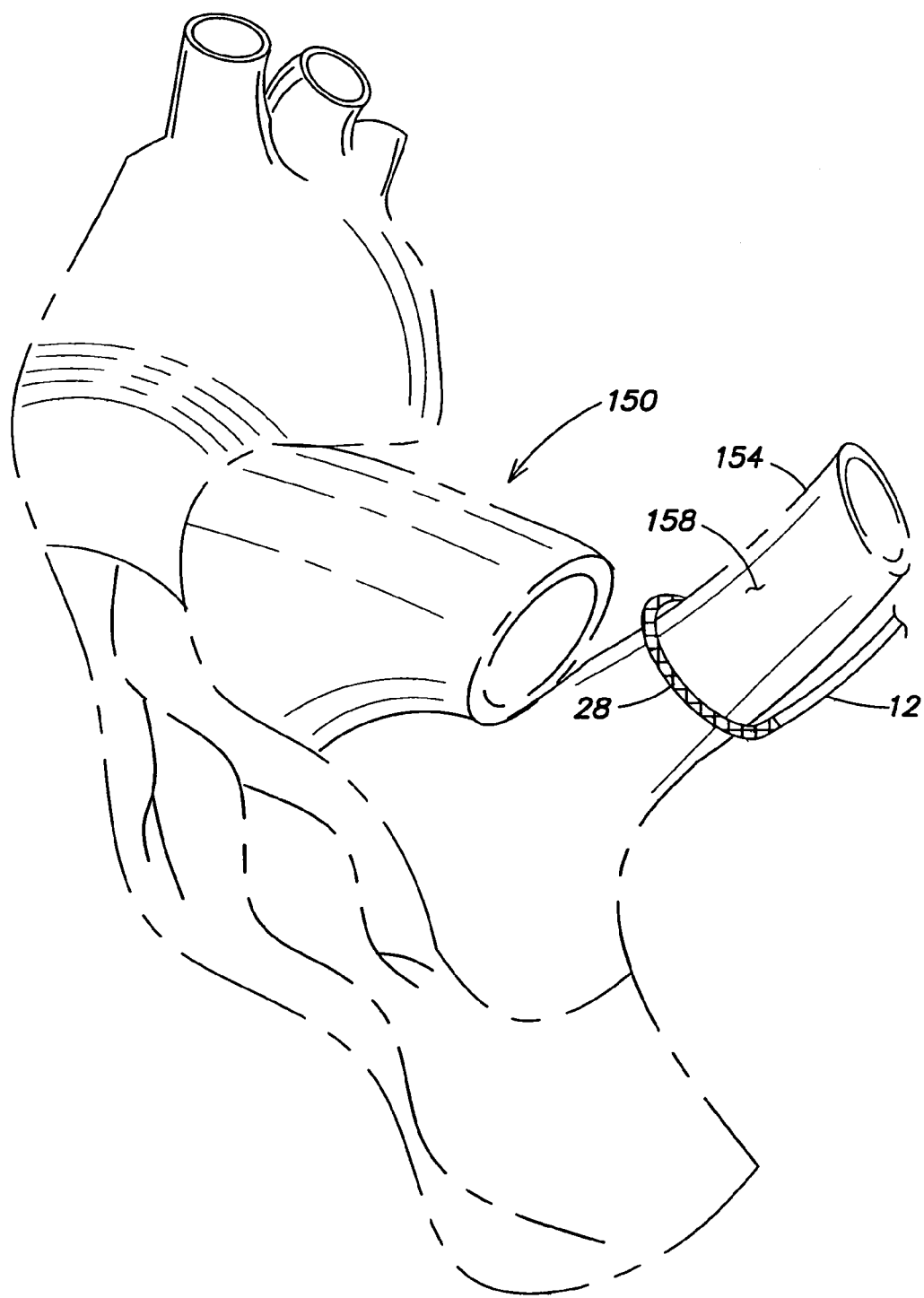
Figure 24:
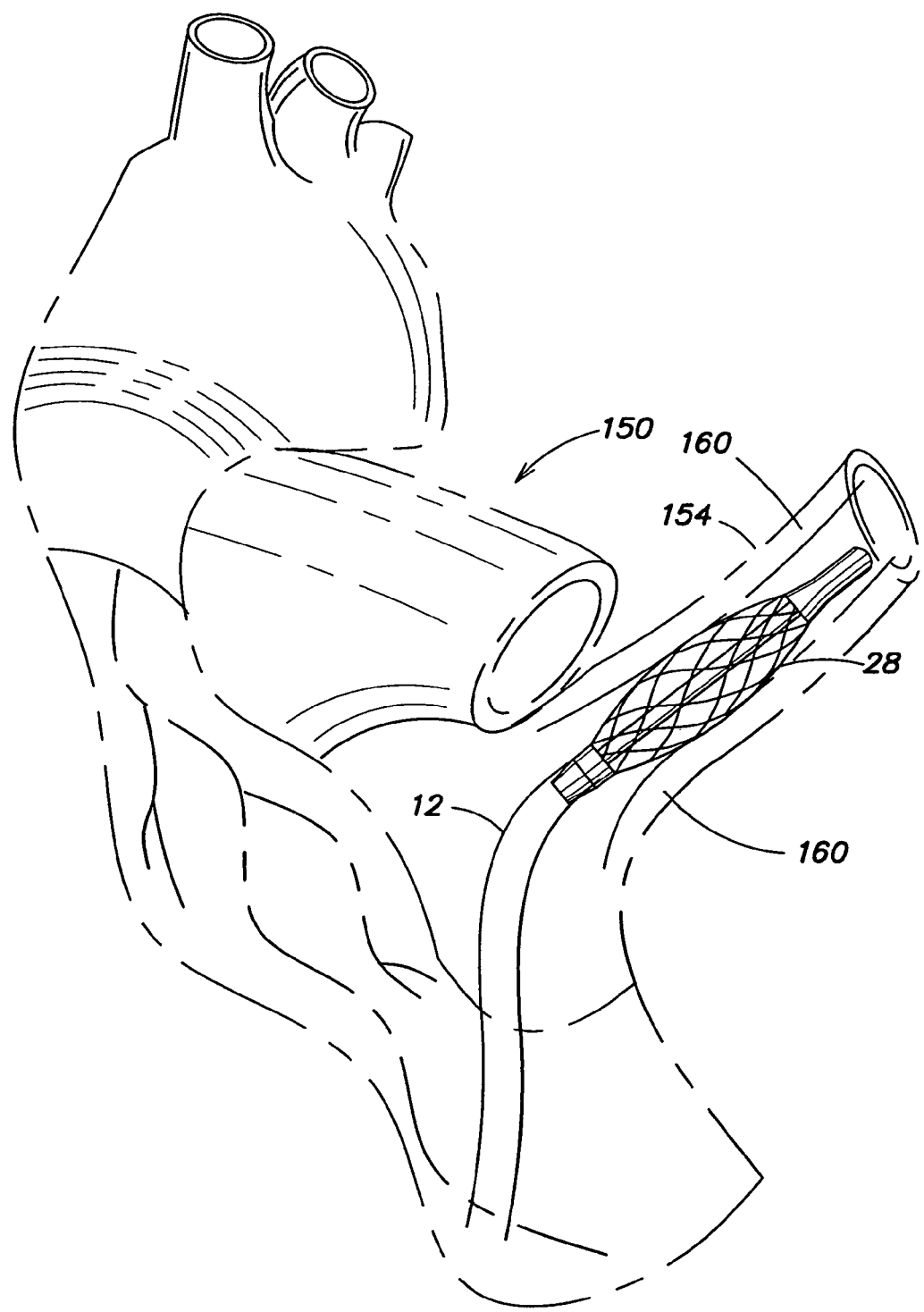

Reference is now made to FIGS. 22, 23, and 24, which figures illustrate how the catheter of the present invention may be used in endocardial and epicardial applications.

Referring to FIG. 22, this figure illustrates an endocardial ablation procedure. In this procedure, catheter shaft 12 is introduced into a patient's heart 150. Appropriate imaging guidance (direct visual assessment, camera port, fluoroscopy, echocardiographic, magnetic resonance, etc.) can be used. FIG. 22 in particular illustrates catheter shaft 12 being placed in the left atrium of the patient's heart. Once catheter shaft 12 reaches the patient's left atrium, it may then be introduced through an ostium of a pulmonary vein 154. As illustrated, braided conductive member 28 is then expanded to its deployed position, where, in the illustrated embodiment, braided conductive member 28 forms a disk. Catheter shaft 12 then advanced further into pulmonary vein 154 until the distal side 156 of braided conductive member 28 makes contact with the ostium of pulmonary vein 154. External pressure may be applied along catheter shaft 12 to achieve the desired level of contact of braided conductive member 28 with the ostium tissue. Energy is then applied to the ostium tissue in contact with braided conductive member 28 to create an annular lesion at or near the ostium. The energy used may be RF (radiofrequency), DC, microwave, ultrasonic, cryothermal, optical, etc.

Reference is now made to FIG. 23, which figure illustrates an epicardial ablation procedure. As illustrated in FIG. 23, catheter shaft 12 is introduced into a patient's thoracic cavity and directed to pulmonary vein 154. Catheter 10 may be introduced through a trocar port or intraoperatively during open chest surgery Using a steering mechanism, preformed shape, or other means by which to make contact between braided conductive member 128 and the outer surface 158 of pulmonary vein 154, braided conductive member 28 is brought into contact with the outer surface 158 of pulmonary vein 154. Appropriate imaging guidance (direct visual assessment, camera port, fluoroscopy, echocardiographic, magnetic resonance, etc.) can be used. As illustrated in FIG. 23, in this procedure, braided conductive member 28 remains in its undeployed or unexpanded condition. External pressure maybe applied to achieve contact between braided conductive member 28 with pulmonary vein 154. Once the desired contact with the outer surface 158 of pulmonary vein 154 is attained, ablation energy is applied to surface 158 via braided conductive member 28 using, for example, RF, DC, ultrasound, microwave, cryothermal, or optical energy. Thereafter, braided conductive member 28 may be moved around the circumference of pulmonary vein 154, and the ablation procedure repeated. This procedure may be used to create, for example, an annular lesion at or near the ostium.

Use of the illustrated endocardial or epicardial procedures may be easier and faster than using a single "point" electrode since a complete annular lesion may be created in one application of RF energy.

Reference is now made to FIG. 24 which figure illustrates an endocardial mapping procedure. In the procedure illustrated in FIG. 24, catheter shaft 12 is introduced into pulmonary vein 154 in the manner described in connection with FIG. 22. Once braided conductive 28 has reached a desired location within pulmonary vein 154, braided conductive member 28 is expanded as described in connection with, for example, FIGS. 2-5 until filaments 34 contact the inner wall 160 of pulmonary vein 154. Thereafter, electrical activity within pulmonary vein 154 may be detected, measured, and recorded by an external device connected to the filaments 34 of braided conductive member 28.

Access to the patient's heart can be accomplished via percutaneous, vascular, surgical (e.g. open-chest surgery), or transthoracic approaches for either endocardial or epicardial mapping and/or mapping and ablation procedures.

The present invention is thus able to provide an electrophysiology catheter capable of mapping and/or mapping and ablation operations. In addition, the catheter of the invention may be used to provide high density maps of a tissue region because electrocardiograms may be obtained from individual filaments 34 in braided conductive member 28 in either a bipolar or unipolar mode.

Furthermore, the shape of the electrode region can be adjusted by controlling the radial expansion of braided conductive member 28 so as to improve conformity with the patient's tissue or to provide a desired mapping or ablation profile. Alternatively, braided conductive member 28 may be fabricated of a material of sufficient flexural strength so that the tissue is preferentially conformed to match the expanded or partially expanded shape of the braided conductive member 28.

The catheter of the present invention may be used for mapping procedures, ablation procedures, and temperature measurement and control on the distal and/or proximal facing sides of braided conductive member 28 in its fully expanded positions as illustrated in, for example, FIG. 1. In addition, the catheter of the present invention can be used to perform "radial" mapping procedures, ablation procedures, and temperature measurement and control. That is, the outer circumferential edge 76, illustrated, for example, in FIG. 8, can be applied against an inner circumferential surface of a blood vessel.

Furthermore, being able to use the same catheter for both mapping and ablation procedures has the potential to reduce procedure time and reduce X-ray exposure.

The ability to expand braided conductive member 28 in an artery or vein against a tissue structure such as a freewall or ostium can provide good contact pressure for multiple electrodes and can provide an anatomical anchor for stability. Temperature sensors can be positioned definitively against the endocardium to provide good thermal conduction to the tissue. Lesions can be selectively produced at various sections around the circumference of braided conductive member 28 without having to reposition catheter 10. This can provide more accurate lesion placement within the artery or vein.

Braided conductive member 28, in its radially expanded position as illustrated in particular in FIGS. 1 and 8 is advantageous because, in these embodiments, it does not block the blood vessel during a mapping or ablation procedure, but allows blood flow through the braided conductive member thus allowing for longer mapping and/or ablation times, which can potentially improve accuracy of mapping and efficacy of lesion creation.

Handle Assembly

An exemplary implementation of handle 14 (FIG. 1) will now be described in connection with FIGS. 25-31. The handle configuration shown uses linear movement of the slide actuator 124 (FIG. 26), formed of slider 232 and slider grip 252, to selectively control the tension applied to pull cables 162a and 162b, which may for example control the radius of curvature of the distal end of the catheter. The handle configuration further uses rotational movement of the thumbwheel actuator 122 to selectively control the tension applied to pull cables 162c and 162d coupled thereto. These pull cables may control the orientation of the distal end of the catheter of the catheter relative to the longitudinal axis of the shaft 12.

Figure 25:
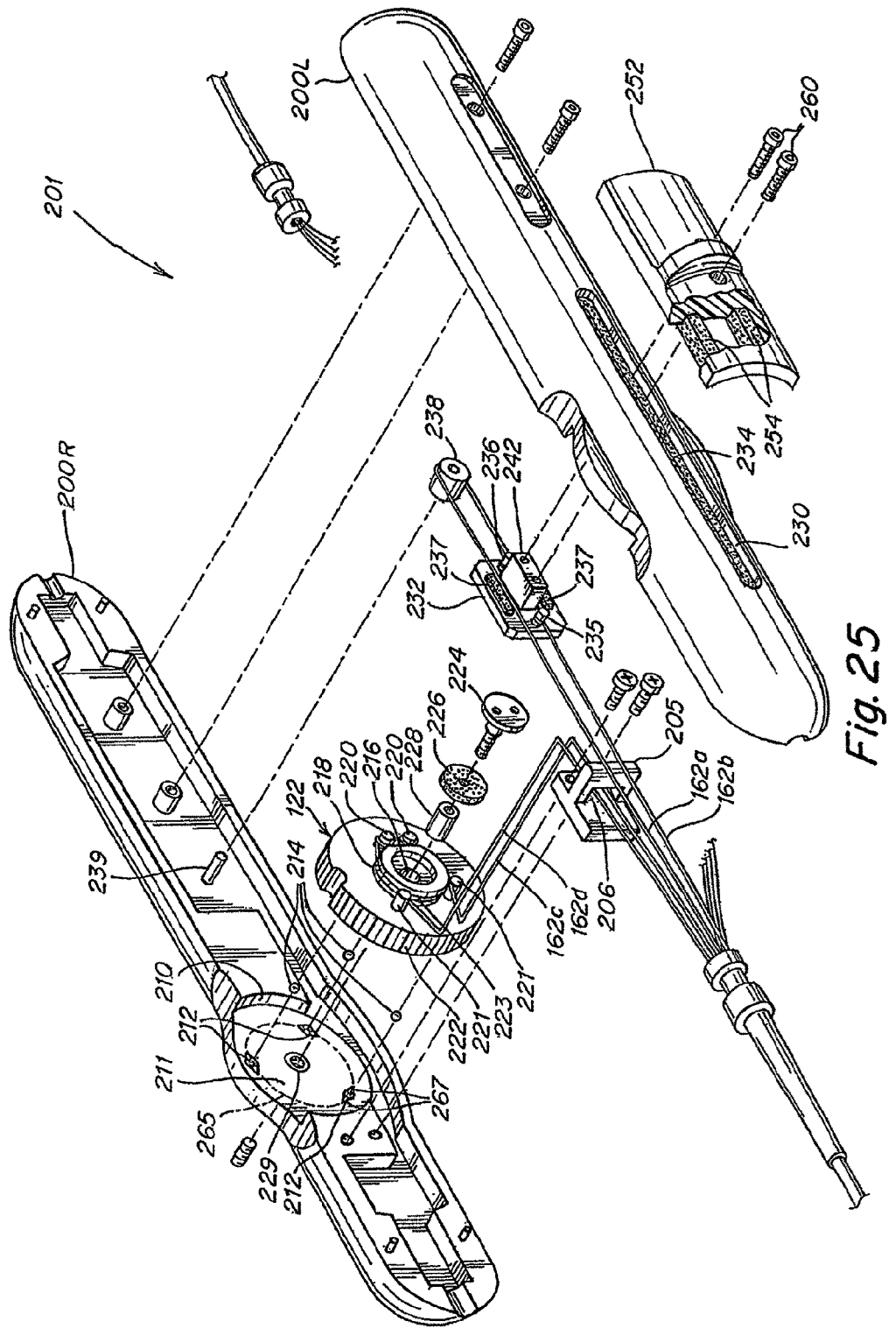
FIG. 25 is an exploded view of a handle that may be used with the catheter system of FIG. 1 according to another embodiment of the invention.

Referring to FIG. 25, the handle 201 comprises a housing having a left section 200L and a right section 200R. These two sections 200L and 200R are somewhat semicircular in crass section and have flat connecting surfaces which may be secured to each other along a common plane to form a complete housing for the handle 201. The outer surfaces of the handle 201 are contoured to be comfortably held by the user.

A wheel cavity 210 is formed within the right section 200R of the handle 201. The wheel cavity 210 includes a planar rear surface 211 which is generally parallel to the flat connecting surface of the handle 201. The thumbwheel actuator 122 is a generally circular disc having a central bore 216, an integrally formed pulley 218, and upper and lower cable anchors 220. Upper and lower cable guides 221 serve to retain the cables 162c and 162d within a guide slot or groove 223 formed in a surface of the integrally formed pulley 218. In the embodiment illustrated, the thumbwheel 122 rotates about a sleeve 228 inserted in the central bore 216. The thumbwheel 122 is held in position by a shoulder nut 224 that mates with a threaded insert 229 in the planar rear surface 211 of the right section 200R of the handle 201. To provide friction that permits the thumbwheel to maintain its position even when tension is applied to one of the cables 162c, 162d, a friction disk 226 is provided between the shoulder nut 224 and the thumbwheel 122. Tightening of the shoulder nut 224 increases the amount of friction applied to the thumbwheel 122.

A peripheral edge surface 222 of the thumbwheel 122 protrudes from a wheel access opening so that the thumbwheel 122 may be rotated by the thumb of the operator's hand which is used to grip the handle 201. To ensure a positive grip between the thumbwheel 122 and the user's thumb, the peripheral edge surface 222 of the thumbwheel 122 is preferably serrated, or otherwise roughened. Different serrations on opposite halves of thumbwheel 122 enable the user to "feel" the position of the thumbwheel.

The left section 200L supports part of the mechanism for selectively tensioning each of the two pull cables 162a and 162b that control the radius of curvature of the distal end of the catheter. To accommodate the protruding portion of the thumbwheel 122, the left handle section 200L includes a wheel access opening similar in shape to the wheel access opening of the right handle section 200R. It also includes an elongated slot 230 in its side surface.

A slider 232 is provided with a neck portion 242 which fits snugly within the slot 230. The slider 232 includes a forward cable anchor 235 and a rear cable anchor 236 for anchoring the pull cables 162a and 162b. Pull cable 162b is directly attached to the forward cable anchor 235 and becomes taught when the slider 232 is moved toward the distal end of the handle 201. Pull cable 162a is guided by a return pulley 238 prior to being attached to the rear cable anchor 236 and becomes taught when the slider 232 is moved toward the proximal end of the handle 201. The return pulley 238 is rotatably attached to a pulley axle 239 which is supported in a bore (not shown) in the flat surface of the right handle section 200R. The return pulley 238 may include a groove (not shown) to guide pull cable 162a. In the illustrated embodiment, a cable guide 205 is attached to the right handle section 200R to guide the cables 162a-162d and prevent their entanglement with one another. As shown, cables 162a and 162b are routed up and over the cable guide 205, while cables 162c and 162d are routed through a gap 206 in the cable guide 205. Grooves may be formed in a top surface of the cable guide 205 to keep cables 162a and 162b in position, although they could alternatively be routed through holes formed in the cable guide 205, or by other suitable means.

A slider grip 252 is attached to the neck portion 242 of the slider 232 and positioned externally of the handle 201. The slider grip 252 is preferably ergonomically shaped to be comfortably controlled by the user. Preload pads 254 are positioned between the outer surface of the left handle section 200L and the slider grip 252 (shown in FIGS. 25 and 28). By tightening the screws 260 that attach the slider grip 252 to the slider 232, friction is applied to the slider 232 and thus, to the pull cables 162a, 162b. Preload pads 237 may also be placed on a surface of the slider 232 for a similar purpose.

A dust seal 234 (FIGS. 25 and 28) having an elongated slit and preferably made from latex is bonded along the slot 230 within the left handle section 200L. The neck portion 242 of the slider 232 protrudes through the slit of the dust seal 234 so that the slit only separates adjacent to the neck portion 242. Otherwise, the slit remains "closed" and functions as an effective barrier preventing dust, hair and other contaminants from entering the handle 201. Further details of the handle 201 are described in U.S. Pat. Nos. 5,383,852, 5,462,527, and 5,611,777, which are hereby incorporated herein by reference.

According to a further aspect of the present invention, each of the thumbwheel actuator and the slide actuator may include means for imparting a first amount of friction on at least one pull cable to which the actuator is attached when the actuator is in a first position, and for imparting a second and greater amount of friction on the at least one pull cable when the actuator is moved away from the first position. According to this aspect of the present invention, the first position may correspond to a neutral position of the actuator wherein the tip assembly is aligned with the longitudinal axis of the shaft, or a neutral position of the actuator wherein the radius of curvature of the distal end of the tip assembly is neither being actively reduced or increased, and the second position may correspond to a position of the actuator that is other than the neutral or rest position.

As should be appreciated by those skilled in the art, it is desirable that the actuators for changing the orientation of the tip assembly and for controlling the radius of curvature of the distal end of the tip assembly remain in a fixed position, once actuated. Conventionally, this has been achieved by providing a sufficient amount of friction between the actuator and another surface on the handle 201 to resist movement of the actuator unless a certain amount of force is applied to the actuator. For example, in FIG. 25, by tightening shoulder nut 224 that holds the thumbwheel in position, a greater amount of force must be applied to the thumbwheel to rotate the thumbwheel from one rotational position to another. Similarly, and with respect to the slide actuator, by tightening the two screws 260 that hold the slider grip 252 in position against an undersurface of the handle section, a greater amount of force must be applied to the slider grip 252 to move the slider 232 from one position to another.

Although this conventional approach is straightforward, it results in the same amount of friction being applied to the actuator(s) in all positions, and not merely those positions that deviate from a neutral or rest position. Thus, in use, it can be difficult to ascertain whether the orientation of the tip assembly or the radius of curvature of the distal end of the tip assembly is in a neutral state, without visually looking at the handle. This can be problematic, as the user of the catheter would need to divert his or her attention to visually inspect the position of the actuator(s). Further, Applicants have determined that the frictional force imparted by the mechanisms that maintain the cables and actuators in a fixed position can significantly decrease over time, for example, while stacked on the shelf, oftentimes requiring that the mechanisms used to impart such friction (e.g., the shoulder nut and the screws) be tightened prior to use. It is believed that this phenomena is due to material creep associated with the various materials used to form the actuator mechanisms. This decrease in frictional force is especially apparent where the catheter has been brought to elevated temperatures during a sterilization cycle, as the materials from which the handle and the control mechanisms are formed have a tendency to yield at elevated temperatures. Although the various mechanisms may be tightened after sterilization, such tightening may contaminate the sterile nature of the catheter, and is undesirable in a clinical setting.

According to a further aspect of the present invention, each of the thumbwheel actuator and the slide actuator may include means for imparting a first amount of friction on at least one pull cable to which the actuator is attached when the actuator is in a first position, and for imparting a second and greater amount of friction on the at least one pull cable when the actuator is moved away from the first position. This difference in the frictional force can be perceived by the user to alert the user as to when the actuator is in a neutral or rest position, without visually inspecting the actuator. Further, because the frictional forces on the actuating mechanisms are reduced in a neutral or rest position, the catheter may be sterilized with the actuator(s) in a neutral or rest position, thereby reducing yielding of the actuation mechanism during sterilization.

According to one embodiment that is directed to the thumbwheel actuator, the means for imparting different amounts of friction may include a plurality of detents formed in the planar rear surface of the handle housing that cooperate with corresponding plurality of detents in a lower surface of the thumbwheel. In this embodiment, each of the plurality of detents in the lower surface of the thumbwheel receives a ball or bearing that sits partially within the respective detent. In a first neutral position, each of the balls also rest within a respective detent in the rear surface of the handle and exert a first amount of friction on the thumbwheel and the pull cables attached thereto. But, as the thumbwheel is rotated, the balls ride outside the detent in the rear surface of the handle onto the elevated surface above, thereby exerting a second and greater amount of friction on the thumbwheel and the pull cables attached thereto. According to one embodiment, this second amount of friction is sufficient to prevent the thumbwheel from returning to its neutral position. FIGS. 25, 29, 30, and 31 illustrate one implementation of a means for imparting different amounts of friction for a thumbwheel actuator 122 according to this embodiment of the present invention.

Figure 29:
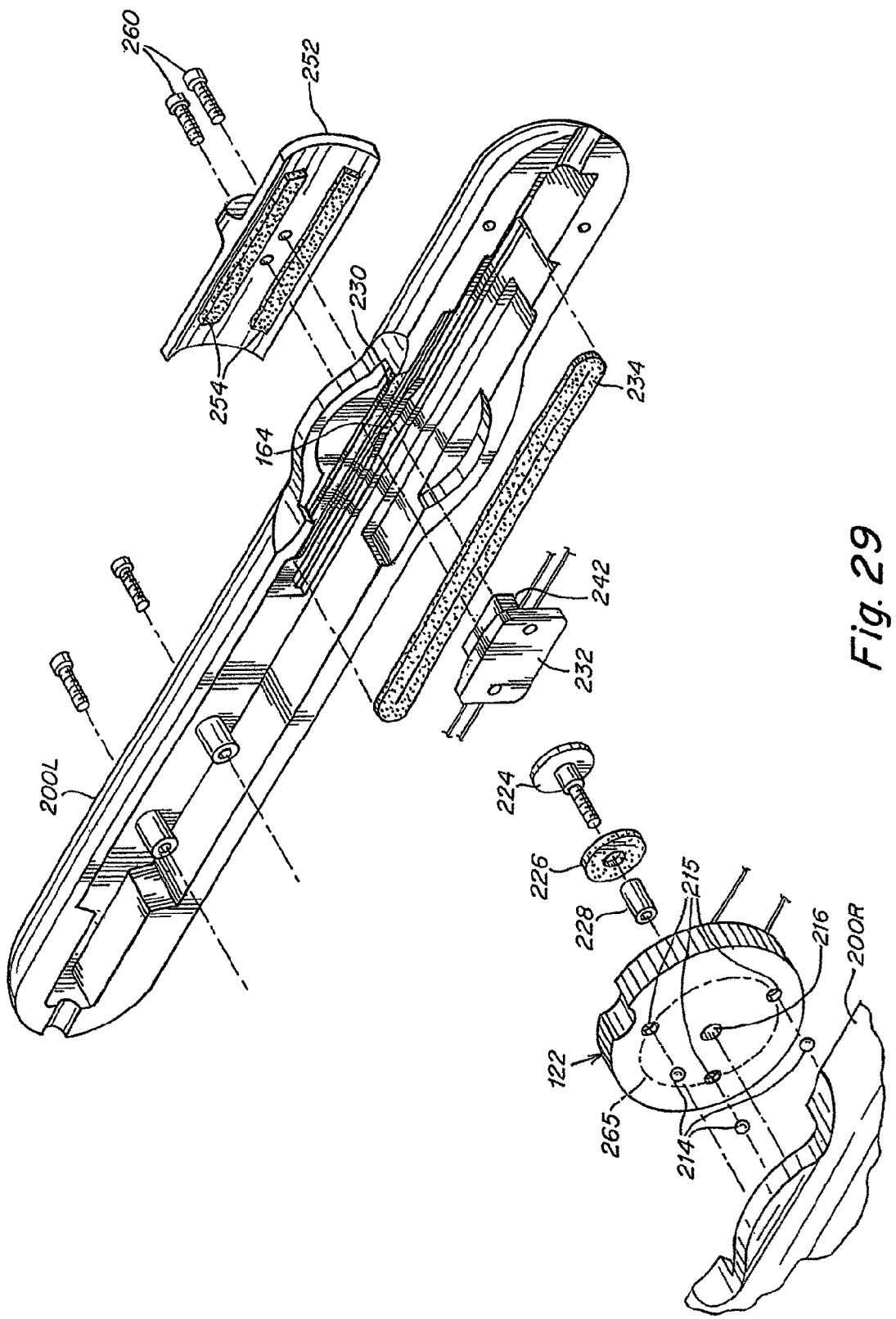
FIG. 29 is an exploded perspective view of the left section of the handle of FIG. 25.
Figure 30:
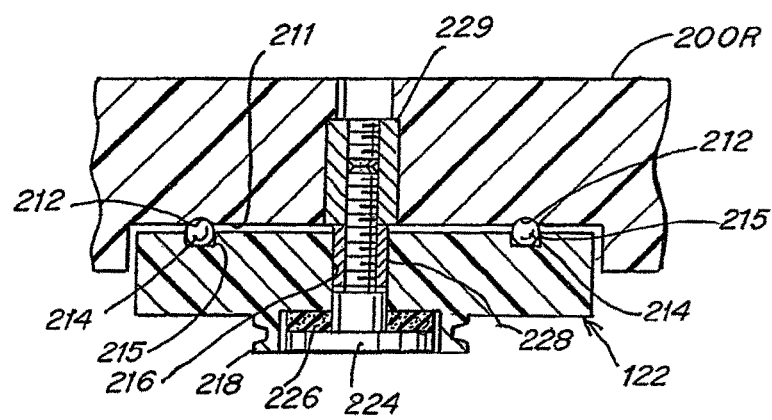
FIG. 30 is a schematic cross sectional view of a thumbwheel actuator for the handle of FIG. 25 in a neutral or unloaded state.
Figure 31:
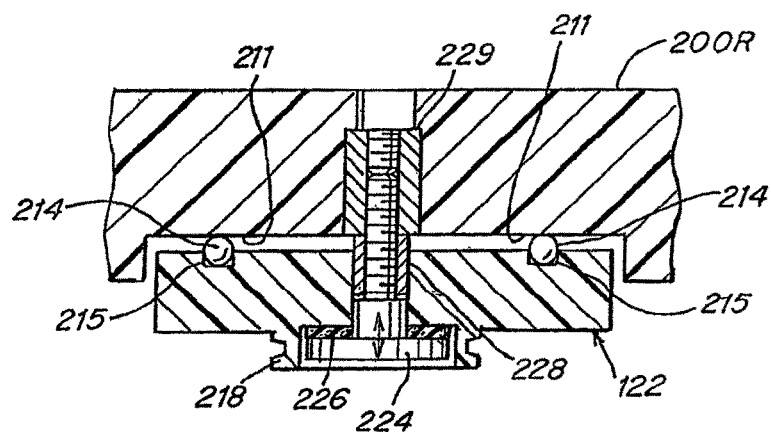
FIG. 31 is a schematic cross sectional view of the thumbwheel actuator for the handle of FIG. 25 in a deployed or loaded state.

As shown in FIGS. 25, 29, 30, and 31, the planar rear surface 210 of the right section 200R includes a plurality of detents 212 formed therein. A corresponding number of detents 215 are provided in an undersurface of the thumbwheel 122 (FIGS. 29-31). Within each of the plurality of detents 215 in the undersurface of the thumbwheel is a ball or bearing 214. The balls or bearings may be made from any suitable material, such as stainless steel, or may alternatively be made from a hard plastic. The balls or bearings 214 may be fixed in position for example, with an epoxy, or permitted to rotate within the detents 215. It should be appreciated that the balls or bearings 214 may alternatively be seated within the detents 212 in the planar rear surface 211 of the right section of the handle 200R. In a neutral or rest position, for example, corresponding to an orientation of the tip assembly that is parallel to the longitudinal axis of the shaft, each of the plurality of balls rests within a corresponding detent 212 in the planar rear surface 211. Such a resting or neutral state is depicted in FIG. 30 which is a schematic cross sectional view of the thumbwheel of FIG. 25. As may be appreciated, this neutral or rest position corresponds to a position of reduced friction on the thumbwheel 122 in which the friction disk 226 is compressed to only a small degree, and thus, to a reduced frictional force on the pull cables that are attached to the thumbwheel.

As the thumbwheel 122 is rotated from this neutral or rest position, the balls 214 ride up and out of their respective detents 212 and along the path 265 indicated in FIG. 25. In this second position wherein each of the balls contacts the elevated planar rear surface 211, a second and greater amount of friction is imparted to the thumbwheel, and thus, the pull cables attached thereto, that tends to prevent the thumbwheel from moving to another position without further rotational force applied to the thumbwheel. FIG. 31 is a schematic cross sectional view of the thumbwheel of FIG. 25 illustrating a state in which the thumbwheel is in a position other than the neutral or rest position. As can be seen in FIG. 31, each of the balls 214 rests upon the elevated planar rear surface 211 and the friction disk 226 is compressed relative to that shown in FIG. 30. As shown best in FIG. 22, each of the detents 212 in the planar rear surface 211 may include lead in/lead out sections 267 that are gradually tapered to the level of the planar rear surface 211 to facilitate smooth movement of the balls 214 out of and into the detents 212.

Although the present invention is not limited to the number of detents 212, 215 incorporated into the handle and the thumbwheel, Applicants have found that three detents spaced equally about a circumference of the planar rear surface 211 and the thumbwheel 122 distributes stress evenly about the thumbwheel 122 and permits a sufficient amount of rotation before another detent 212 is encountered. Furthermore, although the present invention is not limited to the amount of force applied to the thumbwheel to change the position of the thumbwheel, Applicants have empirically determined that a force of approximately 4 to 8 pounds is sufficient to resist any forces on the pull cables. Moreover, this amount of force is sufficient so that the thumbwheel cannot be moved inadvertently, and does not require great strength by the user. This amount of force also accounts for any yielding during storage and/or sterilization.

Although this embodiment of the present invention has been described in terms of a plurality of detents in a surface of the handle and a corresponding number of detents that hold a ball or bearing in an undersurface of the thumbwheel, the present invention is not so limited. For example, and as discussed above, the detents in the planar surface 211 of the handle 201 may hold the balls or bearings 214 and not the thumbwheel. Moreover, it should be appreciated that other means of imparting different frictional forces on the thumbwheel may be readily envisioned. For example, rather than detents, the rear planar surface 211 may be contoured to include a plurality of ramps (for example, three ramps). The undersurface of the thumbwheel 122 may include a corresponding plurality of complementary shaped ramps such that when the thumbwheel 122 is in a neutral or rest position, a minimum of friction is imparted, and as the thumbwheel 122 is rotated, the heightened surface of the ramps on the undersurface of the thumbwheel 122 contacts a heightened surface of the ramps in the planar surface. As the thumbwheel 122 is rotated further, addition friction is imparted.

According to another embodiment that is directed to the slide actuator, the means for imparting different amounts of friction may include a ramp disposed on or formed within the handle 201. In this embodiment, the apex of the ramp corresponds to a neutral position of the slider 232. In this neutral position, a minimum amount of friction is applied to the slider 232 and the pull cables 162a, 162b attached thereto. As the slider 232 is moved forward or backward away from the neutral position, the slider 232 is pushed toward the thumbwheel and an interior surface of the housing to impart a great amount of friction on the slider and the pull cables attached thereto. As with the thumbwheel, this second amount of friction is sufficient to prevent the slider from returning to its neutral position.

Figure 26:
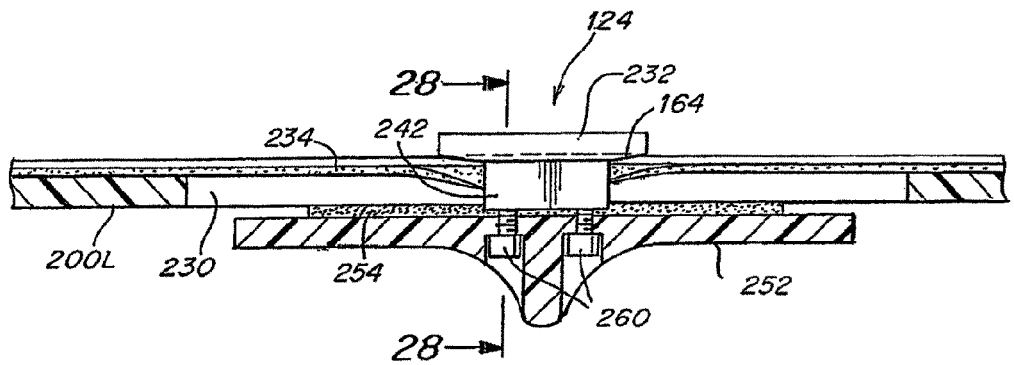
FIG. 26 is a schematic cross sectional view of a slide actuator for the handle of FIG. 25 in a neutral or unloaded state.
Figure 27:
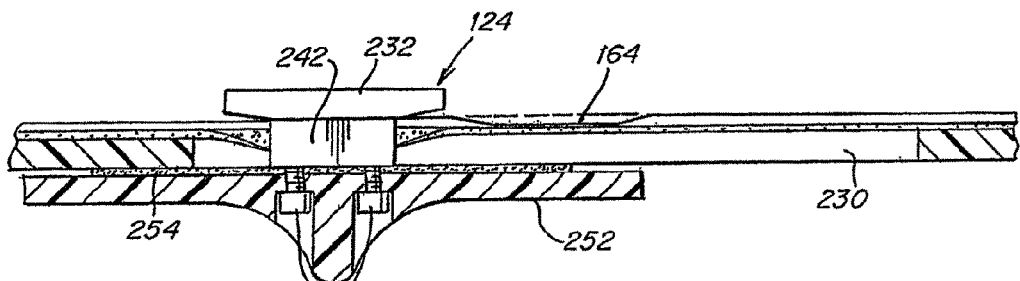
FIG. 27 is a schematic cross sectional view of a slide actuator for the handle of FIG. 25 in a deployed or loaded state.
Figure 28:
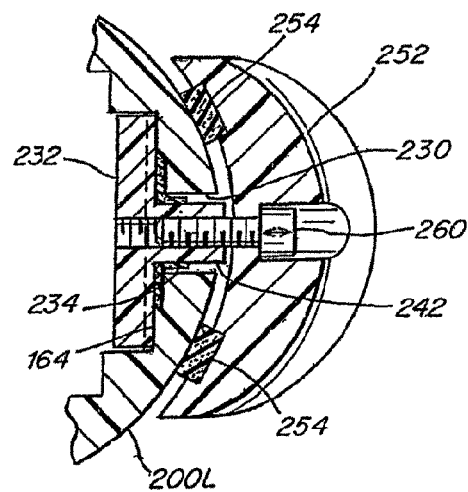
FIG. 28 is a cross sectional end view of the slide actuator of FIG. 26 taken along line 28-28 in FIG. 26.

FIGS. 26, 27, and 28 illustrate one implementation of a means for imparting different amounts of friction for a slide actuator 124. As shown in these figures, the undersurface of the left section 200L includes a ramp 164. The ramp may be integrally formed within the left section 200L of the handle 201, or alternatively, the ramp 164 may be separate from the handle and attached thereto. As illustrated in FIG. 28, which is a schematic cross sectional view of the slide actuator 124 shown in FIG. 26, the ramp 164 includes a central section of decreased thickness and proximal and distal sections that increase in thickness away from the central section until flush with the undersurface of the left section. The top surface of the slider 232 that contacts the undersurface of the left section 200L of the handle may have a complementary shape to the ramp as shown in FIGS. 26 and 27. In the position shown in FIG. 26, the slide actuator is in a neutral or rest position corresponding to a first radius of curvature of the distal end of the tip assembly. The two screws 260 force the slider grip 252 and the slider 232 closer to one another and compress the preload pads 254 therebetween. In the neutral or rest position shown in FIGS. 26 and 28, the preload pads 254 are compressed to only a minimal extent. However, as the slider 232 is moved away from the neutral or resting position, the shape of the ramp 164 (and the slider 232) imparts an additional frictional force that tends to separate the slider 232 from the slider grip 252, thereby compressing the preload pads 254 to a greater extent, as illustrated in FIG. 27. This additional frictional force resists the slide actuator 124 from changing position, absent further force on the slide actuator 124.

Although this embodiment of the present invention has been described in terms of a ramp formed within or disposed on an undersurface of the handle 201, the present invention is not so limited. For example, the ramp may alternatively be formed on an outer surface of the handle and provide similar functionality. Other means for imparting different frictional forces on the slide actuator may be readily envisioned by those skilled in the art.

Figure 32:
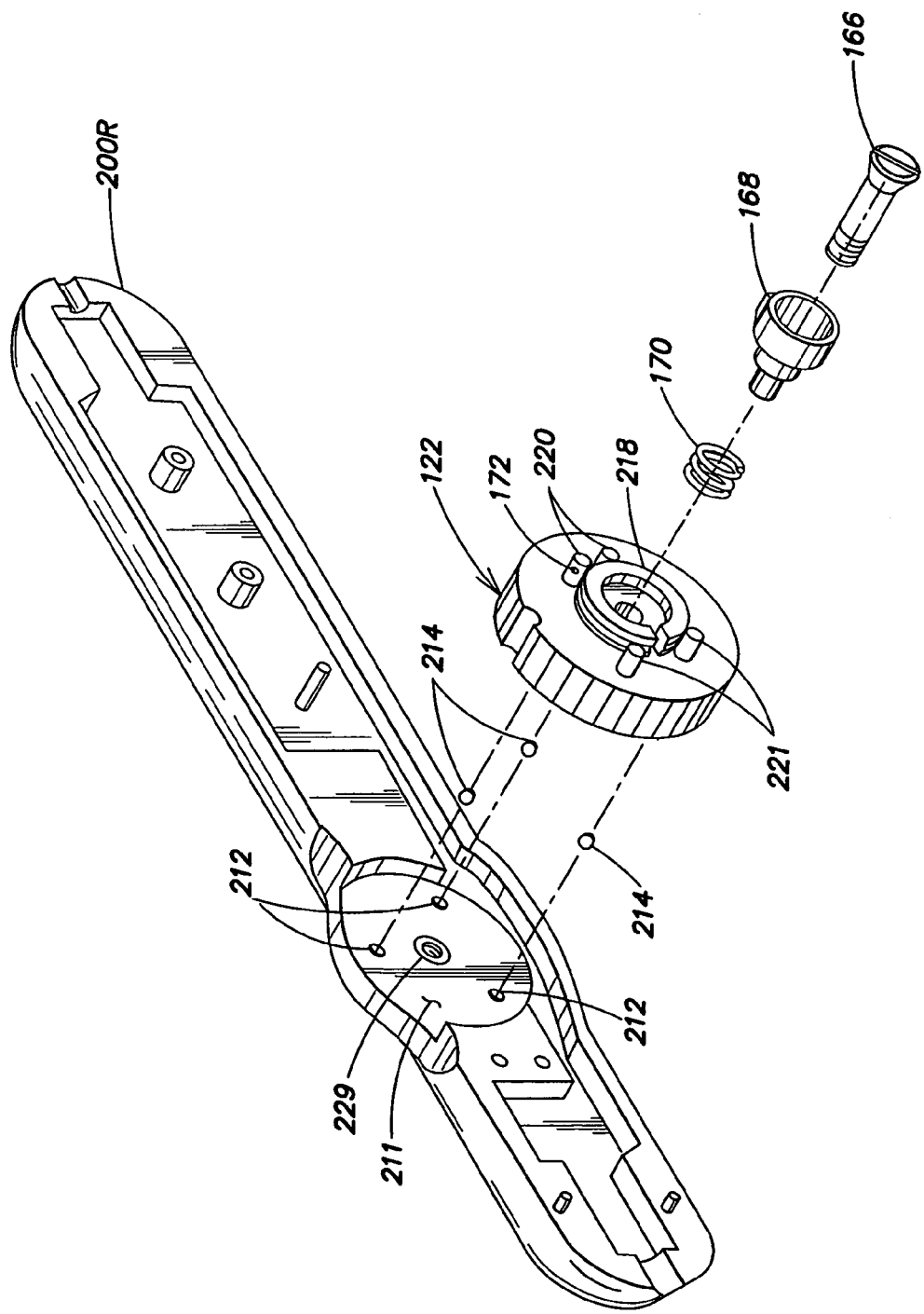
FIGS. 32-33 illustrate aspects of a handle configuration according to another embodiment of the invention.
Figure 33:
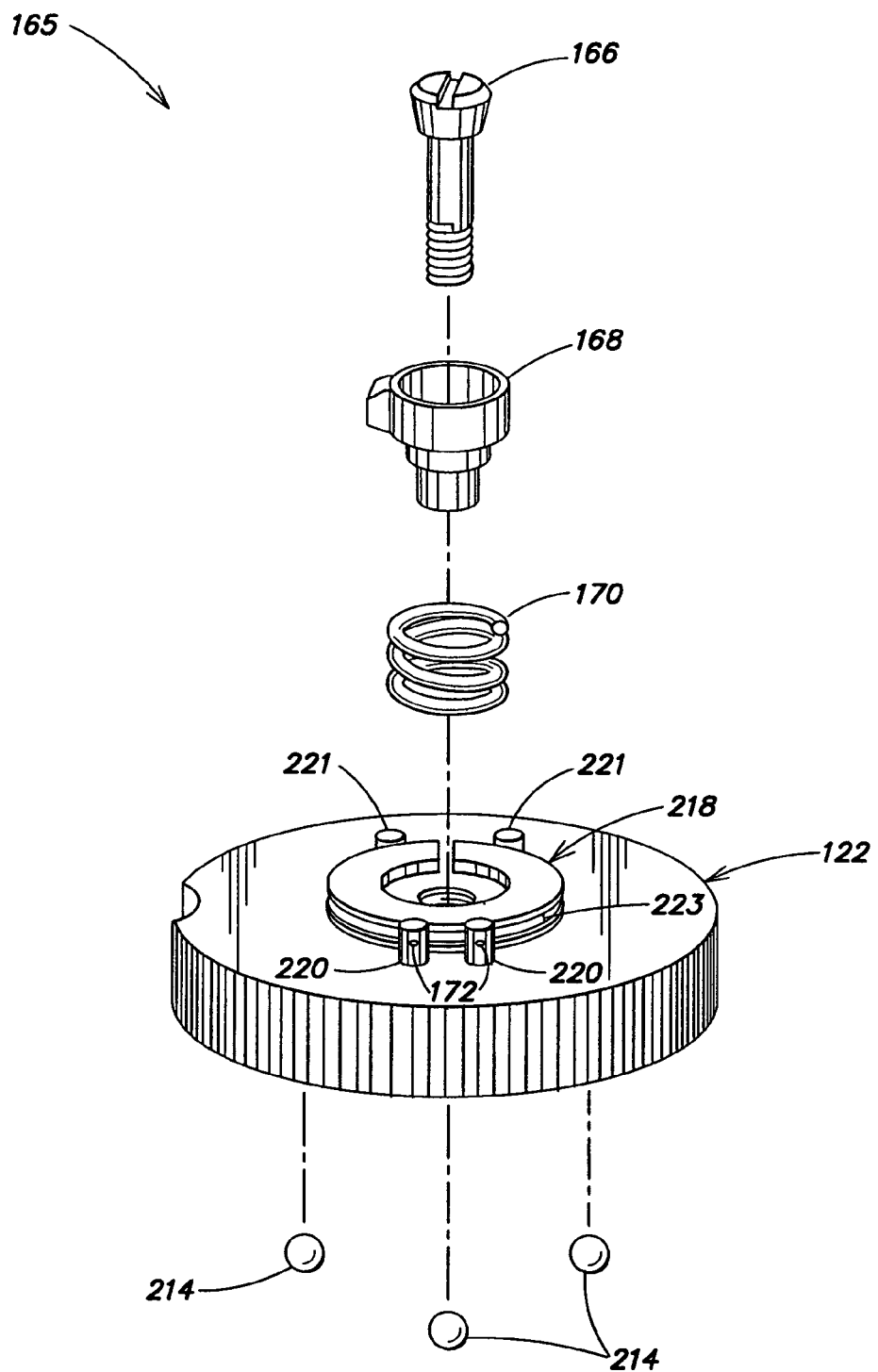

FIGS. 32-33 illustrates a variation of the handle 201 described in connection with FIG. 25. In particular, FIGS. 32-33 illustrate a thumbwheel assembly 165 that omits the friction disk 226 of FIG. 25, and instead includes a compression spring 170 to provide the friction that permits the thumbwheel 122 to maintain its position even when tension is applied to a cable coupled to one of cable anchors 220.

Compression spring 170 is provided between shoulder nut 168 and thumbwheel 122. The shoulder nut 168 is held in place by a screw 166 that mates with the threaded insert 229 in the planar rear surface 211 of the right section 200R of the handle. Compression of the spring 170 against the thumbwheel 122 increases the rotational friction imparted on the thumbwheel 122 such that thumbwheel 122 will maintain its position even when a tensioned cable coupled thereto exerts a rotational force on the thumbwheel 122.

As with the thumbwheel 122 of FIG. 25, balls or bearings 214 and corresponding detents 212 are provided for imparting a first amount of rotational friction on the thumbwheel 122 when the balls or bearings 214 rest within detents 212, and a second, greater amount of friction on thumbwheel 122 when the balls or bearings 214 are moved from the detents 212. Although not shown in FIGS. 32-33, detents 215 are also provided in an undersurface of the thumbwheel 122 (FIGS. 29-31) to receive balls or bearings 214. When balls or bearings 214 rest within detents 212, compression spring 170 is slightly compressed and a first frictional force is imparted on the thumbwheel 122. When the thumbwheel 122 is then rotated such that balls or bearings 214 are moved from the detents 212 as described in connection with FIG. 25, the compression spring 170 is compressed to a greater degree. Accordingly, a second greater frictional force is imparted in the thumbwheel 122.

Anchors 220, which may anchor pull cables secured thereto, may be adapted to allow selective tensioning of the pull cables. In particular, when the handle is opened to expose an anchor 220, an anchor 220 may be rotated (e.g., using a wrench) such that the cable coupled thereto may be looped around the anchor one or more times. The cable may be bent at an approximately ninety degree angle, and partially inserted into a hole 172 of the anchor 220 to secure the cable during rotation of the anchor 220. Accordingly, the tension on a cable attached to the anchor 220 may be increased by decreasing the slack in the cable. Tensioning of the cable may be desirable, for example. when the cable become slack after some period of time or after some period of use.

Pulley 218 may be formed with a smaller diameter than conventional thumbwheel pulleys so as to reduce the force necessary to turn thumbwheel 122. For example, pulley 218 may have a smallest diameter (e.g., the diameter of the pulley 218 at groove 223) of between ⅛ in. and ½ in. According to one embodiment, pulley 218 may have a smallest diameter of approximately ¼ in. According to another embodiment, pulley 218 may have a diameter that is approximately one third the size of the thumbwheel 122.

Although the above described embodiments for imparting a varying amount of friction on an actuator have been described with respect to actuators adapted to change the diameter of curvature or orientation of the distal end of a catheter, the present invention is not so limited. For example, the actuator may instead be coupled to a push/pull cable connected to a movable electrode, or a cable or rod used to deploy a braided conductive member as described in connection with FIGS. 34A-B. Accordingly, it should be appreciated that this embodiment of the present invention may be used to impart varying amounts of friction on any cable or other mechanism that controls movement of a portion of a catheter with respect to another.

Retractable Tip

Figure 34:
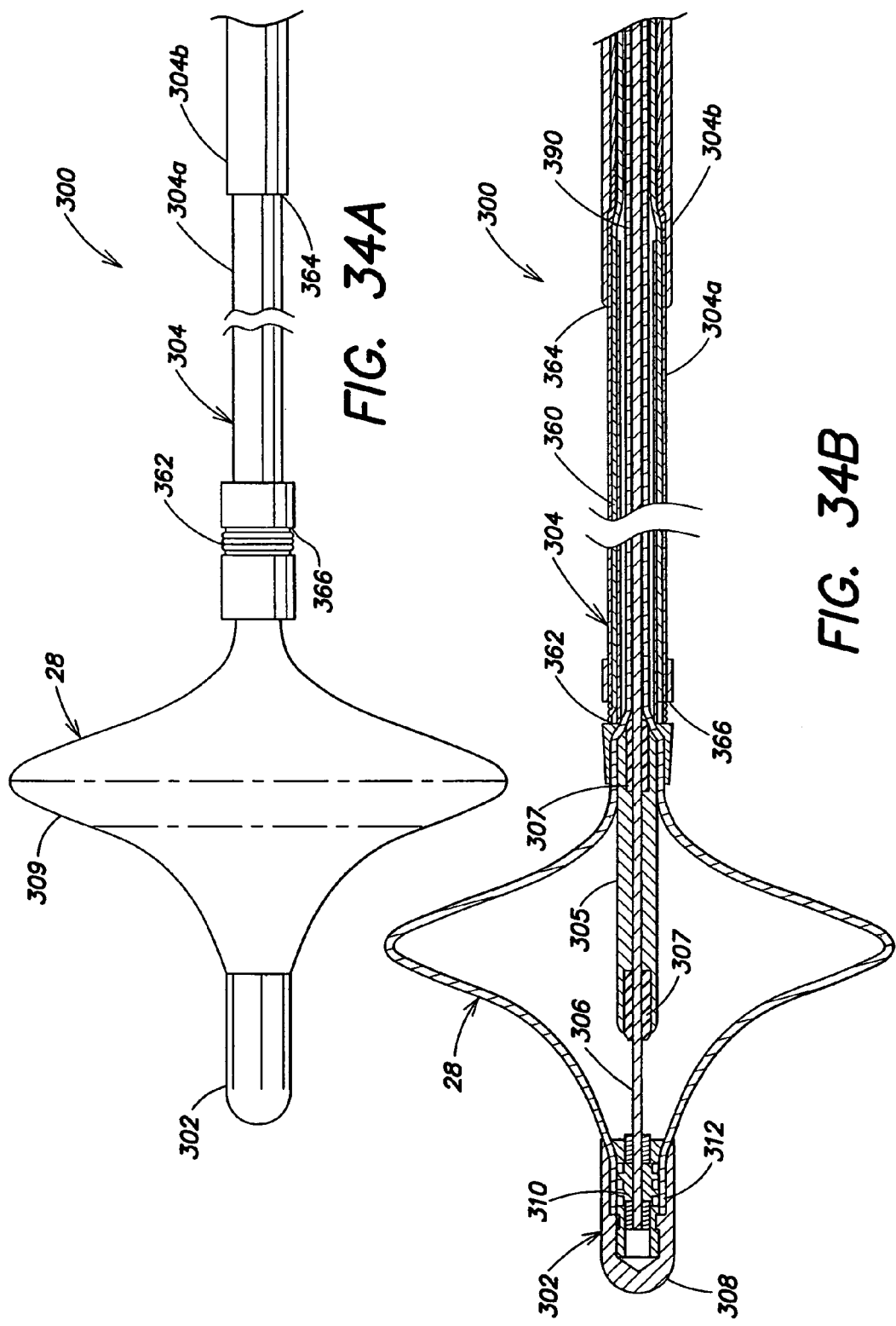
FIGS. 34-40 illustrate aspects of a catheter having a retractable distal tip portion.

The catheter 300 shown in FIGS. 34A-34B addresses one drawback that may be experienced when using a catheter such as shown in FIG. 1. When a catheter having a long distal end is used in an electrophysiology procedure involving the heart, the distal end may hinder the ability to maneuver the catheter within the heart. For example, certain pulmonary veins of the heart may branch to form smaller veins close to the heart. If the portion of the catheter that is distal to the braided conductive member is sufficiently long, the physician may have difficulty introducing the distal end of the catheter into a desired vessel and therefore may have difficulty positioning the braided conductive member.

As shown in FIGS. 34A-B, a distal tip portion 302 of catheter 300 may be retracted proximally in the direction of the shaft 304 using a mandrel 306 that is slidably disposed within the shaft 304, which results in the radial expansion of braided conductive member 28. Thus, the overall length of catheter 300 may be shortened when the braided conductive member 28 is deployed, which may aid the insertion of the distal tip portion of the catheter into a vessel during an electrophysiology procedure.

Catheter 300 comprises a distal tip portion 302, a shaft 304, and a braided conductive member 28 coupled therebetween. A mandrel 306 is fixedly attached to the distal tip portion 302 and slidably disposed within the shaft 304. A strain relief portion 305 is secured to shaft 304 to provide support for mandrel 306, which is slidable within a lumen of the strain relief portion 305. Plugs 307 may be secured to a distal portion of strain relief portion 305 to enable retraction of the mandrel within shaft 304, while preventing liquids or debris from entering the catheter 300. Accordingly, the plugs 307 may help to ensure that the interior of the catheter remains sterile. According to one example, plugs 307 may be formed of silicone or another elastomeric material.

Distal tip portion 302 comprises a distal cap 308 and an anchor portion 310. The anchor portion 310 performs two primary functions. First, the anchor portion 310 helps to secure the distal end 312 of braided conductive member 28 to distal cap 308. Second, the anchor portion 310 secures a distal end of the mandrel 306 to the distal tip portion 302.

As will be discussed in more detail below, mandrel 306 is movable with respect to the shaft 304 of the catheter 300. Advantageously, mandrel 306 may be used to transmit pulling forces as well as pushing forces. Thus, mandrel 306 may be used both the deploy and undeploy braided conductive member 28. It should be appreciated that mandrel 306 may comprise any actuating mechanism that is capable of transmitting both pulling and pushing forces. For example, mandrel 306 may comprise a rod, a wire, or other actuating member having sufficient rigidity to enable transmission of pushing forces. In one example, mandrel 306 may be formed of nitinol or another material exhibiting superelasticity, although the invention is not limited in this respect.

Mandrel 306 may include a coating, which may for example enhance the operating properties of the mandrel. For example, the mandrel 306 may be coated to reduce the possibility of thrombi adhesion to the mandrel 306 and/or to provide a reference a radio-opaque point on mandrel 306 when viewed during fluoroscopic imaging. According to another example, the mandrel 306 may be coated with a high dielectric coating for safety when using ablation energy, as a portion of the mandrel 306 may be exposed to blood during an electrophysiology procedure. One exemplary high dielectric coating that may be used is parylene. According to a further example, the mandrel 306 may be coated to reduce the coefficient of friction of the mandrel 306. Such a coating may reduce the friction that may result between mandrel 306 and plugs 307 or between mandrel 306 and braided cable 390, an external portion of which forms the braided conductive member 28 at the distal end of the catheter 300. A parylene coating may act to reduce this friction when applied to the mandrel 306, and may therefore may serve dual functions of acting as a dielectric and acting as a lubricant.

Braided conductive member 28 may include any of the features described in connection with other braided conductive members. In particular, braided conductive member 28 may be partially insulated, and may include an uninsulated portion 309 around a circumference thereof (FIG. 34A). The insulated portion may be preferentially disposed on a distal face of the braided conductive member 28, such that a larger area of the braided conductive member 28 is uninsulated on its distal face.

The actuation of braided conductive member 28 using mandrel 306 will now be described. Sliding the mandrel 306 within the shaft 304 of catheter 300 changes the configuration of the braided conductive member 28. In particular, when the mandrel 306 is slid distally within the shaft 304, the braided conductive member 28 assumes an undeployed configuration. The undeployed configuration may be generally cylindrical. The diameter of the diameter of the braided conductive member 28 in this configuration may approximate that of the shaft 304. When the mandrel 306 is slid proximally within the shaft 304, the braided conductive member 28 assumes a deployed configuration. The deployed configuration may have a disk-like shape. The braided conductive member 28 in this configuration has a larger diameter than in the undeployed configuration. Thus, deploying the braided conductive member 28 expands the braided conductive member 28 radially.

Figure 35:
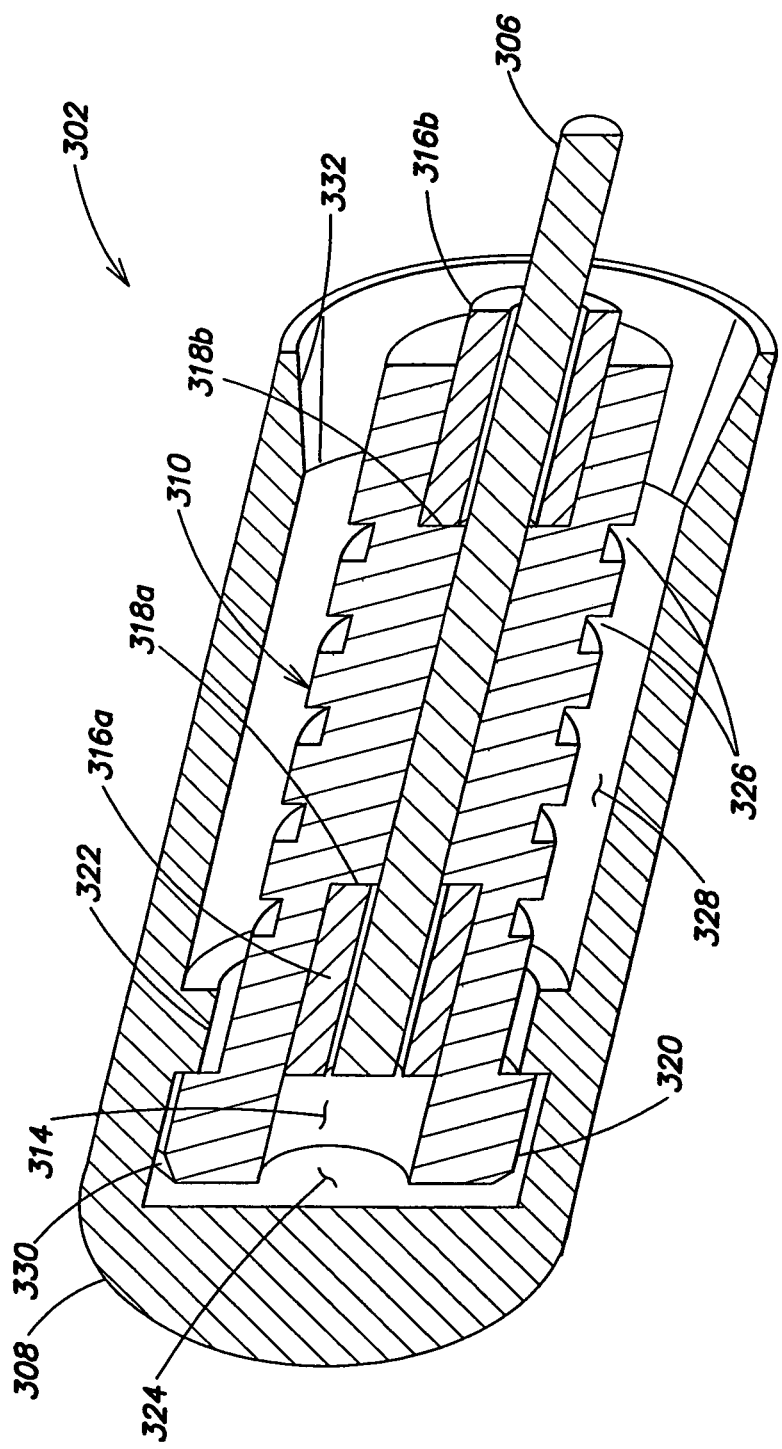

FIG. 35 illustrates an enlarged view of the distal tip portion 302 shown in FIG. 34B. As shown, anchor portion 310 includes a central opening 314, within which mandrel 306 is disposed. Mandrel 306 is secured within anchor portion 310 via first and second collets 316a and 316b. In one example, the first collet 316a may be secured to the mandrel 306 using solder and the second collet 316b may be secured to the mandrel 306 using a bonding agent such as epoxy, although the invention is not limited in this respect. Collets 316a and 316b anchor the mandrel 306 with respect to the anchor portion 310. As may be appreciated from FIG. 35, any motion of mandrel 306 with respect to anchor portion 310 when mandrel 306 is slid within the shaft of the catheter is inhibited by the interface of collets 316a and 316b with edges 318a and 318b, respectively. For example, if mandrel 306 is slid within the shaft in a proximal direction, the interface of first collet 316a with edge 318a inhibits motion of the mandrel 306 with respect to anchor portion 310. Similarly, if mandrel 306 is slid within the shaft in a distal direction, the interface of second collet 316b with edge 318b inhibits motion of the mandrel 306 with respect to anchor portion 310.

Anchor portion 310 also includes features that interface with distal cap 308. First, a collar 320 of anchor portion 310 is configured to mechanically "lock" the anchor portion 310 in distal cap 308. When anchor portion 310 is properly positioned within distal cap 308, collar 320 is adjacent to a corresponding collar 322 of distal-cap 308. Hence, when collar 320 is positioned at a distal end of distal cap 308, collar 322 is proximal to and adjacent collar 320, which thereby inhibits proximal motion of anchor portion 310 with respect to distal cap 308. In addition, when collar 320 is positioned at a distal end of distal cap 308, collar 320 is adjacent to a distal interior wall 324 of distal cap 308. The interface therebetween inhibits distal motion of anchor portion 310 with respect to distal cap 308.

Second, anchor portion 310 includes a plurality of grooves 326 on an outer surface thereof that may provide a suitable surface for a bonding agent, e.g., epoxy, disposed between anchor portion 310 and distal cap 308 to adhere. A distal end 312 of braided conductive member 28 (FIG. 34B) may be secured in a recess 328 between anchor portion 310 and distal cap 308. A bonding agent disposed within the recess 328 secures the braided conductive member 28 within the distal cap 308. If desired, anchor portion 310 may include a ramp 332 of approximately fifteen degrees at proximal end thereof to maintain the distal end of the braided conductive member 28 in a conical shape.

One exemplary process for the assembly of the distal tip portion 302 will now be described. First, the first collet 316a may be secured to the mandrel 306, for example using solder or epoxy. Next, the anchor portion 310 may be slid over the first collet 316a and mandrel 306, and second collet 316b may be secured to the mandrel 306, for example using solder or epoxy. The anchor portion 310, which is secured to collets 316a-b and mandrel 306, may then be inserted into distal cap 308. Anchor portion 310 may be formed by machining, or another suitable process. A chamfer 330 may be provided at the distal end of anchor portion 310 to aid the insertion of anchor portion 310 past the collar 322 of distal cap 308. The individual wires of the braided conductive member 28 may be cut and then separately insulated at their distal ends with an ultraviolet cure adhesive. A potting material may be included between anchor portion 310 and distal cap 308 to secure the distal end of the braided conductive member 28 therebetween.

Figure 36:
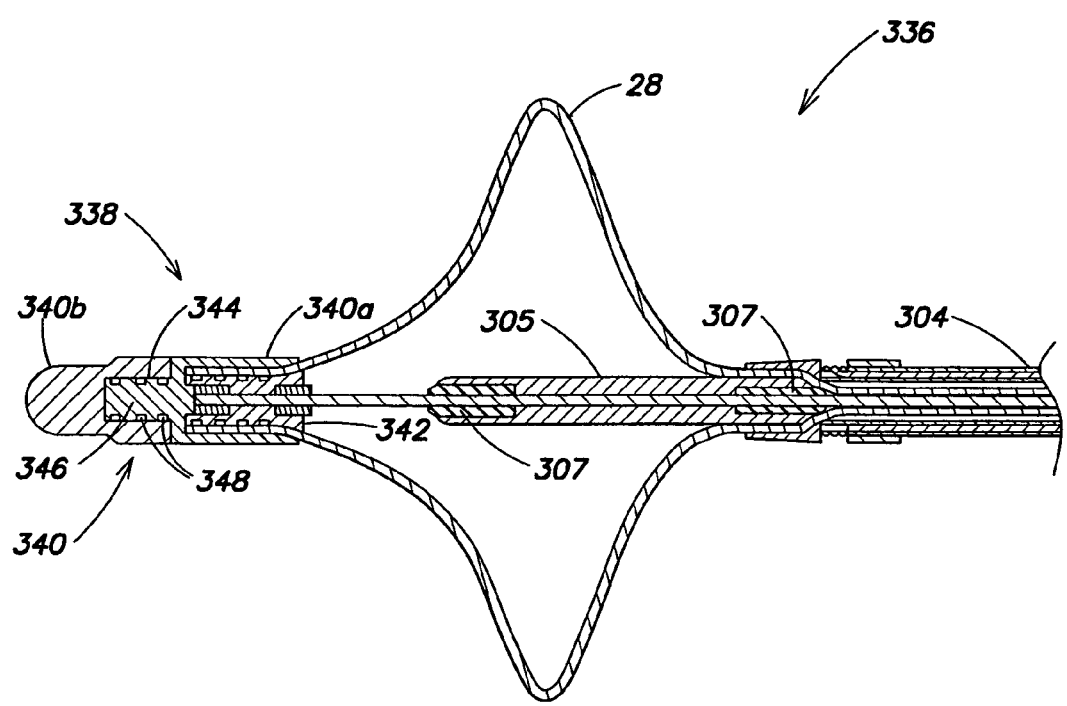

Because distal tip position 302 may be maneuvered through vasculature and the heart during the course of an electrophysiology procedure, it may be desirable that distal tip portion 302 be constructed so as to reduce trauma to tissue it may contact. Accordingly, FIG. 36 illustrates an exemplary embodiment of a portion of catheter 336 having a distal tip portion 338 that includes material selected to provide a gentle interaction with tissue. Distal tip portion 338 comprises a distal cap 340 and an anchor portion 342. Anchor portion 342 is similar to and performs the same as the anchor portion 342 of FIG. 35. Distal cap 340 includes two sub-portions: a proximal portion 340a and a distal portion 340b. Proximal portion 340a is similar to and performs the same function as the distal cap 308 of FIG. 35, but includes a protrusion 346 adapted to mate with a recess 344 of distal portion 340b. A bonding agent such as epoxy, or alternate coupling means, may be included in grooves 348 in proximal portion 340a to secure the proximal portion 340a to distal portion 340b. Distal portion 340b may be constructed to provide a more gentle interaction with tissue than occurs with conventional catheter tips. For example, distal portion 340b may be formed of an elastomeric material such as polyurethane or silicone, or another material having a low durometer. Accordingly, distal cap 340 may be used, for example, to locate vein entrances in the walls of the atria without damaging the tissue of the wall. It should be appreciated that a number of variations are possible for the distal cap portion 340 described above. For example, a unitary cap portion may be formed with the "atraumatic" properties described for the distal portion 340b, or both proximal portion 340a and distal portion 340b may be formed with atraumatic properties. In addition, distal portion 340b can assume a number of different configurations and need not have the shape and dimensions shown in FIG. 36.

Referring again to FIG. 34A-B, a steering arrangement that may be used in connection with catheter 300 according to another embodiment of the invention wilt now be described. Steering cables 360 may be provided within catheter 300 to enable the catheter to be bent or curved via actuation of one or more of the steering cables 360. Steering cables 360 may be anchored at steering anchor 362, which is located at a distal end of shaft 304. Actuation of one or more steering cables 360 may cause a bend or curve at a location proximal to steering anchor 362, for example at a junction 364 between distal shaft portion 304a and proximal shaft portion 304b. In one example, distal shaft portion 304a may be formed of a less rigid material than proximal shaft portion 304b so that a bend or curve is formed at a portion of the distal shaft portion 304a near the junction 364 between the distal shaft portion 304a and the proximal shaft portion 304b. As should be appreciated from the foregoing, according to one embodiment of the invention, steering anchor 362 may be provided proximal to braided conductive member 28. Further, a steering "knuckle" (e.g., a location of a bend or curve) may be formed by actuation of a steering cable 360 anchored at steering anchor 362 at a location proximal to the steering anchor.

In the example shown in FIGS. 34A-34B, steering anchor 3249 comprises a plurality of loops formed by steering cables 360 around an exterior surface of catheter 300, wherein the steering cables 360 form a continuous length of cable. The loops may be formed in a recess 366 in the exterior surface of the catheter 300, and may be potted in place and sealed with silicone. In one example, an uncoated section of the steering cables 360 is looped around the catheter shaft 304 two and a half times and then potted to provide sufficient tensile forces for the cables 360.

Although the configuration shown in FIGS. 34A-B provides suitable anchoring of steering cables 360, certain drawbacks exist. For example, an opening is needed via which steering cables 360 may exit the catheter shaft 304 so that they may be looped around the exterior surface of the catheter 300. The opening in the catheter shaft 304 may result in fluid leakage into the catheter 300, or may cause other undesirable results.

Figure 37:
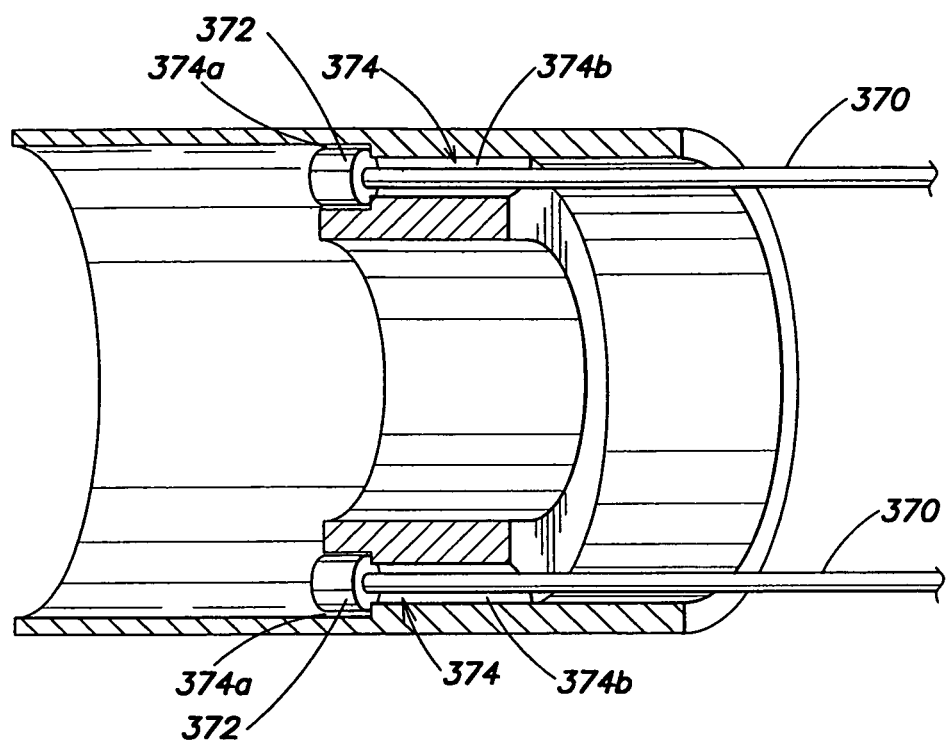

FIG. 37 illustrates an alternative configuration of a steering anchor that may be used in accordance with catheter 300 and other embodiments described herein. In the configuration shown in FIG. 37, steering cables 370 are provided with anchors 372 having a width or diameter that is greater than the diameter of steering cables 370. The anchors 372 may be integrally formed with the steering cables 370 or may be securely attached thereto. Steering cables 370 are at least partially disposed in lumens 374 having a larger width or diameter region 374a and a smaller width or diameter region 374b. Anchors 372 may be disposed in larger width or diameter region 374a and may be sized such that the anchors 372 do not fit within smaller width or diameter region 374b. In other words, each anchor 372 may have a diameter or width that is larger than a diameter or width of smaller with or diameter region 374b and smaller than a diameter or width of larger width or diameter region 374a. Accordingly, steering cables 360 may be anchored at the junction of regions 374a-b. A bonding agent such as epoxy may be provided to secure the anchors 372 at this location.

Figure 38:
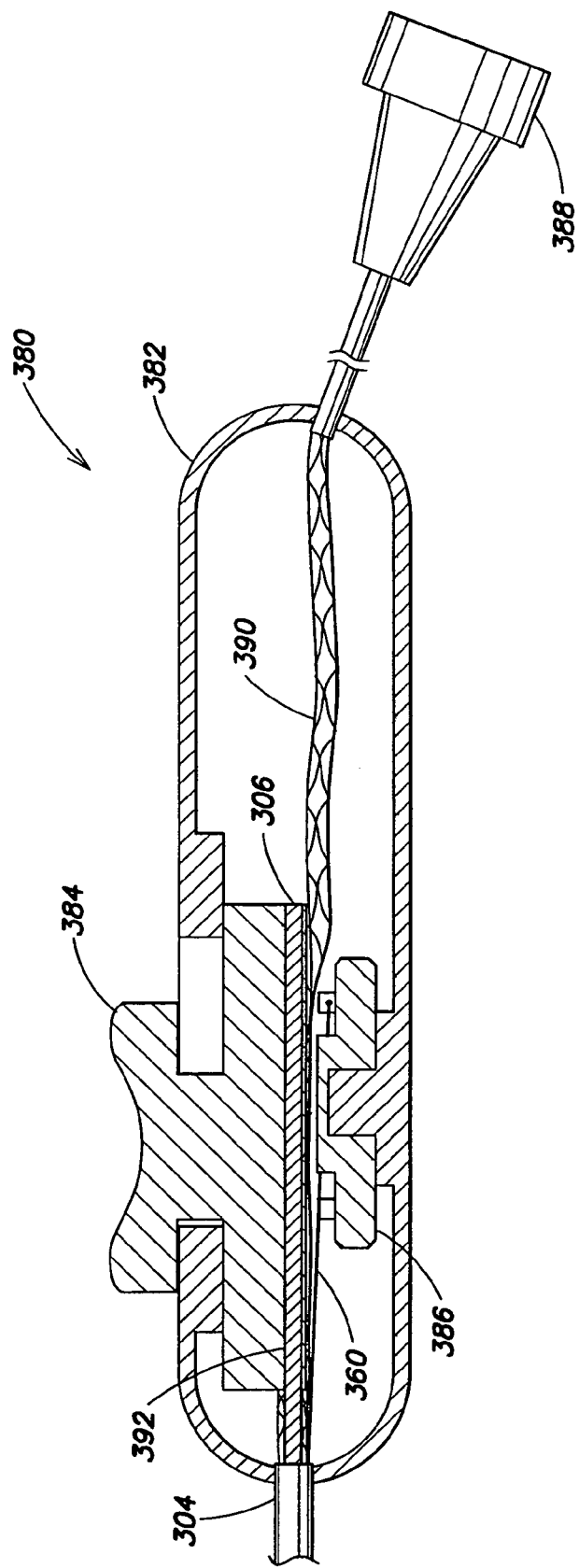

FIG. 38 illustrates an exemplary implementation of a control handle for use with the catheter 300 shown in FIGS. 34A-B. The handle 380 includes a housing 382, and a slide actuator 384 and thumbwheel 386 coupled to the housing 382. The slide actuator 384 is coupled to the mandrel 306 to actuate the mandrel. Slide actuator 384 includes a lumen 392 in which a distal portion of mandrel 306 is disposed. The mandrel 306 may be fixedly attached to the slide actuator 384, for example using an adhesive disposed in the lumen 392 between the mandrel 306 and the slide actuator 384. The thumbwheel 386 may be coupled to one or more steering cables, such as steering cables 360 discussed in connection with FIGS. 34A-B. Thus, thumbwheel may be use to actuate steering cables 360 to control an orientation of catheter 300 (FIGS. 34A-B).

Handle 380 is coupled to the catheter shaft 304 at a distal end thereof and a connector 388 at a proximal end thereof. A braided cable 390, an external portion of which forms braided conductive member 28 at a distal end of the catheter 300 (FIGS. 34A-B), travels from the shaft 304 to the connector 388 through the handle 382. In the catheter shaft, the braided cable 390 may be concentrically disposed around mandrel 306. In the handle 380, the mandrel 306 may exit through an opening in braided cable 390 such that the braided cable 390 is no longer disposed around mandrel 306. It should be appreciated however, that braided cable 390 need not be concentrically disposed about mandrel 306 in shaft 304 and that the configuration shown is merely exemplary. In addition, braided cable 390 need not be braided along an entire length thereof. For example, braided cable 390 may comprise a plurality of unbraided filaments that are braided only at a distal end thereof where braided conductive member 28 is formed.

Figure 39:
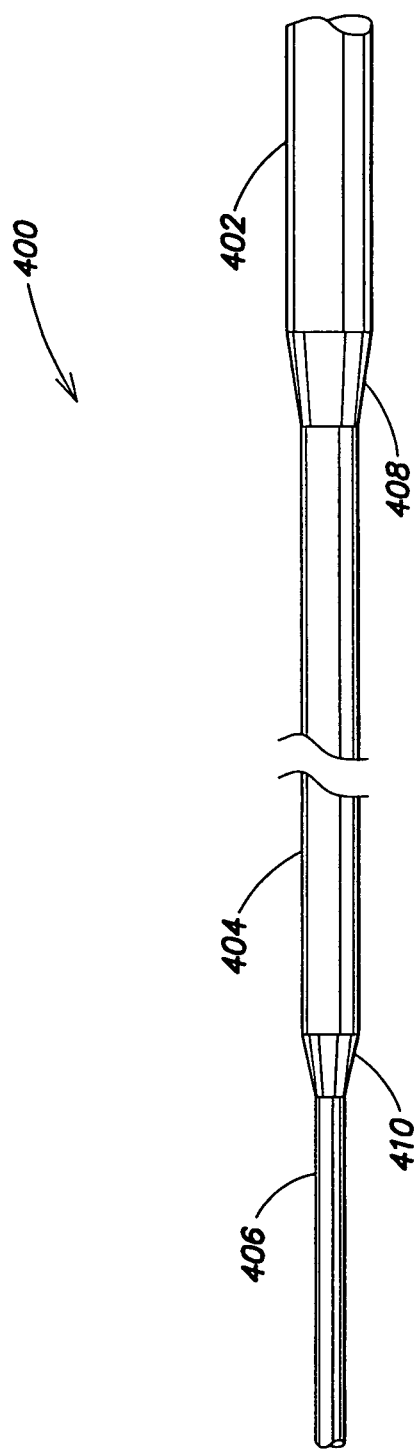
Figure 40:
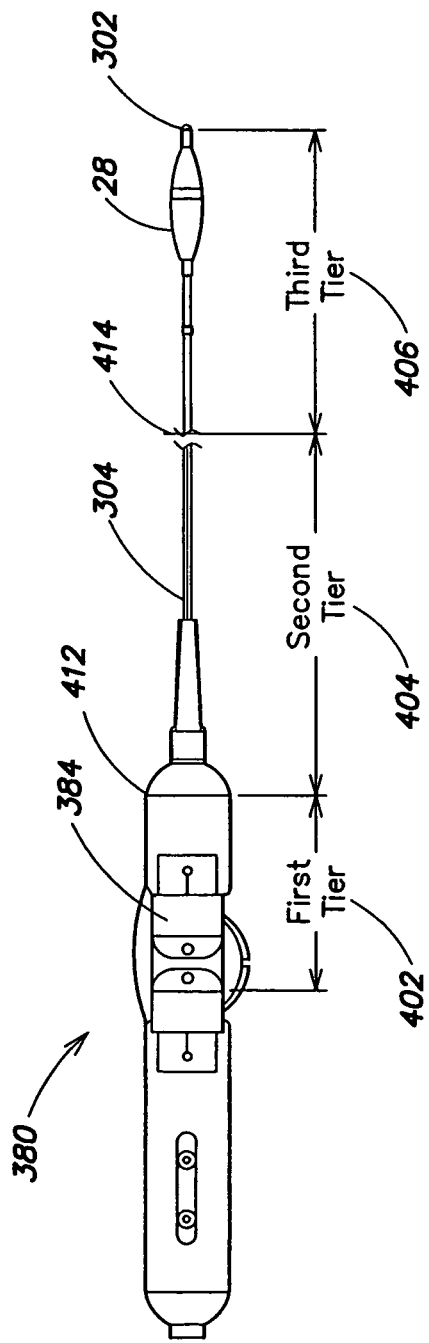

Mandrel 306 should be sufficiently stable in the region of handle 380 to transmit the pushing force applied by slide actuator 384 to more distal portions of mandrel 306. Thus, it is preferable that the mandrel 306 have a sufficient diameter in the region of handle 380 to provide such stability. However, if this diameter of mandrel 306 were used along the entire length of the mandrel, the distal end of the catheter 300 may be excessively stiff. Excessive stiffness at the distal end of the catheter is undesirable as it may result in trauma to the heart and/or vasculature. FIGS. 39-40 illustrate an exemplary implementation of mandrel 306 that addresses these considerations. In particular, the mandrel of FIGS. 39-40 may have increased flexibility at a distal end thereof such that a catheter that incorporates the mandrel will also have increased flexibility at its distal end. Thus, trauma to the heart and/or vasculature may be reduced because the distal tip may yield when it contacts tissue due to its flexibility. In addition, the increased flexibility of the distal end of the catheter may enhance the maneuverability of the catheter, which may also reduce undesirable contact with the heart and/or vasculature.

FIG. 39 illustrates a mandrel 400 having three tiers: a first tier 402, a second tier 404, and a third tier 406. The first tier 402 and second tier 404 are connected via a first transition region 408, and the second tier 404 and third tier 406 are connected via a second transition region 410. The transition regions may have a gradual and linear profile. The first tier 402 has the largest diameter of the three tiers, which may be approximately 0.038 inches according to one example. The second tier 404 has a diameter that is smaller than that of the first tier 402 but larger than that of the third tier 406. According to one example, the second tier has a diameter of approximately 0.028 inches. The third tier 406 has the smaller diameter of the three tiers, which may be approximately 0.0175 inches according to one example. One exemplary material for mandrel 400 is nitinol, or another superelastic material. Nitinol has the benefit of being more resistant to kinking than other materials that may be used for mandrel 400, such as stainless steel.

FIG. 40 illustrates exemplary locations for the first, second, and third tiers within catheter 300. The first tier 402 may extend from slide actuator 384, where the distal end of the mandrel is coupled, to a location 412 at the distal end of the handle 380. Thus, the first transition 408 (FIG. 39) may occur at location 412. The second tier 404 may extend from location 412 to a location 414 located in shaft 304. Thus, the second transition 410 (FIG. 39) may occur at location 414. The third tier 406 may extend from location 414 to distal tip portion 302.

It should be appreciated that a number of variations are possible on the mandrel 400 described in connection with FIGS. 39-40. For example, the mandrel 400 may comprise two tiers, four tiers, or some greater number of tiers. Alternatively, the mandrel 400 may be constructed to have a continuous taper along an entire or substantial length thereof. It should also be appreciated that the transition regions 408 and 410 need not be gradual. For example, the transitions may be perpendicular relative to tiers of the mandrel 400.

FIGS. 41A-E illustrate a modified version of the catheter 300 illustrated in FIGS. 34A-B. Most notably, catheter 416 includes a mandrel 418 having an interior lumen 420. As will be discussed in detail below, lumen 420 may provide a passage for fluids or devices used during an electrophysiology procedure.

Figure 41A:
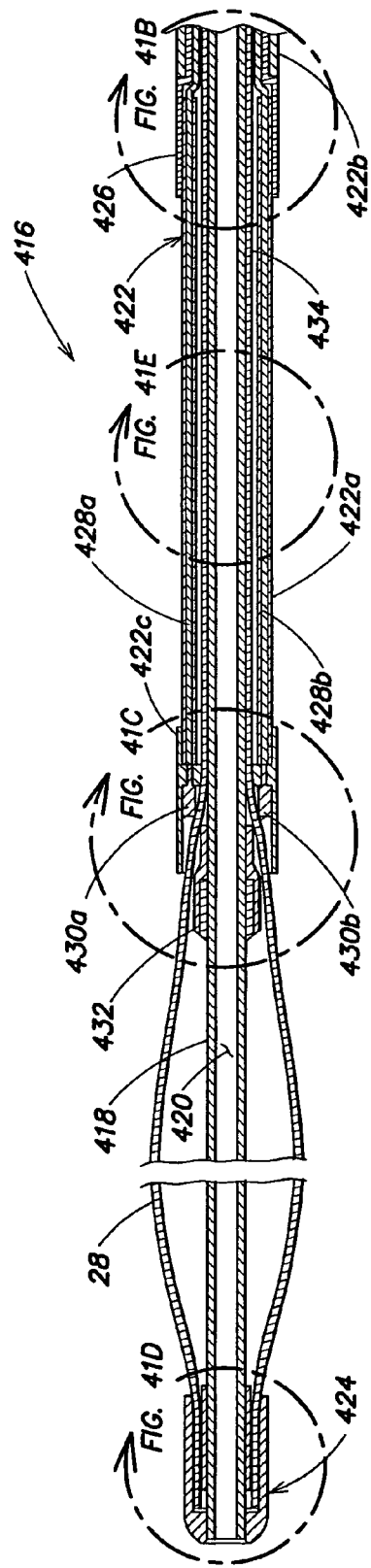
FIGS. 41-42 illustrate a modified version of the catheter illustrated in FIGS. 34-40 having a lumen for the delivery of fluids or devices.

As shown in FIG. 41A, catheter 416 includes a catheter shaft 422, a braided conductive member 28, and a distal tip portion 424. The catheter shaft 422 includes a distal shaft portion 422a, a proximal shaft portion 422b, and an anchor portion 422c coupled between diital shaft portion 422a and braided conductive member 28. A counterbore 426 is coupled between the proximal shaft portion 422b and the distal shaft portion 422a. Steering cables 428a and 428b are respectively anchored via anchors 430a and 430b, which are secured within anchor section 422c. A seal 432 is provided at a distal end of anchor section 422c to prevent or substantially avoid admitting fluid or debris into the interior of shaft 422.

According to one implementation, the lumen 420 of mandrel 418 has a diameter of approximately 2.5 French, while catheter shaft 422 has a diameter of approximately 10 French when no steering cables are used and approximately 12.5 French when two steering cables are used. However, it should be appreciated that the dimensions provided above are merely exemplary, and that alternative dimensions may be suitable.

Figure 41B:
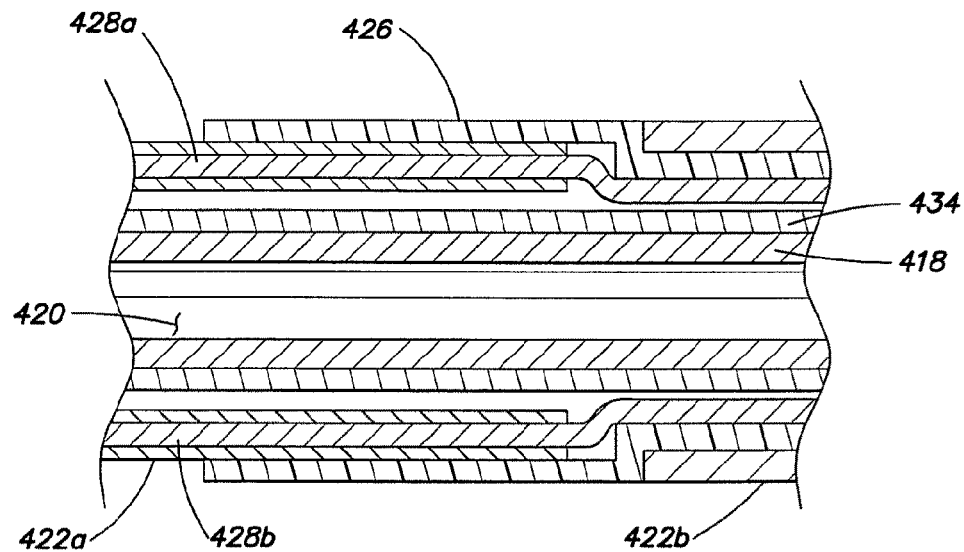

FIG. 41B illustrates an enlarged view of a portion of catheter 416 including counterbore 426. Counterbore 426 is located at a junction between the distal shaft portion 422a and the proximal shaft portion 422b and provides an interface between the two portions. The counterbore 426 may be formed of plastic, and may be substantially rigid to reduce the strain on the junction between the distal shaft portion 422a and the proximal shaft portion 422b. According to an embodiment of the invention, a bending point (or "knuckle") may be formed at the junction upon actuation of steering cables 428a-b.

Figure 41C:
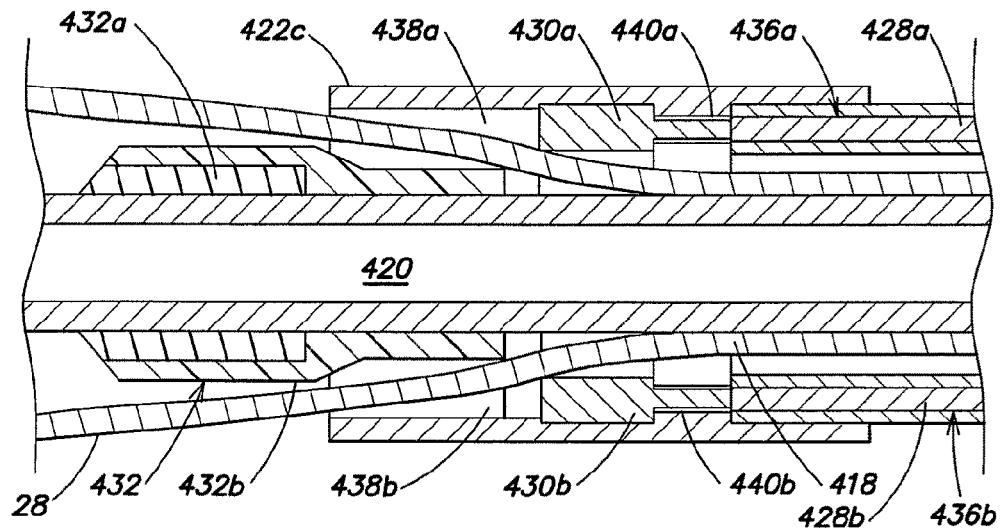

FIG. 41C illustrates an enlarged view of a portion of catheter 416 including seal 432 and steering anchors 430a-b. The seal 432 includes a first portion 432a and a second portion 432b. The second portion 432b is anchored to the anchor section 422c, for example using a bonding agent such as epoxy, a locking mechanism, or another mechanical connection. Alternatively, the second portion 432b may be integrally formed with a portion of the catheter 416. The second portion 432b may be formed of a plastic such as polyurethane, or another material suitable for forming a mechanical connection between the first portion 432a and the anchor section 422c. The first portion 432a is coupled to the second portion 432b, for example using a bonding agent. The first portion 432a may be formed of silicone, or another material suitable for forming a seal around mandrel 418. The seal formed may be wholly or substantially fluid-tight. In one example, the first and second portions 432a-b include inner surfaces constructed to allow the mandrel 418 to be slidably received therein. For example, the surfaces may be smooth and/or generate little friction when slid against a surface. However, it should be appreciated that the invention is not limited in this respect. For example, a lubricant or coating may be disposed on the inner surfaces to reduce the friction between the first and second portions 432a-b and the mandrel 418. It should also be appreciated that the seal 432 described above may have a number of alternate implementations. For example, the seal 432 may be formed of a single element and/or have a shape or configuration other than shown in FIGS. 41A and 41C.

Steering anchors 430a-b and steering cables 428a-b are configured in a manner similar to those shown in FIG. 37. In particular, anchors 430a-b have a width or diameter that is greater than the diameter of steering cables 428a-b. The anchors 430a-b may be integrally formed with the steering cables 428a-b or may be securely attached thereto. Steering cables 428a-b pass through lumens 436a-b, respectively, which extend along at least a portion of catheter 416. Lumens 436a-b respectively include larger width or diameter regions 438a-b and a smaller width or diameter regions 440a-b. Anchors 430a-b may be disposed in larger width or diameter regions 438a-b and may be sized such that the anchors do not fit within smaller width or diameter regions 440a-b. Accordingly, steering cables 428a-b may be anchored at the junction between regions 438a-b and 440a-b, respectively. A bonding agent such as epoxy may be provided to further inhibit movement of the anchors 430a-b.

Figure 41D:
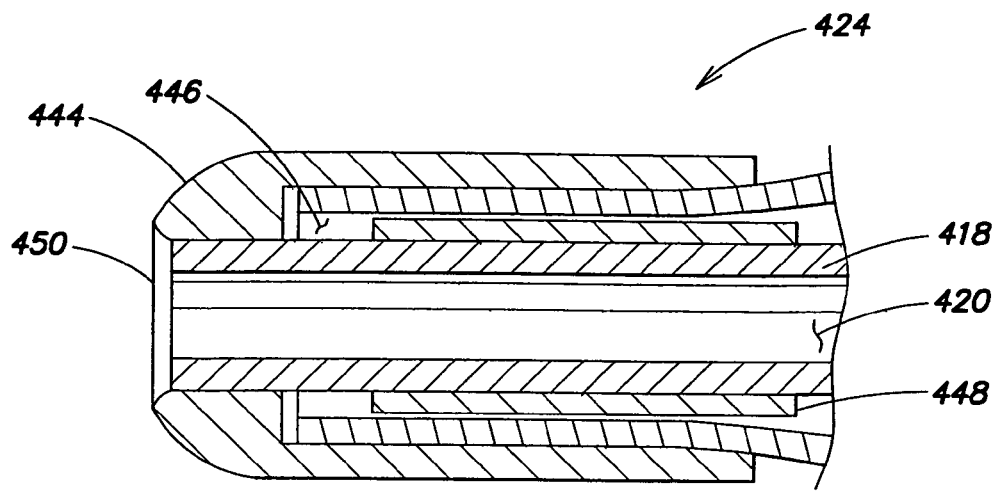
Figure 41E:
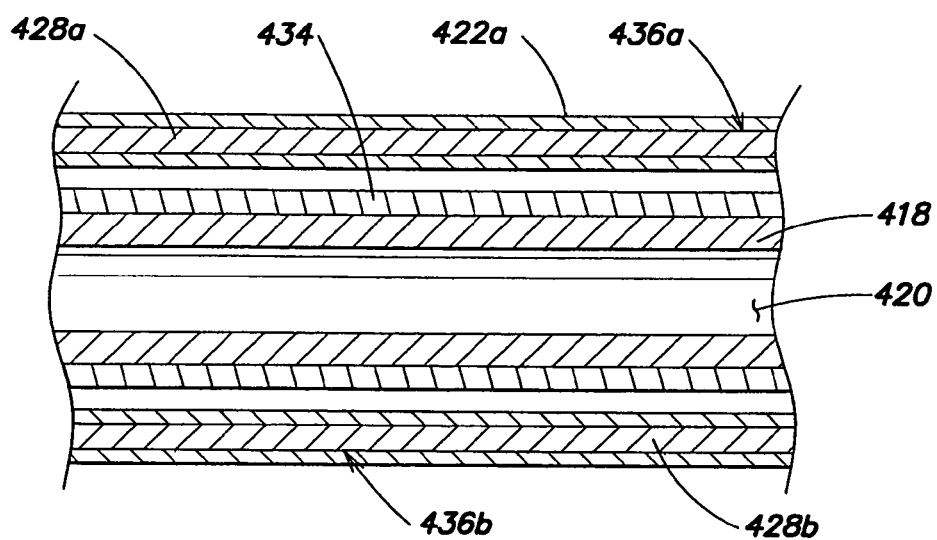

FIG. 41E illustrates an enlarged view of a portion of distal shaft portion 422a, including mandrel 418, steering cables 428a-b, and wires 434 used to form braided conductive member 28. As shown, steering cables 428a-b are disposed in lumens 436a-b formed in the wall of the distal shaft portion 422a. Mandrel 434 is disposed along a central longitudinal axis of shaft 422, and is surrounded by wires 434. The wires 434, which may be braided in the same manner as braided conductive member 28, are disposed in an opening between mandrel 418 and lumens 436a-b. It should be appreciated that the internal configuration of distal shaft portion 422a shown in FIG. 41E is merely exemplary, and that other configurations are possible. For example, lumens 436a-b may be absent, and both steering cables 428a-b and wires 434 may be disposed in an opening between mandrel 418 and an outer wall of the catheter shaft 422. In one implementation, steering cables 428a-b may be disposed at an inner radial position with respect to wires 434.

Mandrel 418 extends the length of the catheter 416 to a handle of the catheter. As shown in FIG. 41D, distal tip portion 424 includes a distal cap 444 coupled to the mandrel 418 at its most distal end. A distal end of braided conductive mesh 28 is circumferentially disposed about the mandrel 418 in a recess 446 between mandrel 418 and distal cap 444. In addition, a sleeve 448 is included between braided conductive member 28 and mandrel 418 in distal tip portion 424 to help to anchor the braided conductive member 28 within the distal cap 444. The sleeve 448 may be bonded to the mandrel 418, and the braided conductive member 28 may be bonded to the sleeve 448. In addition, a bonding agent may be included in recess 446 to provide additional fixation. Distal cap 444 may include an opening 450 in its distal tip to receive a distal opening of mandrel 418. As will be described in more detail below, the opening 450 in distal cap 444 may serve as a passageway for fluids or devices that passed to or from a patient's body during an electrophysiology procedure.

The mandrel 418 may be slidably disposed within the shaft 422, and may be moved along a longitudinal axis of the catheter 416 to actuate the braided conductive member 28. As described in connection with FIG. 41D, mandrel 418 and braided conductive member 28 are secured, at distal ends thereof, to distal cap portion 444. Hence, when the distal end of mandrel 418 is slid in a proximal direction within shaft 422, the distal tip portion 424 is moved towards shaft 422. The retraction motion of the distal tip portion 424 laterally compresses braided conductive member 28 and radially expands the outer diameter of the braided conductive member 28, thereby causing the braided conductive member 28 to assume a deployed configuration. Conversely, when the distal end of mandrel 418 is slid in a distal direction within shaft 422, the distal tip portion 424 is moved away from shaft 422. This causes braided conductive member 28 to radially compress and laterally expand so as to assume an undeployed configuration. In one example that will be described in connection with FIG. 42, the movement of mandrel 418 may be controlled using an actuator on a handle of the catheter 416. It should be appreciated that braided conductive member 28 may include any of the features described in connection with other braided conductive members disclosed herein.

According to one implementation, mandrel 418 has a substantially tubular shape and is formed of a plastic such as high durometer polyurethane. However, it should be appreciated that mandrel 418 may assume any shape that may extend along catheter 416 and accommodate an internal lumen. Further, mandrel 418 may be formed of alternative materials, such as nitinol or other alloys, and may be formed of or coated with a biocompatible material. Preferably, the mandrel 418 is constructed to resist kinking upon actuation of the mandrel in the distal direction. Accordingly, the stiffness of the mandrel material and the shape and thickness of the mandrel 418 itself may be selected so that the mandrel 418 is not susceptible to kinking. However, it is preferable that mandrel 418 be constructed to not unduly limit any steering capabilities of the catheter. Accordingly, the mandrel 418 may be bendable in a direction transverse to the longitudinal axis of the catheter under a force imposed by steering cables of the catheter.

Mandrel 418 may also be a multi-tiered mandrel, similar to the multi-tiered mandrel 400 of FIG. 39. For example, mandrel 418 may comprise two tiers having different outer diameters that join at a transition region. The diameter of lumen 420, however, may remain substantially constant.

Lumen 420 of mandrel 418 may be used to transport fluids or devices to or from the heart or vasculature of a patient during an electrophysiology procedure. For example, lumen 420 may be used to deliver an irrigation fluid such as saline to provide convective cooling during an ablation procedure. In =another example, example, lumen 420 may be used to deliver a contrast fluid, such as a fluoroscopic contrast agent, to verify the placement of braided conductive member 28 or changes in vessel diameter. In either ablation or mapping procedures, antithrombogenic fluids, such as heparin, may be delivered via lumen 420 to reduce thrombogenicity. Other medicines may also be delivered via lumen 420 for other treatment purposes. The fluids described above may be released from catheter 416 via the opening 450 discussed previously, or via one or more openings that may be formed in the sidewalls of mandrel 418. Fluids released via opening 450 may advantageously enter the blood flow of the patient upstream with respect to the mapping and/or ablating site, which aids in the visualization of the vascular structure where the catheter is to be placed and deployed.

In addition to, or as an alternative to being adapted for the transport of fluids, the lumen 420 of mandrel 418 may be adapted for the passage of medical devices. For example, lumen 420 may be used to introduce catheters, guidewires, and/or sensors (e.g., a blood pressure sensor, a pH sensor, a blood flow sensor, or an ultrasonic imaging device) into a patient. When catheter 416 is used in connection with a guidewire, the guidewire may be positioned first at a target site so that the catheter may follow the guidewire to the site. Alternatively, the guidewire may be inserted within mandrel 418 after the catheter 416 is introduced into the patient.

Figure 42:
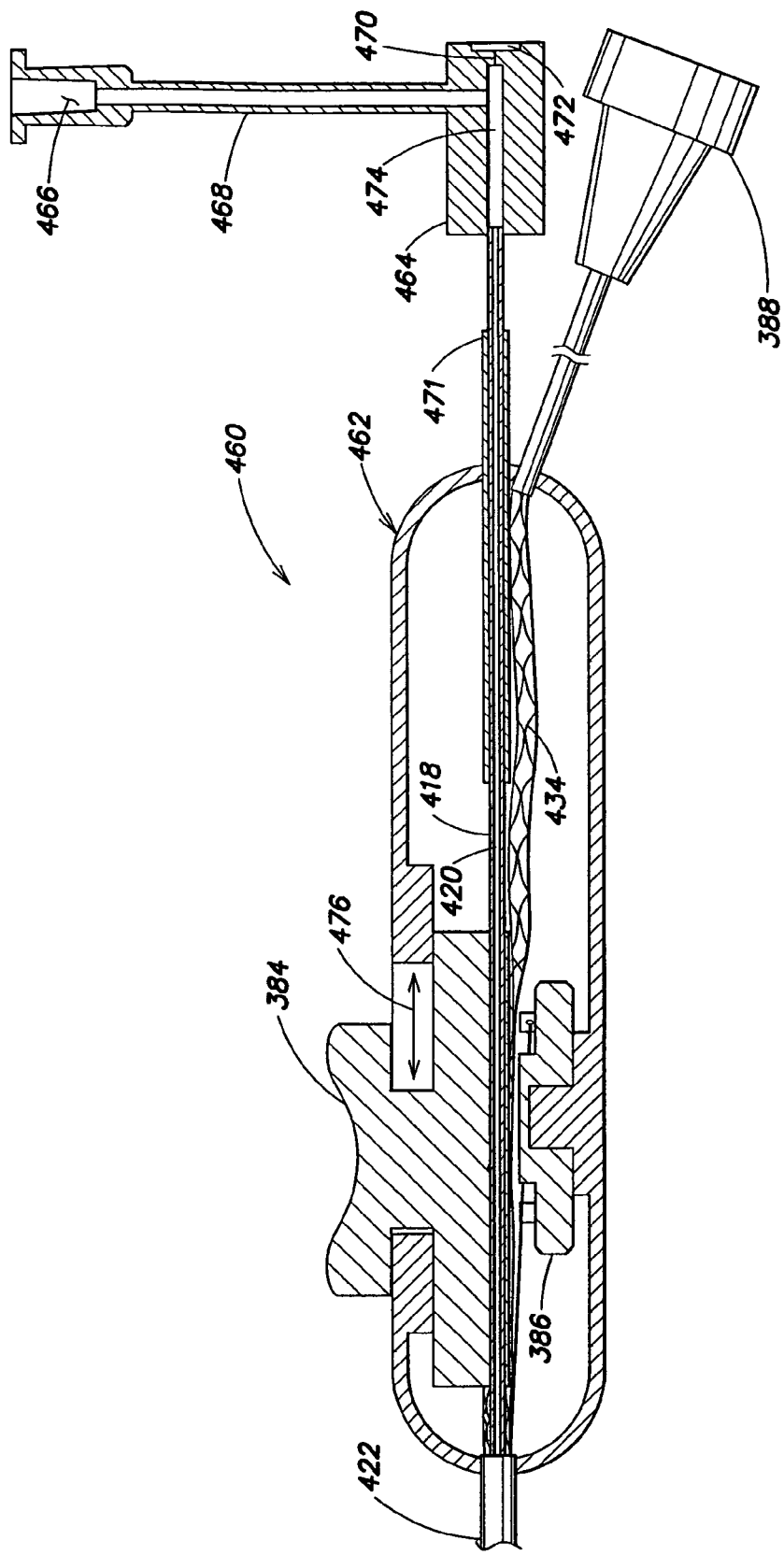

FIG. 42 illustrates an exemplary handle 460 that may be used to actuate mandrel 418. The handle 460 operates in the same manner as handle 380 discussed in connection with FIG. 38, with slide actuator 384 being coupled to mandrel 418 to actuate the mandrel. However, in this configuration, mandrel 418 extends out of handle housing 462 so that devices and/or fluids may be introduced into the lumen 420 of the mandrel 418. Channel 471, which is coupled to and partially disposed within housing 462, provides an opening through which mandrel 418 may slide.

Port 464 is coupled to the handle 460 to provide fluid or device access to the lumen 420 of mandrel 418. Fluids may be introduced via fluid opening 466, which is coupled to port 464 via tube 468. The port 464 may form a seal with the mandrel 418 to ensure the sterility of the injected fluids, and may be equipped with a valve (not shown) to control the passage of fluid. To provide device access to lumen 420, a device opening 470 is also provided in port 464. A silicone seal 472 may seal the device opening 470 such that fluids will not escape from device opening 470 if fluids and a device are simultaneously introduced via port 464.

Because mandrel 418 may be movable along a longitudinal axis of the catheter, the port 464 coupled to the handle 460 may also be movable. Alternatively, the port may be fixed with respect to the handle, and may not move in response to movement of the mandrel 418. Although many implementations are possible to achieve a fixed port, FIG. 42 shows an example in which port 464 has a lumen 474 to receive mandrel 418. Because the proximal end of mandrel 418 is slidably disposed within lumen 474, lumen 474 may have a length that is greater than a length 476 that slide actuator 384 may cause mandrel 418 to move.

Lesion Formation

One method for treating arrhythmia described herein involves the creation of a continuous, annular lesion at or near the ostium of a pulmonary vein. Such a lesion serves to block the propagation of the arrhythmia. However, as also described herein, a complete 'fence' around a circuit or tissue region is not always required in order to block the propagation of the arrhythmia. Rather, propagation of the arrhythmia may be halted or sufficiently diminished by one or more lesions, each only partially circumscribing an area of tissue traversed by errant signals.

For example, Applicants have appreciated that a complete or substantially complete conduction block may result when two or more generally arcuately shaped lesions are formed about a pulmonary vein or ostium thereof. According to one implementation, the lesions are concentrically formed about the pulmonary vein or ostium, although the invention is not limited in this respect. Preferably, the lesions are oriented such that at least one lesion intersects every direct path from the inside of the pulmonary vein to the atrium of the heart. For example, two or more discrete lesions may be formed that generally surround the pulmonary vein. One exemplary lesion pattern that may be formed to create a complete or substantially complete conduction block using concentrically formed lesions is illustrated in FIG. 43.

Figure 43:
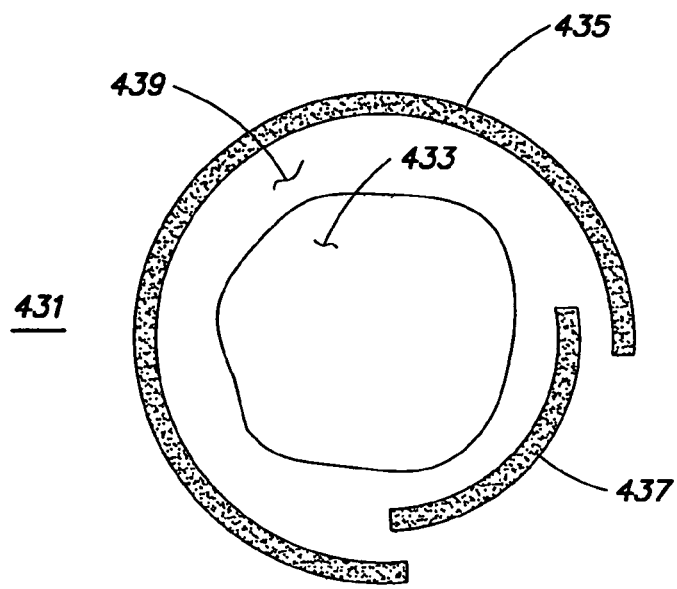
FIGS. 43-46 illustrate aspects of a braided conductive member according to another embodiment of the invention, and an exemplary lesion pattern formed by the braided conductive member.

FIG. 43 illustrates two lesions 435 and 437 formed in a region of cardiac tissue 439 that surrounds a pulmonary vein 433. Region 439 may be an ostium of pulmonary vein 433, for example, or a portion of the atrium of the heart that surrounds the ostium of the pulmonary vein. Lesions 435 and 437 are generally concentric, both with each other and with pulmonary vein 433. First lesion 435, which has a larger radius than second lesion 437, is located outside of lesion 437 and at a greater distance from pulmonary vein 433. Lesions 435 and 437 are arcuately shaped, and do not form, either individually or together, a closed circle. In the example of FIG. 43, first lesion 435 spans approximately 270° (i.e., its arc angle is 270°), and second lesion 437 spans greater than 90°. Second lesion 437 is located adjacent the opening of lesion 435, and has an arc angle that is larger than that of the opening of lesion 435. Thus, lesions 435 and 437 eliminate direct pathways for electrical signals traveling between the tissue of the pulmonary vein 433 and atrial tissue 431, as signals cannot cross region 439 without being diverted by lesion 435 or lesion 437. Thus, lesions 435 and 437 effect a complete or substantially complete conduction block that is sufficient to halt or sufficiently diminish the propagation of an arrhythmia.

It should be appreciated that the number, placement, size, and shape of the lesions shown in FIG. 43 is merely exemplary, as many configurations of discontinuous lesions may be envisioned that would similarly eliminate direct pathways for electrical signals traveling between the tissue of the pulmonary vein 433 and atrial tissue 431, such that a complete or substantially complete conduction block between the pulmonary vein 433 and atrial tissue 431 would be formed. For example, the angles specified for arcuate lesions 435 and 437 are merely exemplary, as other angles may alternatively be used. According to a preferred implementation, the angles of arcuate lesions forming the conduction block are selected so that the sum of the angles is greater than 360°. For example, one lesion may span approximately 180° and another adjacent lesion may span greater than 180°. To minimize damage to tissue, in another example, the sum of the angles of the lesions is greater than 360°, but less than 450°. It should also be appreciated that more than two lesions may be used, and that the configuration of the lesions may also be varied without departing from the invention. Further, although a pulmonary vein is illustrated and described, the method may be applied to other orifices or regions within the heart.

Figure 44:
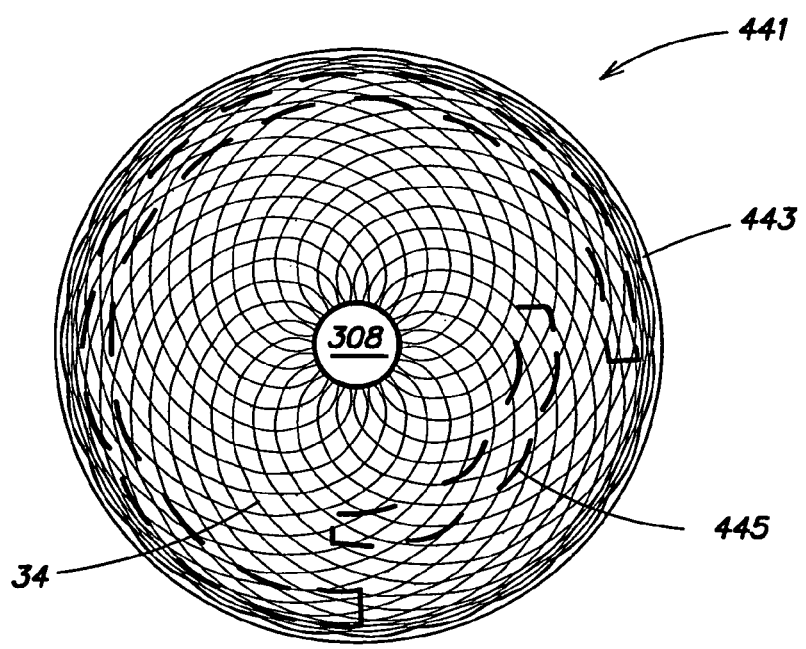

FIG. 44 illustrates an exemplary implementation of a braided conductive member 441 that that may be used to form the lesion pattern of FIG. 43. Braided conductive member 441 has the same structure as braided conductive member 28 described herein, but has a different pattern of uninsulated regions. Accordingly, braided conductive member 441 may be used in connection with any of the various catheter embodiments disclosed herein (e.g., catheter 10 of FIG. 1 and catheter 300 of FIGS. 34A and 34B).

Figure 45:
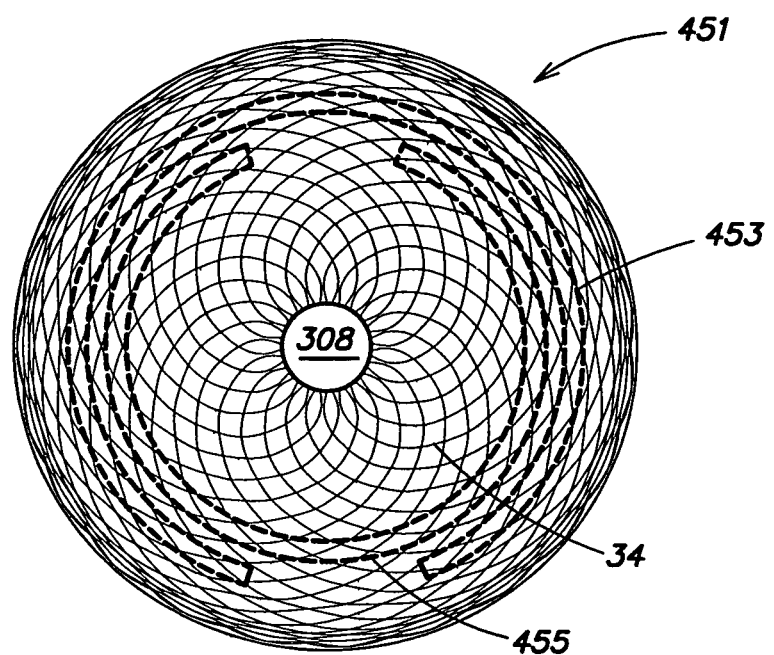

As in braided conductive member 28, braided conductive member 441 comprises a plurality of interlaced, electrically conductive filaments 34 surrounding a distal cap 308. Regions 443 and 445 designate areas where insulation has been removed on the outer circumferential surface 60 (see FIG. 7) or the entire circumferential surface of filaments 34 of braided conductive member 441. When braided conductive member 441 is fully energized with ablation energy, the ablation energy is transmitted to the tissue in a pattern that corresponds to the shape and orientation of regions 443 and 445. Other lesion patterns may be created by exposing areas of insulation on filaments 34 in a manner corresponding with the desired lesion pattern. For example, FIG. 45 illustrates a braided conductive mesh 451 having regions 453 and 455 of exposed insulation. Regions 453 and 455 are shaped like concentric horseshoes, and will form a corresponding lesion pattern when energized.

The principles described herein for providing zone control in braided conductive member 28 may also be applied to the braided conductive members of FIGS. 44 and 45. In particular, braided conductive members 441 and 451 may be divided into electrically independent sectors if desired. In the context of FIG. 44, one exemplary method of creating electrically independent sectors involves selecting a portion of the filaments 34 of braided conductive member 441 to deliver energy to the first region 445 and a different portion of the filaments 34 of braided conductive member 441 to deliver energy to the second region 443. Only those filaments that are delivering energy to a given region will have insulation exposed in that region. Thus, according to this exemplary method, not all of the filaments that pass through a region will have insulation exposed in that region. Further, exposed portions of filaments that deliver energy to first region 445 can be insulated from filaments that deliver energy to second region 443 to avoid shorting the different sectors together. Similar principles may be applied to the braided conductive member 451 of FIG. 45 to create electrically independent sectors.

One potential benefit of providing electrically independent sectors is that it allows energy to be delivered to just one region (e.g., first region 445 or second region 443). This may be desirable because, in some instances, ablation of a smaller portion of heart tissue than would be ablated if both regions were energized may be sufficient to treat an arrhythmia. If ablation of a smaller region is effective, it is desirable to ablate only the smaller region so as to minimize the area of tissue death. Another potential benefit of providing electrically independent sectors is that it allows energy to be delivered to regions (e.g., first region 445 or second region 443) at different levels. Controlling the energy applied to the different regions allows the amount of ablation energy delivered to more closely approximate the amount of energy necessary to achieve a satisfactory conduction block.

Figure 46:
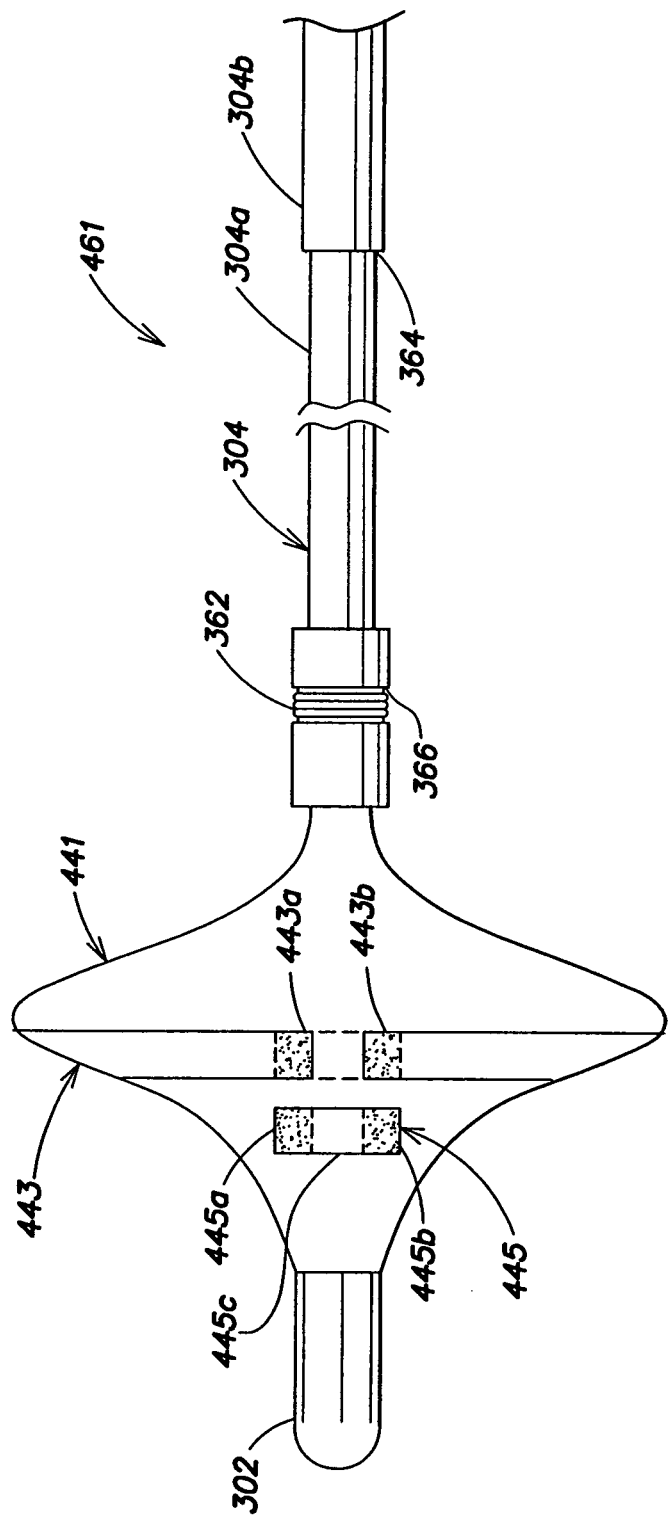

FIG. 46 illustrates a side view of a catheter 461, which is similar to the catheter of FIG. 34a, but has been modified to include the braided conductive member 441 shown in FIG. 44.

According to one exemplary implementation, the first and second regions 445, 443 of braided conductive member 441 may energized simultaneously, such that the lesion pattern shown in FIG. 43 may be formed by a single application or multiple applications of RF energy to regions 445 and 443.

According to another exemplary implementation, the first and second regions 445, 443 of braided conductive member 441 may energized individually, such that the lesion pattern shown in FIG. 43 is formed by at least two applications of RF energy. To energize the first and second regions 443, 445 individually, the principles described above for providing zone control may be applied. Thus, a first group of filaments having insulation exposed within the second region 443 may be energized independently from a second group of filaments having insulation exposed within the first region 445. For example, to energize first region 445 independently from second region 443, filaments in regions 445a-c are energized. Region 445c does not include any filaments common to region 443; thus, all of the filaments that traverse region 445c may have insulation exposed in region 445c and may be energized. Regions 445a and 445b, on the other hand, include filaments common to regions 443a and 443b, respectively. To make region 445a independently energizable with respect to region 443a, a first group of filaments traversing regions 445a and 443a may have their insulation exposed only in region 445a; a second group of filaments traversing regions 445a and 443a, different from the first group, may have their insulation exposed only in region 443a. Similarly, to make region 445b independently energizable with respect to region 443b, a first group of filaments traversing regions 445b and 443b may have their insulation exposed only in region 445b; a second group of filaments traversing regions 445a and 443b, different from the first group, may have their insulation exposed only in region 443b. According to one example, the first groups of filaments may comprise filaments that are interleaved with filaments of the second groups of filaments. In view of the foregoing, it may be appreciated that to energize only first region 445, filaments in region 445c may be energized, along with the first groups of filaments in regions 445a and 445b.

Inflatable Balloons

As discussed herein, the braided conductive member 28 of the catheters described herein may be used to create an annular lesion at or around the ostium of a pulmonary vein or other orifice. Because of the movement of the contracting heart and the uneven surface of the endocardial tissue, it can be difficult to make sufficient contact between the braided conductive member 28 and a region of tissue for formation of a desired lesion at the region. Additionally, asymmetry of pulmonary veins, which may be oval rather than circular, may limit contact and consequently ablation. To enhance tissue contact, the interior of the braided conductive member 28 may be provided with a means for applying a force to the braided conductive member 28. For example, the interior of the braided conductive member 28 may be provided with inflatable balloons for applying a force to the braided conductive member 28.

Figure 47:
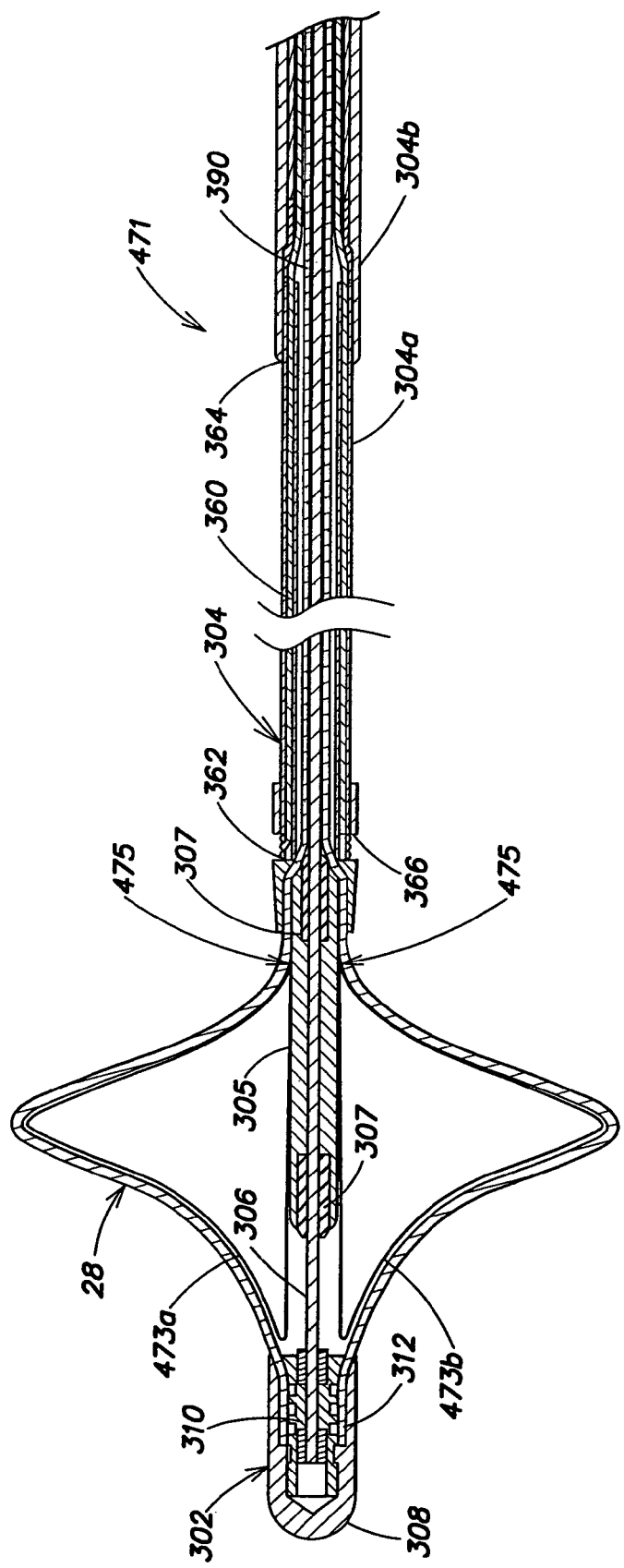
FIGS. 47-49 illustrate catheters comprising inflatable balloons according to various embodiments of the invention.
Figure 48:
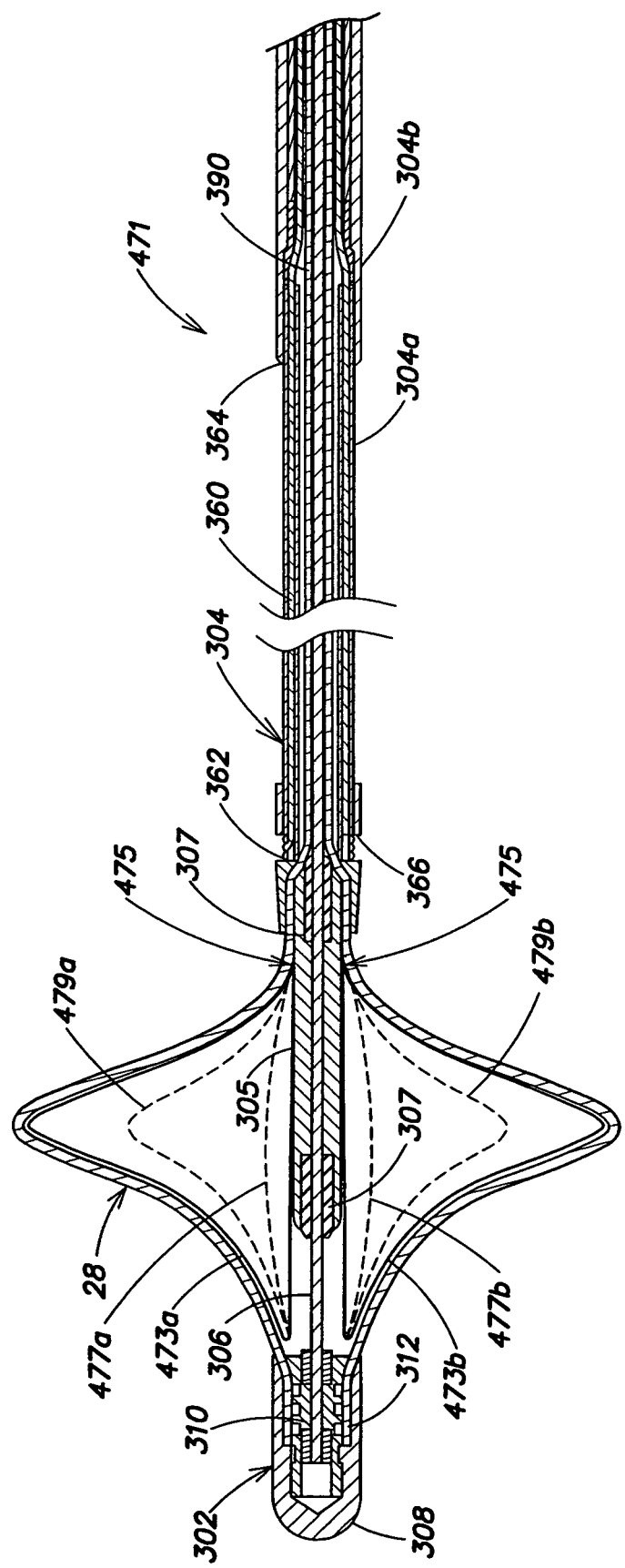

A first embodiment of a catheter having inflatable balloons provided within the braided conductive member 28 is shown in FIGS. 47-48. The catheter 471 of FIGS. 47-48 is similar to the catheter 300 shown in FIG. 34B but includes first and second inflatable balloons 473a,b. The inflatable balloons 473 are disposed within the braided conductive member 28. The balloons may be sized and shaped to correspond to the shape of the braided conductive member 28 in the fully or partially deployed position. Other sizes and/or shapes may alternatively be used. For example, the balloons may be sized and shaped to have an outer periphery that is larger than the outer periphery of the braided conductive member 28 in the fully or partially deployed position, so that the balloons exert outward pressure on the braided conductive member 28. In addition to preferentially providing contact pressure on the side of the catheter opposite the balloon, blood flow will be directed to the deflated side, favorably cooling the ablative electrodes, as discussed further below. To keep the inflatable balloons 473 properly positioned within the braided conductive member 28, the balloons may be fixedly attached to strain relief portion 305 as shown in FIG. 47.

The inflatable balloons 473 may be formed of a latex balloon material or another suitable material. It may be desirable to form inflatable balloons 473 from a material resistant to thrombi formation and durable enough to withstand both outwardly directed and inwardly directed pressure. The balloons 473 may be inflated using a saline solution, or using another liquid or gaseous medium. The inflation medium may be radio-opaque for visibility. Preferably, the inflation medium is biocompatible, so as to avoid medical complications in the event of accidental leakage.

To conduct the inflation medium to the balloons, lumens may be provided within the catheter shaft 304. The lumens may be located within the shaft between the wires of the braided conductive member and the mandrel 306. There may be one lumen for each of the first and second balloons 473. Alternatively, a plurality of lumens may supply inflation medium to each balloon. Each lumen may be coupled to its corresponding inflatable balloon 473 at a proximal portions 475 thereof or another location. To introduce the inflation medium into the lumens, a port similar to port 464 of FIG. 42 may be used. The port may be coupled to the lumens, for example via an intermediate branched tubing structure.

FIG. 48 illustrates the inflation of the balloons 473a,b from an uninflated position, represented by lines 477a,b, to a partially inflated position, represented by lines 479a,b, to a fully inflated position. The balloons 473 may be inflated manually, for example using a syringe that introduces an inflation medium into the lumens via the port described above. Alternatively, the balloons may be inflated automatically, for example using an automated pump coupled to the port. The balloons 473 may be deflated in the same manner. The balloons 473 may be independently inflatable so that the balloons may be simultaneously inflated to different degrees.

Figure 49:
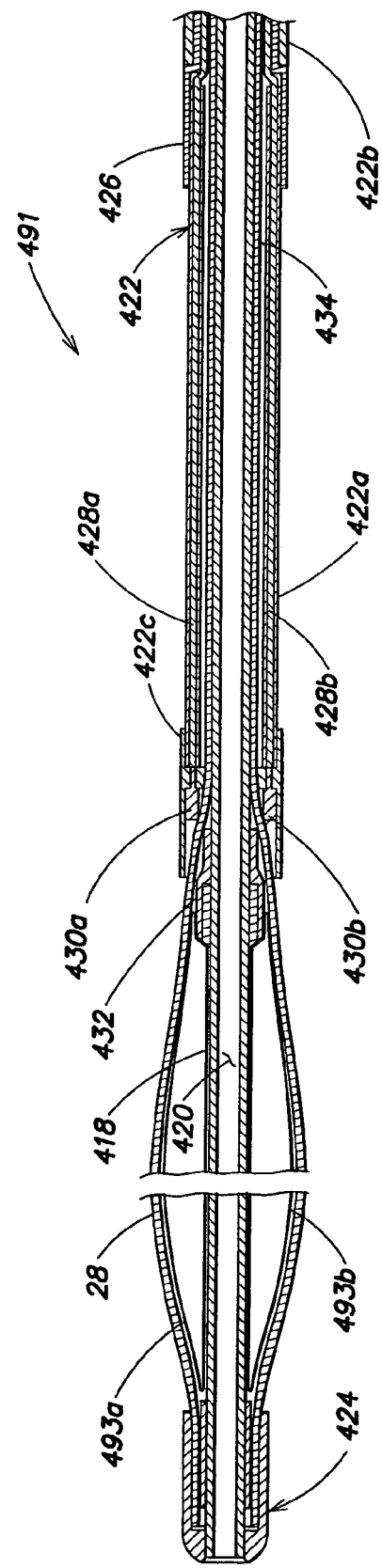

Another embodiment of a catheter having inflatable balloons provided within the braided conductive member 28 is shown in FIG. 49. The catheter 491 of FIG. 49 is similar to the catheter 416 shown in FIG. 41A but includes first and second inflatable balloons 493a,b. The balloons 493 may be constructed and used in the manner described in connection with FIGS. 47-48. Catheter 491 includes a mandrel 418 having an interior lumen 420. Many uses for the interior lumen 420 of mandrel 418 have been described herein. Many of these uses may be advantageously implemented in connection with the balloons 493.

For example, according to one exemplary method of using catheter 491, the braided conductive member 28 may be fully deployed and positioned adjacent tissue at or about an orifice. Both of the first and second balloons 493 may then be inflated to obstruct the orifice and substantially prevent the passage of fluids therethrough. A radio-opaque contrast agent may then be released from the lumen 420 of the mandrel 418. When the contrast agent is viewed under fluoroscopy, regions where the contrast agent passes from the vessel side of the orifice to the catheter side of the orifice past one or more of balloons 493 may be observed. In this manner, locations where sufficient contact is not made between the braided conductive member 28 and the region of tissue may be identified, and the contact may be improved by increasing the pressure applied to the braided conductive member 28 in those areas. Alternatively, an ultrasonic imaging device can be passed through the central lumen and used to assess contact.

One method of improving the contact in a certain region of tissue in the vicinity of the orifice is to inflate the first and second balloons 493 to different degrees. For example, once a location of insufficient contact is identified (e.g., using the fluoroscopic method described above or another method), the balloon adjacent to that location is inflated to a lesser degree than the opposite balloon. For example, the balloon adjacent to that location may be fully deflated and the balloon opposite the adjacent balloon may be fully inflated. The inflation to a greater degree of the balloon opposite the balloon adjacent to the location of insufficient contact urges the braided conductive member 28 in closer contact with the tissue at the location.

The method of improving the contact in a certain region of tissue described above may result in improved lesion formation. This may be accomplished not only from the improved contact between the braided conductive member 28 and the region of tissue, but also from increased blood flood across the region of tissue. In particular, when the balloon corresponding to the location of insufficient contact is inflated to a lesser degree than the opposite balloon, a smaller passage for the flow of blood is created than if the blood were flowing normally through the orifice. For example, if one balloon is fully inflated and one balloon is fully deflated, the ordinary cross sectional area of the orifice through which blood may pass is decreased by approximately half. This decrease in area results in a corresponding increased rate of flow of blood through the orifice. The increased rate of flow across the region of tissue increases the cooling of this tissue, and thereby improves lesion formation.

Although only two balloons are incorporated within the braided conductive member 28 described in connection with the embodiments of FIGS. 47-49, other numbers of balloons may alternatively be used. For example, three, four, five, or six balloons, of approximate equal sizes and dimensions may be disposed within the braided conductive member 28 at approximately equally spaced intervals. Each balloon may be independently inflatable in the manner described above. By incorporating a greater number of balloons within the braided conductive member 28, a greater degree of control in selecting a location to increase tissue contact and/or blood flow is afforded.

Further, although the balloons 493 are described as advantageously containing contrast fluid in a vessel when the balloons are inflated, the balloons may serve a similar function with respect to other fluids. For example, the balloons may contain drugs or other diagnostic or treatment fluids in the region substantially or fully sealed by the balloons. In this manner, the drugs or other diagnostic or treatment fluids can be retained in the vessel for a period of time needed to be effective.

Pressure Sensitive Wires

A method of assessing the contact of the braided mesh electrode 28 using a contrast agent was discussed above in connection with the inflatable balloons 492. However, a method of assessing contact that does not rely on the balloons 492 and a contrast agent may be desirable. Accordingly, in the embodiment described below, the braided conductive member 28 is provided with pressure sensitive wires to assess the contact of at least a portion of the braided conductive member 28 with adjacent tissue.

Figure 50:
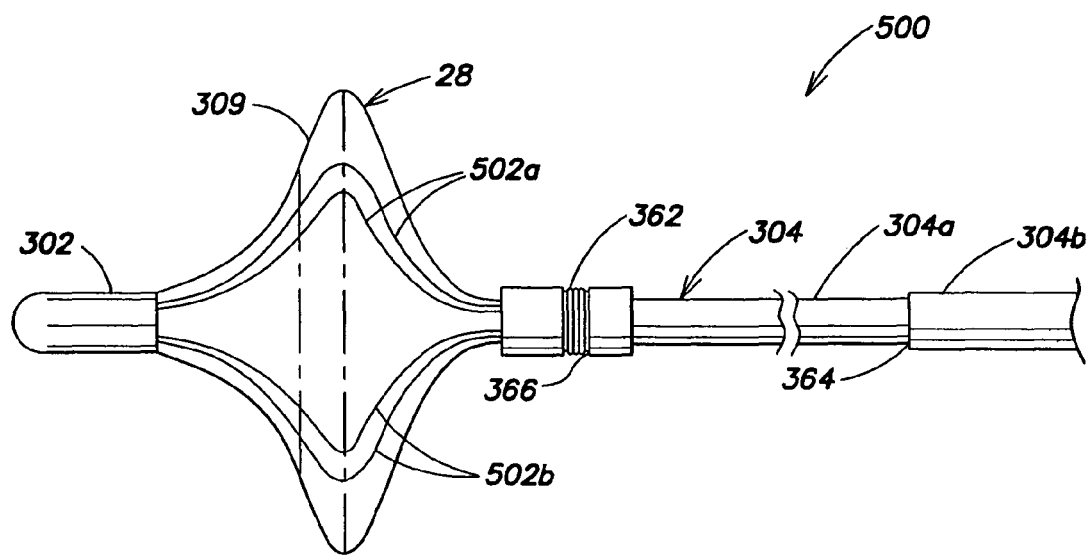
FIGS. 50-55 illustrate catheters comprising pressure sensitive wires according to various embodiments of the invention.
Figure 51:
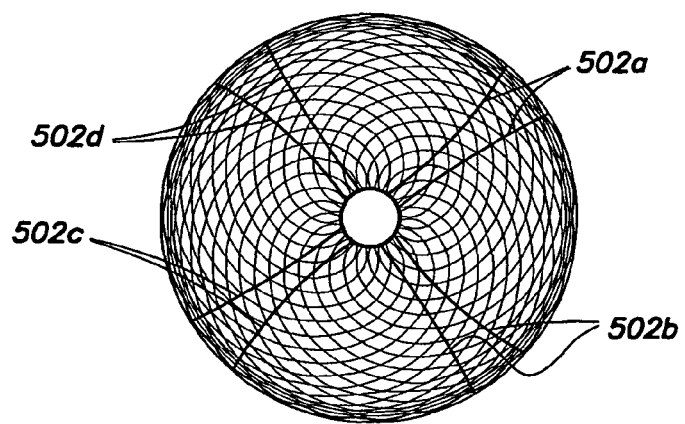

A first embodiment of a catheter 500 having pressure sensitive wires is shown in FIGS. 50-51. FIG. 50 illustrates a side view of a distal portion of catheter 500, while FIG. 51 illustrates an end view of the catheter 500. The catheter 500 of FIGS. 50-51 is similar to the catheter 300 shown in FIG. 34A but includes pressure sensitive wires 502 $a$-$d$ woven into the braided conductive member 28. By including a plurality of pressure sensitive wires 502 $a$-$d$, the contact of each portion of the braided conductive member 28 with the tissue may be assessed. According to one exemplary implementation, the pressure sensitive wires 502 $a$-$d$ are comprised of a piezoresistive material. Such materials exhibit a change in the electrical resistance of the material due to an applied mechanical stress. The pressure sensitive wires 502 $a$-$d$ may comprise silicon carbide, gallium arsenide, or another piezoresistive material. Preferably, the pressure sensitive wires 502 $a$-$d$ have a piezoresistive coefficient that is sufficient to reliably indicate tissue contact. Alternatively, the pressure sensitive wires may be formed of another material that is responsive to pressure. For example, the pressure sensitive wires may be formed of a material that generates an electrical change in response to pressure (e.g., a piezoelectric material) or a material that exhibits a change in capacitance in response to a change in pressure. Other non-wire pressure transducers may also be incorporated into the braided conductive member 28 in a similar manner. For example, an optical pressure transducer may be used.

The pressure sensitive wires 502 $a$-$d$ may be round, and have a diameter approximately equal to that of the filaments of the braided conductive member 28, for example approximately 0.001-0.030 inches in diameter. Alternatively, the pressure sensitive wires 502 $a$-$d$ may be flat, having a thickness on the order of about 0.001-0.030 inches, and a width on the order of about 0.001-0.030 inches.

According to one exemplary implementation shown in FIGS. 50-51, the pressure sensitive wires 502 $a$-$d$ may be woven into the braided conductive member. The pressure sensitive wires 502 may be coupled to controller 8 (FIG. 1) and pass through shaft 304 along with the wires of the braided conductive member 28. According to a first example, shown in FIG. 50, each pressure sensitive wire 502 may form a loop that runs to the distal tip of the catheter 500 and back towards the handle via the shaft 304.

When the pressure sensitive wire 502 comes into contact with tissue, the resistance of the wire changes. Thus, when a current is passed through the pressure sensitive wire 502, a change in the voltage across the wire, and hence in the resistance of the wire, is observed relative to the resistance of the wire when the pressure sensitive wire 502 is not in contact with tissue. The magnitude of this change indicates the amount of stress on the pressure sensitive wire 502, and therefore indicates tissue contact. To determine the relative change in the resistance of the wire, baseline measurements may be taken by passing a current through the pressure sensitive wire 502 at times when the pressure sensitive wire 502 is known to not be contacting any tissue, e.g., when the pressure sensitive wire 502 is within the atrium and not in contact with any walls thereof. Controller 8 and/or recording device 2 (FIG. 1) may be used to provide the current to the pressure sensitive wire 502, measure the voltage across the pressure sensitive wire, and calculate the resistance of the pressure sensitive wire 502. To allow for precise measurement of the resistance of the pressure sensitive wire 502, a Wheatstone bridge or another electric circuit for the comparison of resistances may be incorporated within the controller 8 or recording device 2 and coupled to the pressure sensitive wire 502.

The catheter 500 includes four looped pressure sensitive wires 502 *a-d*, each disposed in one of four sectors of the braided conductive member 28. However, this arrangement is merely exemplary. Other numbers of pressure sensitive wires, e.g., one, two, three, five, six, seven, or eight or more, are also possible. In the case where a plurality of pressure sensitive wires are used, the wires may be evenly distributed within the braided conductive member. Further, in the case where a plurality of pressure sensitive wires are used, each wire may be disposed in its own electrically independent sector. Of course, it should be appreciated that such examples are merely exemplary and that other configurations are possible. For example, the pressure sensitive wires may not be evenly distributed, and need not be arranged as shown in FIGS. 50-51. According to another example, pressure sensitive wires may be arranged to form one or more circles concentric with distal tip portion 302 on the distally facing portion of braided conductive member 28.

To assist the physician or other medical professional in assessing the contact of one or more portions of the braided conductive member, a display may be provided. The display may indicate the change in resistance of each pressure sensitive wire 502 relative to the baseline measurement(s). The display may also include graphics or other visual aids to assist the physician in associating each change in resistance with the corresponding location of the pressure sensitive wire on the braided conductive member 28. For example, the display may show an image representing the braided conductive member and represent the change in resistances in the image (e.g., using colors, numbers, lines, or other indications). The average value of the change in resistance of each pressure sensitive wire 502 may also be calculated and/or displayed. Further, the change in resistance of each pressure sensitive wire relative to this average may be calculated and/or displayed.

Figure 52:
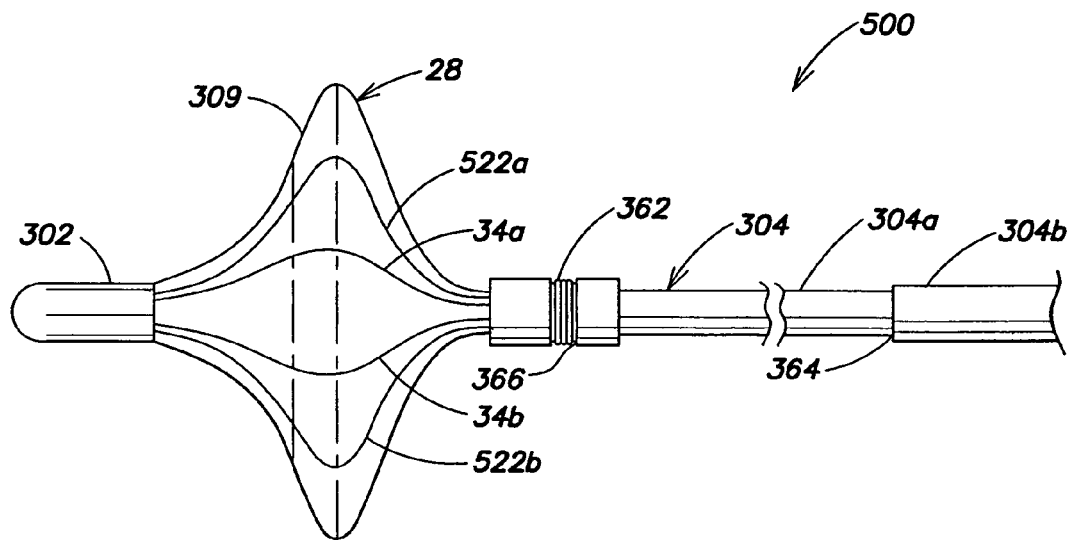
Figure 53:
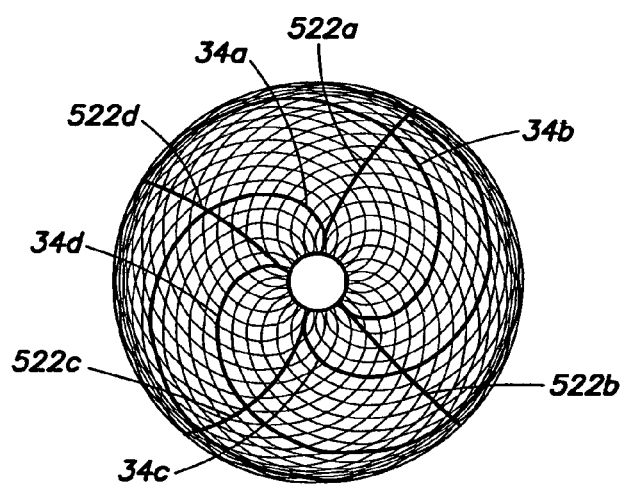

As discussed in connection with FIGS. 50-51, a pressure sensitive wire 502 may form a loop that runs to the distal tip of the catheter 500 and back towards the handle via the shaft 304. According to another example, shown in FIGS. 52-53, each pressure sensitive wire 522 may be electrically coupled to a filament 34 of the braided conductive member 28, e.g., at the distal tip portion 302 of the catheter. Thus, the pressure sensitive wire 522 and the filament 34 together form a loop that runs to the distal tip of the catheter 520 and back towards the handle via the shaft 304. The methods and configurations explained in connection with FIGS. 50-51 may also be used in connection with this embodiment. In particular, to assess the contact of the pressure sensitive wires 522 *a-d* with the tissue, the change in voltage across the loop as a whole, including pressure sensitive wire 522 *a-d* and respective filament 34 *a-d*, may be assessed. Filaments 34 may be used for mapping and ablation purposes, as described herein, in addition to their function described above.

Figure 54:
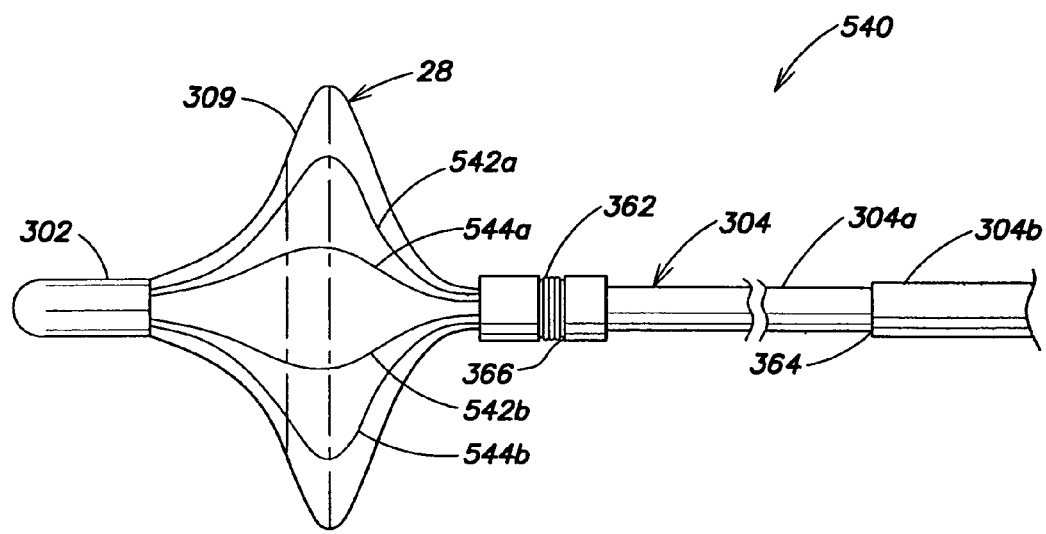
Figure 55:
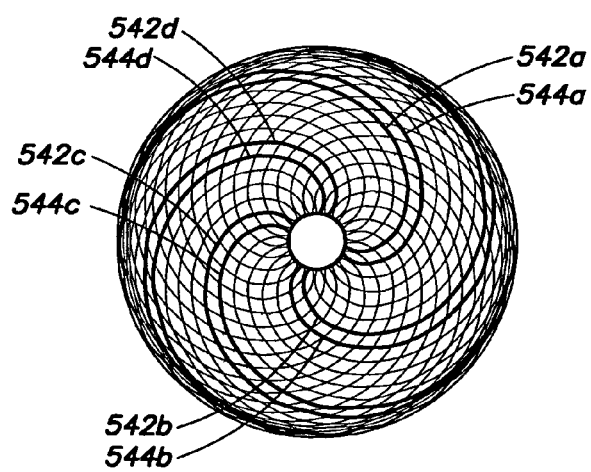

According to a further example, shown in FIGS. 54-55, the pressure sensitive wires themselves may comprise filaments of the braided conductive member 28. In particular, pressure sensitive wires 542 *a-d* may be used in place of the filaments 34 of braided conductive member 28. Each pressure sensitive wire 542 may be usable to detect and/or apply electrical energy as well as to detect a stress or pressure on the wire. As discussed in connection with other embodiments, each pressure sensitive wire may form a loop that runs to the distal tip of the catheter and back towards the handle via the shaft. Thus, filaments 544 *a-d*, each of which is respectively coupled to a corresponding one of pressure sensitive wires 542 *a-d* in the distal tip portion 302, may likewise comprise a pressure sensitive wire. Alternatively, filaments 544 *a-d* may comprise a conventional filament, such as filaments 34 described herein, that are not formed of a material responsive to pressure. The methods and configurations explained in connection with FIGS. 50-51 may also be used in connection with this embodiment.

In the embodiments described above, the resistance of a pressure sensitive wire is determined by measuring a voltage between two ends of a pressure sensitive wire or between an end of a pressure sensitive wire and an end of a filament coupled thereto. However, the invention is not limited in this respect. For example, the filaments 544 *a-d* of FIGS. 54-55 may be omitted such that the pressure sensitive wire 542 may only be electrically coupled via the catheter 540 to the controller 8 (FIG. 1) at one end thereof. To measure the resistance of the pressure sensitive wire 542, a current in the form of a square wave) may be passed through the pressure sensitive wire that then travels through the body of a patient and to a reference electrode. The voltage between the reference electrode and the pressure sensitive wire 542 may thus provide an indication of the resistance of the pressure sensitive wire. Changes in this resistance provide an indication of stress on the pressure sensitive wire 542, and therefore contact of the pressure sensitive wire with tissue, in the manner described above. Rings of pressure sensitive wire (like circles of latitude) or a tip sensor (e.g. on distal tip portion 302 or on braided conductive member 28) may be used to assess forward contact pressure. In the embodiment of FIGS. 16A-16C and other "noseless" braided conductive member configurations, such rings of pressure sensitive wires may be particularly advantageous.

Catheter Having Pressure Sensitive Wires and/or Inflatable Balloons

Methods of using a catheter having pressure sensitive wires and/or inflatable balloons will now be described. The braided conductive member 28 of any of the catheters of FIGS. 50-55 may be used to form one or more lesions that create a circumferential conduction block around an orifice, such as an orifice of a pulmonary vein. Prior to forming a lesion, the pressure sensitive wires of such catheters may be used to determine whether a certain degree of contact exists between the braided conductive member 28 and the region of tissue about the orifice. In particular, a pressure sensitive wire may be disposed in each of a plurality of sectors (e.g., quadrants) of the distally facing surface of the braided conductive member 28, and these pressure sensitive wires may be used to determine a degree of contact between each sector of the braided conductive member 28 and the region of tissue about the orifice.

Optionally, an indicator on the catheter, controller, or other unit may provide an indication of the degree of contact between each sector of the braided conductive member 28 and the region of tissue about the orifice. Alternatively or additionally, an indicator on the catheter, controller, or other unit may provide an indication of whether the degree of contact between each sector of the braided conductive member 28 and the region of tissue about the orifice has exceeded a predetermined threshold. For example, the catheter handle may include a light emitting diode (LED) that is illuminated when the degree of contact between one, some, or all sectors of the braided conductive member 28 and the region of tissue about the orifice has exceeded a predetermined threshold deemed acceptable for successful lesion formation. As another example, the controller may generate a sound indicating that the threshold has been exceeded. Alternatively or additionally, the controller may automatically adjust balloon pressure to ensure contact using pressure information from the pressure sensitive wires.

When a determination is made that the degree of contact between a sector of the braided conductive member 28 and a region of tissue about the orifice has exceeded a predetermined threshold deemed acceptable for successful lesion formation, a physician or other individual may cause that sector of the braided conductive member 28 to be energized with ablation energy. Alternatively, when a determination is made that the degree of contact between a sector of the braided conductive member 28 and a region of tissue about the orifice has exceeded a predetermined threshold deemed acceptable for successful lesion formation, that sector of the braided conductive member 28 may be energized automatically, i.e., without human intervention. Sectors of the braided conductive member 28 may be separately energized by delivering energy to electrically independent sectors, as described herein. Although sectors may advantageously be used to localize energy delivery, it should be appreciated that the methods described above may be used with a braided conductive member 28 having no sectors. Similarly, this process may be automated with the use of automatic adjustment of balloon inflation to adjust contact pressure.

After lesion formation, the braided conductive member 28 may be used in a mapping mode to detect signals from the tissue in the region of the lesion formation. If the braided conductive member 28 detects weak signals or does not detect any signals, this may be an indication either that a conduction block has been successfully formed in the tissue or that poor contact exists between the braided conductive member 28 and the tissue. Thus, to confirm a successful conduction block, the controller 8 (FIG. 1) may be programmed or otherwise configured to determine whether the braided conductive member 28 has detected a signal level (e.g., voltage) below a predetermined threshold while making sufficient contact with the tissue (e.g., as indicted by signals from pressure sensitive wires that are above a predetermined threshold). If the algorithm yields a positive result, i.e., both conditions are true, an indication of successful ablation may be provided. For example, a green LED may be illuminated on the catheter and/or controller.

On the other hand, if a determination is made, by an individual or automatically, that the degree of contact between a sector of the braided conductive member 28 and a region of tissue about the orifice has not exceeded a predetermined threshold deemed acceptable for successful lesion formation, that sector of the braided conductive member 28 may be caused to come into closer contact with the region of tissue. For example, in response to such a determination, an inflatable balloon in the braided conductive member 28, such as those described in connection with FIGS. 47-49, may be inflated by an individual or automatically. The inflation of the balloon urges the sector of the braided conductive member 28 into closer contact with the region of tissue in the manner described herein.

Furthermore, if a determination is made that the degree of contact between a sector of the braided conductive member 28 and a region of tissue about the orifice has not exceeded a predetermined threshold deemed acceptable for successful lesion formation, a lockout mechanism may be used to prevent the application of ablation energy to the braided conductive member 28. For example, the controller 8 may be programmed to prevent ablation energy 4 from transmitting ablation energy to the catheter when the controller has determined that a sufficient level of contact is not being made between a region of tissue and one or more (e.g., all) sectors of the braided conductive member 28.

It should be appreciated that any combination of the features described in connection with FIGS. 47-55 may be advantageously employed with other catheter features or electrophysiology procedures described herein. Further, it should be appreciated that these features may be used with other types of catheters.

Having thus described at least one illustrative embodiment of the invention, various alterations, modifications, and improvements will readily occur to those skilled in the art. For example, one skilled in the art will appreciate that each of the above described features may be selectively combined into a method of use and/or a device depending on, for example, the function desired to be carried out. Such alterations, modifications, and improvements are intended to be within the spirit and scope of the invention. Accordingly, the foregoing description is by way of example only and is not intended as limiting. The invention is limited only as defined in the following claims and the equivalents thereto.

What is claimed:

1. An electrophysiology catheter comprising:
   a handle;
   a shaft coupled to a distal end of the handle; and
   a braided conductive member coupled to a distal end of the shaft,
   wherein the braided conductive member comprises a plurality of pressure sensitive wires and a plurality of sectors including a first sector and a second sector,
   wherein the first sector comprises at least a first pressure sensitive wire for sensing a first degree of pressure between the first sector and first adjacent tissue, and
   wherein the second sector comprises at least a second pressure sensitive wire for sensing a second degree of pressure between the second sector and second adjacent tissue.

2. The electrophysiology catheter of claim 1, wherein the plurality of pressure sensitive wires are disposed at least partially in a distally facing surface of the braided conductive member.

3. The electrophysiology catheter of claim 1, wherein the plurality of pressure sensitive wires are woven into the braided conductive member.

4. The electrophysiology catheter of claim 1, wherein the impedance of the plurality of pressure sensitive wires varies in response to the pressure applied to the wires.

5. The electrophysiology catheter of claim 1, wherein each of the plurality of sectors comprises at least one of the plurality of pressure sensitive wires.

6. The electrophysiology catheter of claim 5, wherein each of the plurality of sectors is electrically independent.

7. The electrophysiology catheter of claim 5, further comprising an indicator coupled to one or more of the pressure sensitive wires, and wherein the indicator is adapted to indicate whether the degree of pressure on one or more of the plurality of sectors has exceeded a predetermined threshold.

8. The electrophysiology catheter of claim 7, wherein the indicator comprises a light emitting diode (LED).

9. The electrophysiology catheter of claim 1, further comprising a balloon assembly constructed and arranged to selectively apply distal pressure to one or more sectors of the braided conductive member.

10. The electrophysiology catheter of claim 9, wherein the balloon assembly is disposed in an interior space formed by the braided conductive member.

11. The electrophysiology catheter of claim 9, wherein the catheter is adapted to automatically adjust an inflation of all or a portion of the balloon assembly in response to an indication of pressure received from one or more of the plurality of pressure sensitive wires.

12. A system, comprising:
the catheter of claim 1; and
a controller coupled thereto.

13. The system of claim 12, wherein the controller is adapted to indicate whether the degree of pressure on one or more of the plurality of sectors has exceeded a predetermined threshold.

14. The system of claim 12, wherein:
the controller comprises an ablation energy generator; and
the controller is adapted to determine if pressure detected by at least one of the plurality of pressure sensitive wires is below a predetermined threshold and prohibit application of ablation energy to at least a portion of the braided conductive member if the pressure is below the predetermined threshold.

15. The system of claim 12, wherein:
the controller comprises an ablation energy generator; and
the controller is adapted to determine if pressure detected by at least one of the plurality of pressure sensitive wires is above a predetermined threshold and automatically apply ablation energy to at least a portion of the braided conductive member if the pressure is above the predetermined threshold.

16. The system of claim 12, wherein:
the catheter further comprises a balloon assembly constructed and arranged to selectively apply distal pressure to one or more sectors of the braided conductive member;
wherein the controller further comprises an inflation mechanism adapted to automatically adjust an inflation of the balloon assembly in response to at least one signal received from the plurality of pressure sensitive wires.

17. The system of claim 12, wherein:
the controller comprises an ablation energy generator; and
the controller is adapted to apply ablation energy to the pressure sensitive wires.

18. The system of claim 12, wherein:
the controller comprises a recording device; and
the controller is adapted to transmit mapping signals from the pressure sensitive wires to the recording device.

19. A method, comprising:
introducing a catheter having a braided conductive member into a heart, the braided conductive member comprising a plurality of sectors including a first sector comprising at least a first pressure sensitive wire and a second sector comprising at least a second pressure sensitive wire;
positioning the braided conductive member at a desired location for performing ablation or mapping;
sensing a first degree of pressure between the first sector of the braided conductive member and first adjacent tissue at least in part by using the first pressure sensitive wire;
sensing a second degree of pressure between the second sector of the braided conductive member and second adjacent tissue at least in part by using the second pressure sensitive wire; and
providing an indication of contact between at least one sector of the braided conductive member and adjacent tissue based on the first degree of pressure and/or the second degree of pressure.

20. The method of claim 19, further comprising:
determining whether the first degree of pressure exceeds a predetermined threshold; and
determining whether the second degree of pressure exceeds the predetermined threshold,
wherein providing the indication comprises providing an indication that the first degree of pressure and/or the second degree of pressure has exceeded the predetermined threshold.

21. The method of claim 20, wherein the predetermined threshold is selected based on a degree of pressure required for successful lesion formation.

22. The method of claim 19, wherein providing the indication comprises providing an indication that each of the first degree of pressure and the second degree of pressure has exceeded a predetermined threshold.

23. The method of claim 19, wherein positioning the braided conductive member comprises positioning the braided conductive member at an orifice of the heart.

24. The method of claim 19, further comprising:
using the braided conductive member, forming a lesion in the first adjacent tissue in response to an indication that the first degree of pressure is acceptable for successful lesion formation.

25. The method of claim 24, wherein the step of forming the lesion comprises forming the lesion automatically in response to the indication that the first degree of pressure is acceptable for successful lesion formation.

26. The method of claim 19, further comprising:
detecting a mapping signal from the heart using at least one of the pressure sensitive wires.

27. The method of claim 19, further comprising:
applying ablation energy to the heart using at least one of the pressure sensitive wires.

28. The method of claim 19, further comprising:
adjusting a degree of contact between at least a portion of the braided conductive member and adjacent tissue in response to the indication.

29. The method of claim 28, wherein adjusting the degree of contact comprises adjusting the inflation of a balloon disposed within the braided conductive member.

30. The method of claim 29, wherein the first and second sectors are electrically independent, and wherein the balloon has dimensions corresponding to dimensions of the first electrically independent sector.

31. The method of claim 28, wherein adjusting the degree of contact comprises independently adjusting the inflation of a plurality of balloons disposed within the braided conductive member.

32. The method of claim 19, further comprising:
increasing the degree of contact between the first sector and the first adjacent tissue in response to an indication that the first pressure is below a predetermined threshold.

33. The method of claim 19, further comprising:
using the braided conductive member, applying ablation energy to the first adjacent tissue; and
using the braided conductive member, measuring a signal level from the first adjacent tissue; and determining if the signal level is below a first predetermined threshold;
determining if the first degree of pressure exceeds a second predetermined threshold; and
if the signal level is below the first predetermined threshold and the first degree of pressure exceeds the second predetermined threshold, providing an indication of successful lesion formation in the first adjacent tissue.

34. The method of claim 33, wherein providing the indication of successful lesion formation in the first adjacent tissue comprises providing the indication on the catheter.

35. The method of claim 33, wherein providing the indication of successful lesion formation in the first adjacent tissue comprises providing the indication on a controller coupled to the catheter.

36. The method of claim 19, further comprising:
   determining if the first degree of pressure is below a predetermined threshold; and
   prohibiting application of ablation energy to the first sector if the first degree of pressure is below the predetermined threshold.

* * * * *